(12) United States Patent
Lee et al.

(10) Patent No.: US 10,711,316 B2
(45) Date of Patent: Jul. 14, 2020

(54) PRIMERS AND KITS FOR COLONY MULTIPLEX PCR FOR THE DETECTION OF CLASS A, B, C, AND D BETA-LACTAMASE GENES AND METHODS OF USING THEREOF

(71) Applicant: MYONGJI UNIVERSITY INDUSTRY AND ACADEMIA COOPERATION FOUNDATION, Gyeonggi-Do (KR)

(72) Inventors: Sang Hee Lee, Gyeonggi-do (KR); Jung Hun Lee, Gyeonggi-do (KR)

(73) Assignee: MYONGJI UNIVERSITY INDUSTRY AND ACADEMIA COOPERATION FOUNDATION, Gyeonggi-do (KR)

( * ) Notice: Subject to any disclaimer, the term of this patent is extended or adjusted under 35 U.S.C. 154(b) by 176 days.

(21) Appl. No.: 16/122,039

(22) Filed: Sep. 5, 2018

(65) Prior Publication Data
US 2018/0363034 A1 Dec. 20, 2018

Related U.S. Application Data

(62) Division of application No. 14/283,823, filed on May 21, 2014, now abandoned.

(60) Provisional application No. 61/825,768, filed on May 21, 2013.

(51) Int. Cl.
*C12Q 1/68* (2018.01)
*C12Q 1/689* (2018.01)

(52) U.S. Cl.
CPC ........ *C12Q 1/689* (2013.01); *C12Q 2600/112* (2013.01); *C12Q 2600/16* (2013.01)

(58) Field of Classification Search
CPC .............. C12Q 1/689; C12Q 2537/143; C12Q 2600/106; C12Q 2600/16
See application file for complete search history.

(56) References Cited

U.S. PATENT DOCUMENTS

| | | | | |
|---|---|---|---|---|
| 6,013,435 A | * | 1/2000 | Nusbaum | C12Q 1/689 435/6.14 |
| 9,650,681 B2 | * | 5/2017 | Lippe | C12Q 1/689 |
| 2013/0065790 A1 | * | 3/2013 | Vos | C12Q 1/689 506/9 |

* cited by examiner

*Primary Examiner* — David C Thomas
(74) *Attorney, Agent, or Firm* — The PL Law Group, PLLC

(57) ABSTRACT

The present invention provides kits and primers for colony multiplex PCR for the detection of class A, B, C, and D β-lactamase genes. The rapid detection of bla genes by using the kits and primers according to the present invention allows appropriate prescribing of antibiotics, which can reduce patient mortality and minimize antibiotic resistance. The present invention provides kits and primers for a rapid and accurate molecular method to overcome (a) to detect all clinically-important bla genes and (b) to explain phenotypic tests' results well by using 54 primer pairs, which are designed through novel and elaborate optimization processes. With perfect specificity and sensitivity in 172 control strains and 403 clinical strains, the present invention provides prompt and clinical application to the identification of all bla genes in bacterial pathogens.

6 Claims, 42 Drawing Sheets

Specification includes a Sequence Listing.

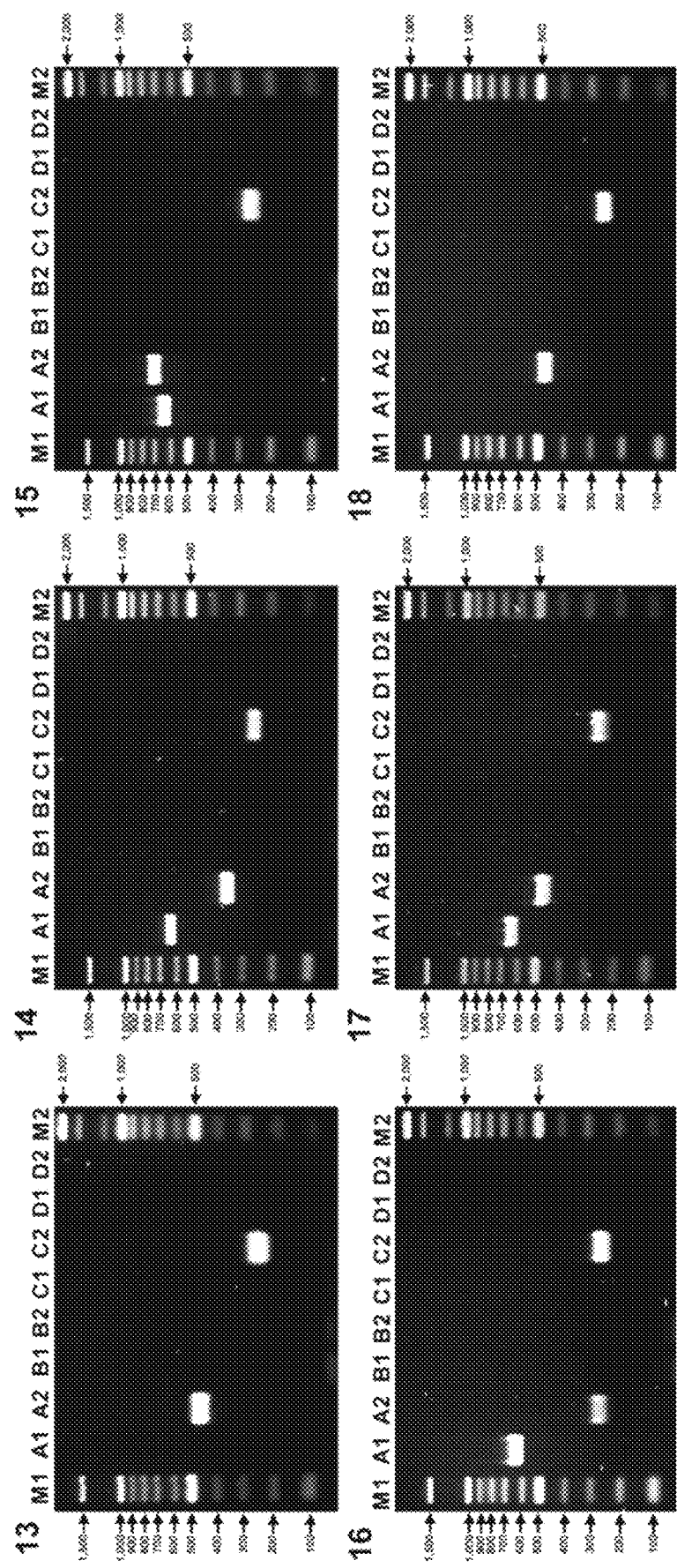

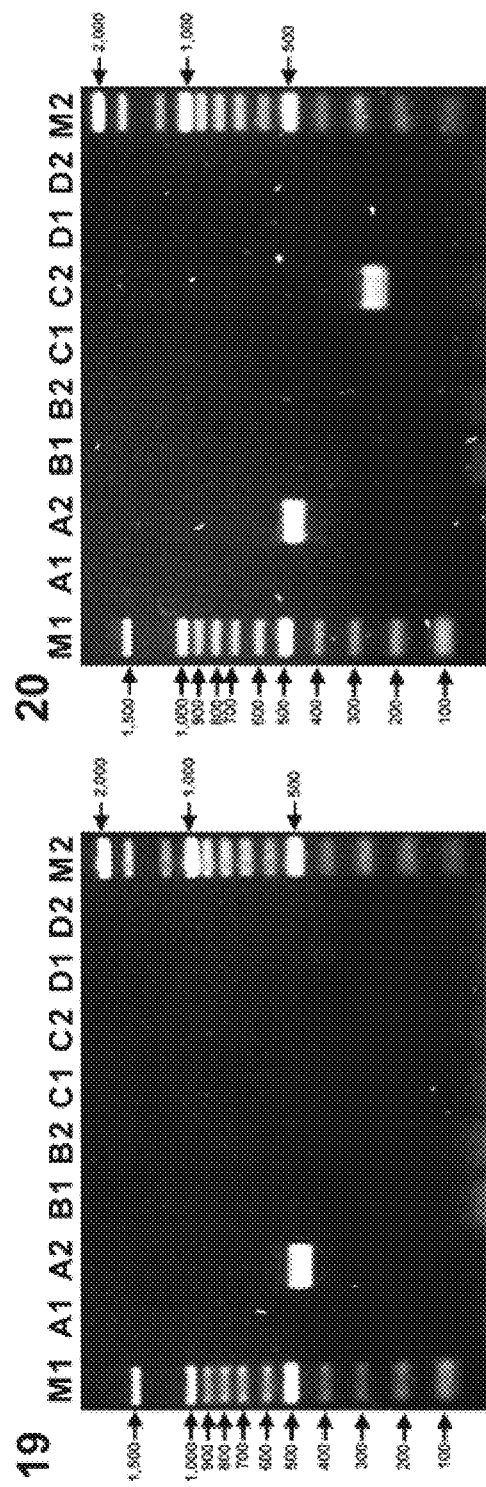

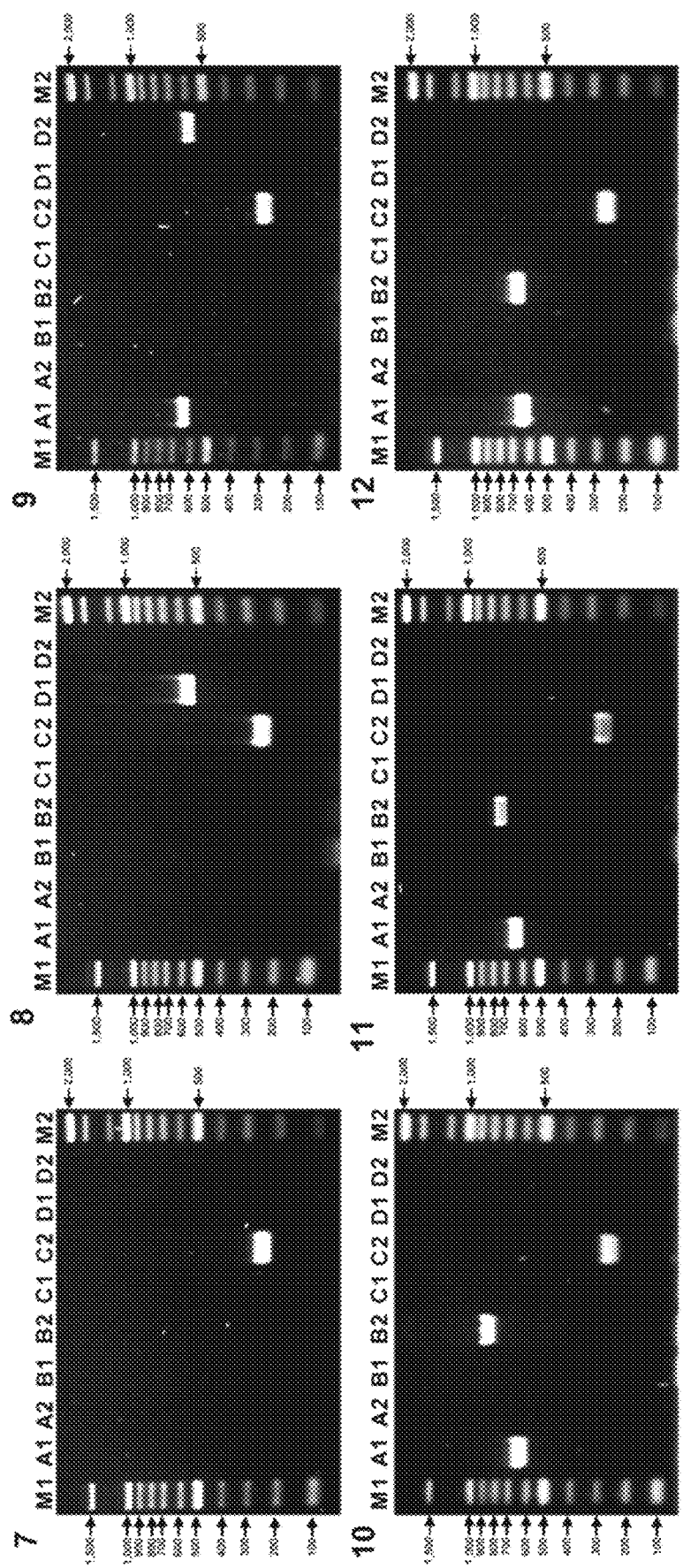

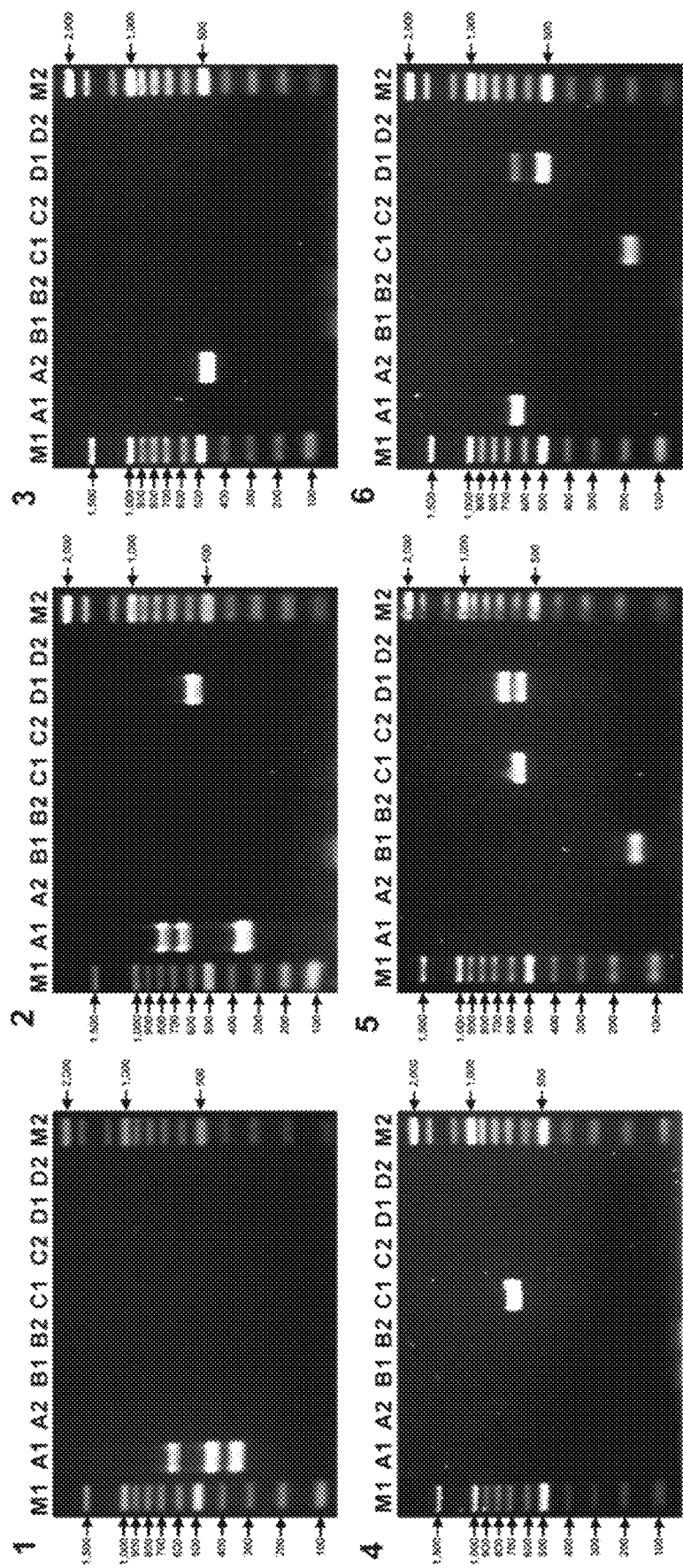

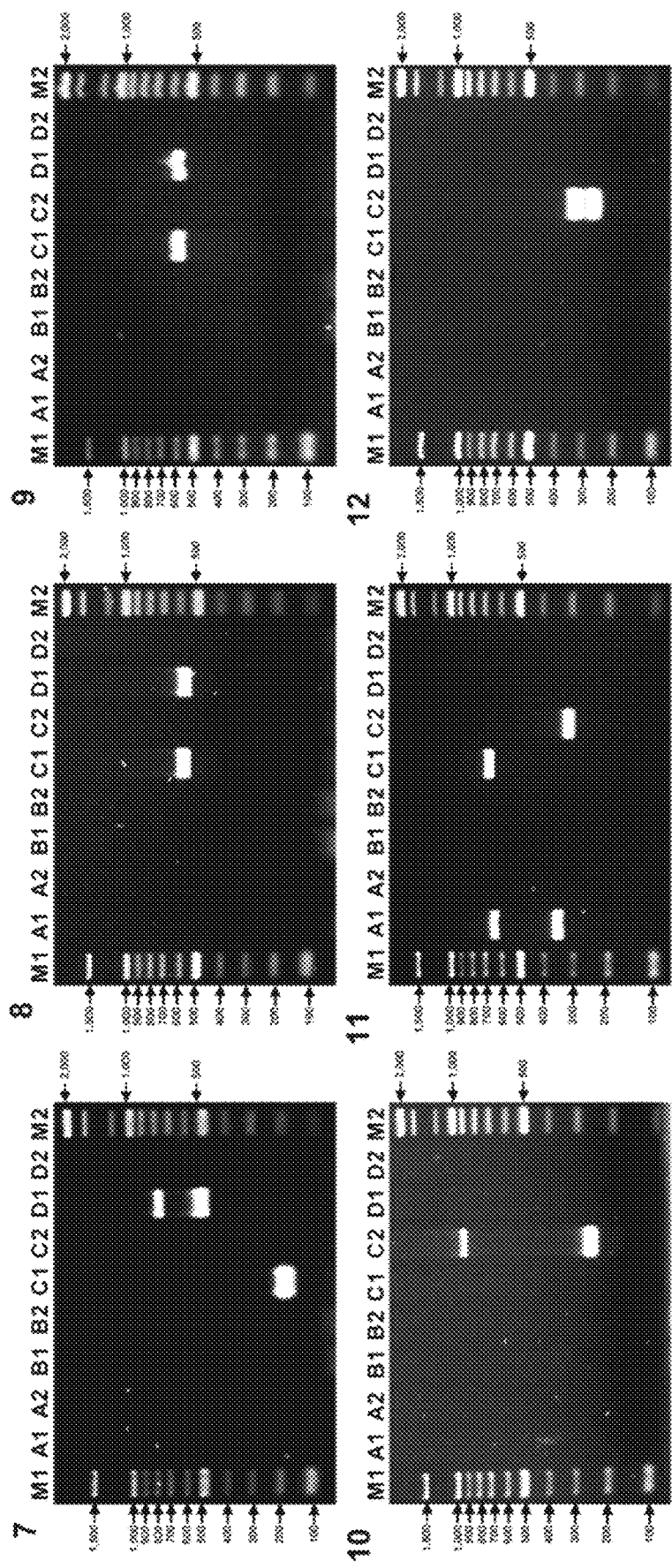

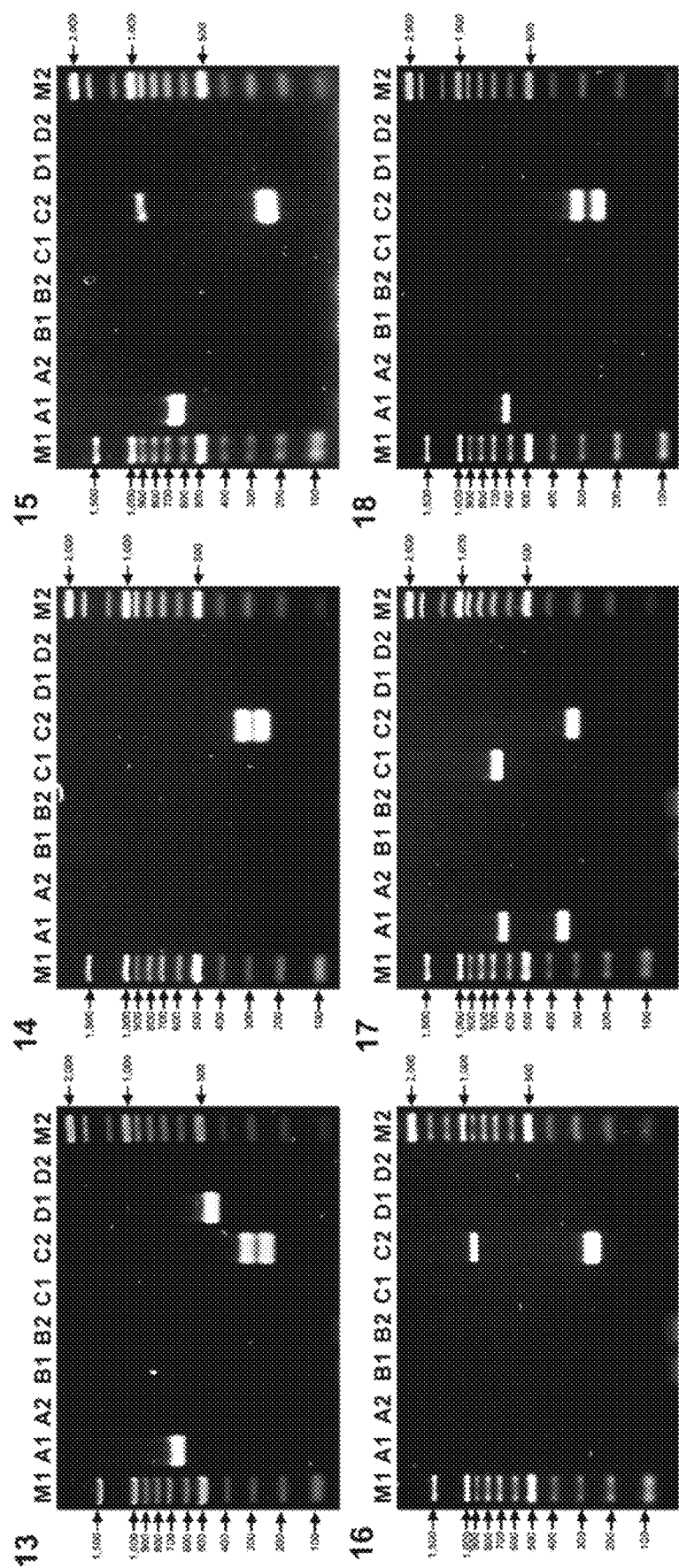

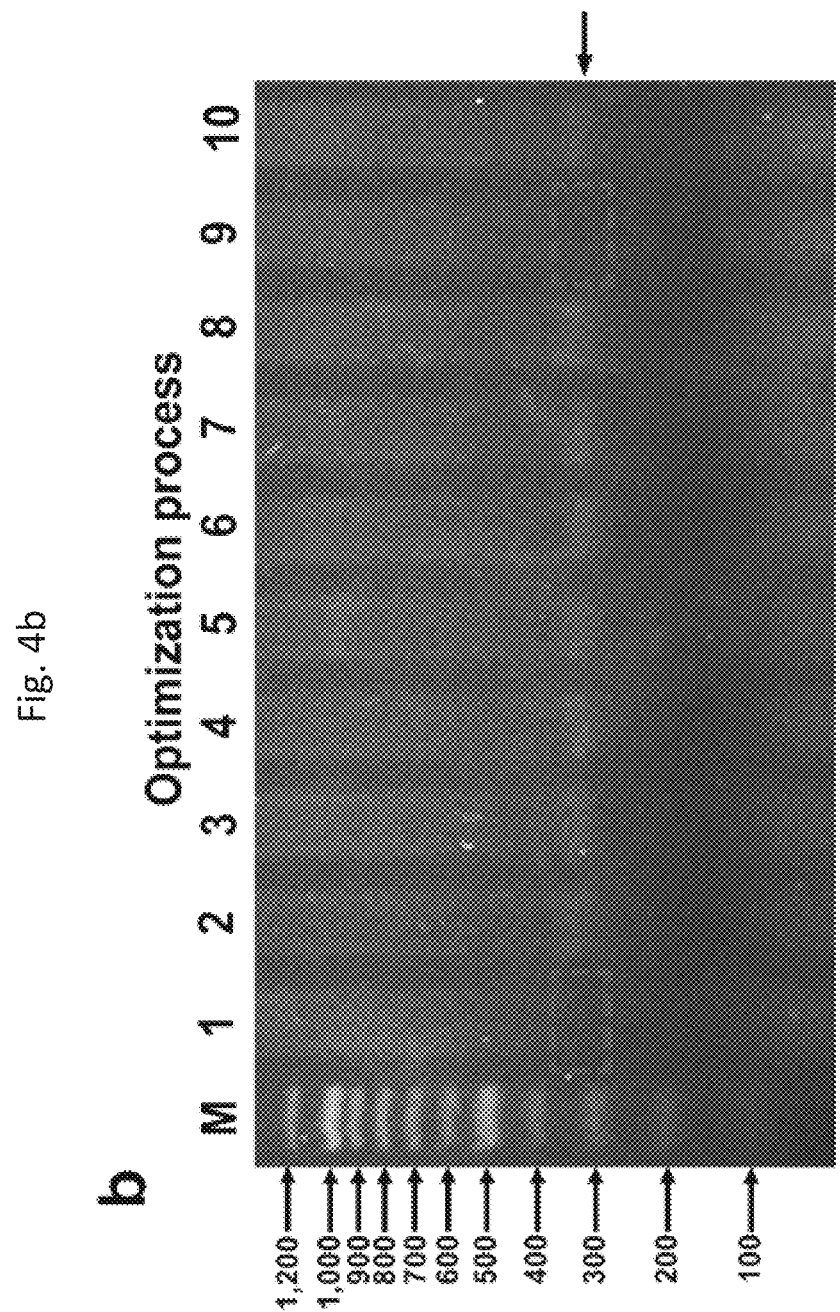

SEQUENCE LISTING

```
<160> NUMBER OF SEQ ID NOS: 108

<210> SEQ ID NO 1
<211> LENGTH: 22
<212> TYPE: DNA
<213> ORGANISM: Artificial Sequence
<220> FEATURE:
<223> OTHER INFORMATION: GES type forward primer

<400> SEQUENCE: 1
cattcacgca ctattactgg ca                                              22

<210> SEQ ID NO 2
<211> LENGTH: 20
<212> TYPE: DNA
<213> ORGANISM: Artificial Sequence
<220> FEATURE:
<223> OTHER INFORMATION: GES type reverse primer

<400> SEQUENCE: 2
agcgtaatct ctctcctggg                                                 20

<210> SEQ ID NO 3
<211> LENGTH: 19
<212> TYPE: DNA
<213> ORGANISM: Artificial Sequence
<220> FEATURE:
<223> OTHER INFORMATION: TEM type forward primer

<400> SEQUENCE: 3
cgtgtcgccc ttattccct                                                  19

<210> SEQ ID NO 4
<211> LENGTH: 20
<212> TYPE: DNA
<213> ORGANISM: Artificial Sequence
<220> FEATURE:
<223> OTHER INFORMATION: TEM type reverse primer
```

```
<400> SEQUENCE: 4
gcaactttat ccgcctccat                                              20

<210> SEQ ID NO 5
<211> LENGTH: 23
<212> TYPE: DNA
<213> ORGANISM: Artificial Sequence
<220> FEATURE:
<223> OTHER INFORMATION: NMC (IMI) type forward primer

<400> SEQUENCE: 5
gaacgatttc cattatgtag ttc                                          23

<210> SEQ ID NO 6
<211> LENGTH: 23
<212> TYPE: DNA
<213> ORGANISM: Artificial Sequence
<220> FEATURE:
<223> OTHER INFORMATION: NMC (IMI) type reverse primer

<400> SEQUENCE: 6
atcgccaact acccaatcgc ttg                                          23

<210> SEQ ID NO 7
<211> LENGTH: 19
<212> TYPE: DNA
<213> ORGANISM: Artificial Sequence
<220> FEATURE:
<223> OTHER INFORMATION: KPC type forward primer

<400> SEQUENCE: 7
gacacaccca tccgttacg                                               19

<210> SEQ ID NO 8
<211> LENGTH: 19
<212> TYPE: DNA
<213> ORGANISM: Artificial Sequence
<220> FEATURE:
<223> OTHER INFORMATION: KPC type reverse primer

<400> SEQUENCE: 8
ggttccggtt ttgtctccg                                               19

<210> SEQ ID NO 9
<211> LENGTH: 19
<212> TYPE: DNA
<213> ORGANISM: Artificial Sequence
<220> FEATURE:
<223> OTHER INFORMATION: SHV type forward primer

<400> SEQUENCE: 9
atctggtgga ctactcgcc                                               19

<210> SEQ ID NO 10
<211> LENGTH: 19
<212> TYPE: DNA
<213> ORGANISM: Artificial Sequence
<220> FEATURE:
<223> OTHER INFORMATION: SHV type reverse primer

<400> SEQUENCE: 10
atcgtccacc atccactgc                                               19

<210> SEQ ID NO 11
<211> LENGTH: 19
```

```
<212> TYPE: DNA
<213> ORGANISM: Artificial Sequence
<220> FEATURE:
<223> OTHER INFORMATION: VEB type forward primer

<400> SEQUENCE: 11
cccgatgcaa agcgttatg                                              19

<210> SEQ ID NO 12
<211> LENGTH: 20
<212> TYPE: DNA
<213> ORGANISM: Artificial Sequence
<220> FEATURE:
<223> OTHER INFORMATION: VEB type reverse primer

<400> SEQUENCE: 12
gaacagaatc agttcctccg                                             20

<210> SEQ ID NO 13
<211> LENGTH: 22
<212> TYPE: DNA
<213> ORGANISM: Artificial Sequence
<220> FEATURE:
<223> OTHER INFORMATION: PER type forward primer

<400> SEQUENCE: 13
tggatggtcg aaaccaccac ag                                          22

<210> SEQ ID NO 14
<211> LENGTH: 22
<212> TYPE: DNA
<213> ORGANISM: Artificial Sequence
<220> FEATURE:
<223> OTHER INFORMATION: PER type reverse primer

<400> SEQUENCE: 14
cgtccatcag gcaacagaat ga                                          22

<210> SEQ ID NO 15
<211> LENGTH: 21
<212> TYPE: DNA
<213> ORGANISM: Artificial Sequence
<220> FEATURE:
<223> OTHER INFORMATION: SME type forward primer

<400> SEQUENCE: 15
ggggaatgtt ctcaatgcta a                                           21

<210> SEQ ID NO 16
<211> LENGTH: 20
<212> TYPE: DNA
<213> ORGANISM: Artificial Sequence
<220> FEATURE:
<223> OTHER INFORMATION: SME type reverse primer

<400> SEQUENCE: 16
ctacaaccca atcagcagga                                             20

<210> SEQ ID NO 17
<211> LENGTH: 21
<212> TYPE: DNA
<213> ORGANISM: Artificial Sequence
<220> FEATURE:
<223> OTHER INFORMATION: CTX-M-9 type forward primer

<400> SEQUENCE: 17
```

```
gagagtgcaa cggatgatgt t                                              21
```

<210> SEQ ID NO 18
<211> LENGTH: 20
<212> TYPE: DNA
<213> ORGANISM: Artificial Sequence
<220> FEATURE:
<223> OTHER INFORMATION: CTX-M-9 type reverse primer

<400> SEQUENCE: 18

```
cagtccacga cgtcggtaag                                                20
```

<210> SEQ ID NO 19
<211> LENGTH: 20
<212> TYPE: DNA
<213> ORGANISM: Artificial Sequence
<220> FEATURE:
<223> OTHER INFORMATION: CTX-M-1 type forward primer

<400> SEQUENCE: 19

```
cagttcacgc tgatggcgac                                                20
```

<210> SEQ ID NO 20
<211> LENGTH: 20
<212> TYPE: DNA
<213> ORGANISM: Artificial Sequence
<220> FEATURE:
<223> OTHER INFORMATION: CTX-M-1 type reverse primer

<400> SEQUENCE: 20

```
ttcgtctccc agctgtcggg                                                20
```

<210> SEQ ID NO 21
<211> LENGTH: 22
<212> TYPE: DNA
<213> ORGANISM: Artificial Sequence
<220> FEATURE:
<223> OTHER INFORMATION: CTX-M-25 type forward primer

<400> SEQUENCE: 21

```
taatgacgac agcctgtgtt tc                                             22
```

<210> SEQ ID NO 22
<211> LENGTH: 22
<212> TYPE: DNA
<213> ORGANISM: Artificial Sequence
<220> FEATURE:
<223> OTHER INFORMATION: CTX-M-25 type reverse primer

<400> SEQUENCE: 22

```
cgctcaactc cccgaatgtc at                                             22
```

<210> SEQ ID NO 23
<211> LENGTH: 20
<212> TYPE: DNA
<213> ORGANISM: Artificial Sequence
<220> FEATURE:
<223> OTHER INFORMATION: CTX-M-2 type forward primer

<400> SEQUENCE: 23

```
cctgctattt agcagcgcaa                                                20
```

<210> SEQ ID NO 24
<211> LENGTH: 18
<212> TYPE: DNA
<213> ORGANISM: Artificial Sequence

```
<220> FEATURE:
<223> OTHER INFORMATION: CTX-M-2 type reverse primer

<400> SEQUENCE: 24
aggtcgctct tcttgatt                                                    18

<210> SEQ ID NO 25
<211> LENGTH: 19
<212> TYPE: DNA
<213> ORGANISM: Artificial Sequence
<220> FEATURE:
<223> OTHER INFORMATION: CTX-M-8 type forward primer

<400> SEQUENCE: 25
agacatcgcg ttaagcgga                                                   19

<210> SEQ ID NO 26
<211> LENGTH: 18
<212> TYPE: DNA
<213> ORGANISM: Artificial Sequence
<220> FEATURE:
<223> OTHER INFORMATION: CTX-M-8 type reverse primer

<400> SEQUENCE: 26
cagcgccact cccaaccg                                                    18

<210> SEQ ID NO 27
<211> LENGTH: 21
<212> TYPE: DNA
<213> ORGANISM: Artificial Sequence
<220> FEATURE:
<223> OTHER INFORMATION: THIN-B forward primer

<400> SEQUENCE: 27
acactattgg cgaagttgat g                                                21

<210> SEQ ID NO 28
<211> LENGTH: 19
<212> TYPE: DNA
<213> ORGANISM: Artificial Sequence
<220> FEATURE:
<223> OTHER INFORMATION: THIN-B reverse primer

<400> SEQUENCE: 28
tccttcgcca gccgtttcg                                                   19

<210> SEQ ID NO 29
<211> LENGTH: 22
<212> TYPE: DNA
<213> ORGANISM: Artificial Sequence
<220> FEATURE:
<223> OTHER INFORMATION: CAU-1 (Mbl1b) forward primer

<400> SEQUENCE: 29
tggtcggcaa catctattac gt                                               22

<210> SEQ ID NO 30
<211> LENGTH: 19
<212> TYPE: DNA
<213> ORGANISM: Artificial Sequence
<220> FEATURE:
<223> OTHER INFORMATION: CAU-1 (Mbl1b) reverse primer

<400> SEQUENCE: 30
tgttgaaggc ggcttcgga                                                   19
```

<210> SEQ ID NO 31
<211> LENGTH: 19
<212> TYPE: DNA
<213> ORGANISM: Artificial Sequence
<220> FEATURE:
<223> OTHER INFORMATION: SIM-1 forward primer

<400> SEQUENCE: 31
tgcggaagaa gcccagcca                                                   19

<210> SEQ ID NO 32
<211> LENGTH: 22
<212> TYPE: DNA
<213> ORGANISM: Artificial Sequence
<220> FEATURE:
<223> OTHER INFORMATION: SIM-1 reverse primer

<400> SEQUENCE: 32
tgtgagtttc aatagtgatg cg                                               22

<210> SEQ ID NO 33
<211> LENGTH: 18
<212> TYPE: DNA
<213> ORGANISM: Artificial Sequence
<220> FEATURE:
<223> OTHER INFORMATION: CphA (ImiS) type forward primer

<400> SEQUENCE: 33
cgtggtgctg atggcgag                                                    18

<210> SEQ ID NO 34
<211> LENGTH: 19
<212> TYPE: DNA
<213> ORGANISM: Artificial Sequence
<220> FEATURE:
<223> OTHER INFORMATION: CphA (ImiS) type reverse primer

<400> SEQUENCE: 34
aggttgccca gcttctcct                                                   19

<210> SEQ ID NO 35
<211> LENGTH: 22
<212> TYPE: DNA
<213> ORGANISM: Artificial Sequence
<220> FEATURE:
<223> OTHER INFORMATION: IND type forward primer

<400> SEQUENCE: 35
caataccaaa gcctgatgga tc                                               22

<210> SEQ ID NO 36
<211> LENGTH: 19
<212> TYPE: DNA
<213> ORGANISM: Artificial Sequence
<220> FEATURE:
<223> OTHER INFORMATION: IND type reverse primer

<400> SEQUENCE: 36
cgccgccttt ccattcatc                                                   19

<210> SEQ ID NO 37
<211> LENGTH: 23
<212> TYPE: DNA
<213> ORGANISM: Artificial Sequence
<220> FEATURE:
<223> OTHER INFORMATION: IMP type forward primer -continued

<400> SEQUENCE: 37
aaacacggtt tggtggttct tgt                                           23

<210> SEQ ID NO 38
<211> LENGTH: 22
<212> TYPE: DNA
<213> ORGANISM: Artificial Sequence
<220> FEATURE:
<223> OTHER INFORMATION: IMP type reverse primer

<400> SEQUENCE: 38
caaaccacta cgttatctgg ag                                            22

<210> SEQ ID NO 39
<211> LENGTH: 22
<212> TYPE: DNA
<213> ORGANISM: Artificial Sequence
<220> FEATURE:
<223> OTHER INFORMATION: NDM type forward primer

<400> SEQUENCE: 39
atctcgacat gccgggtttc gg                                            22

<210> SEQ ID NO 40
<211> LENGTH: 20
<212> TYPE: DNA
<213> ORGANISM: Artificial Sequence
<220> FEATURE:
<223> OTHER INFORMATION: NDM type reverse primer

<400> SEQUENCE: 40
aagctggttc gacaacgcat                                               20

<210> SEQ ID NO 41
<211> LENGTH: 22
<212> TYPE: DNA
<213> ORGANISM: Artificial Sequence
<220> FEATURE:
<223> OTHER INFORMATION: VIM type forward primer

<400> SEQUENCE: 41
gtgtttggtc gcatatcgca ac                                            22

<210> SEQ ID NO 42
<211> LENGTH: 21
<212> TYPE: DNA
<213> ORGANISM: Artificial Sequence
<220> FEATURE:
<223> OTHER INFORMATION: VIM type reverse primer

<400> SEQUENCE: 42
ttctcaatct ccgcgagaag t                                             21

<210> SEQ ID NO 43
<211> LENGTH: 19
<212> TYPE: DNA
<213> ORGANISM: Artificial Sequence
<220> FEATURE:
<223> OTHER INFORMATION: AIM-1 forward primer

<400> SEQUENCE: 43
tcgccctctc atccacagc                                                19

<210> SEQ ID NO 44

```
<210> SEQ ID NO 44
<211> LENGTH: 18
<212> TYPE: DNA
<213> ORGANISM: Artificial Sequence
<220> FEATURE:
<223> OTHER INFORMATION: AIM-1 reverse primer

<400> SEQUENCE: 44
ttcctcggcc aggcgctt                                                   18

<210> SEQ ID NO 45
<211> LENGTH: 23
<212> TYPE: DNA
<213> ORGANISM: Artificial Sequence
<220> FEATURE:
<223> OTHER INFORMATION: KHM-1 forward primer

<400> SEQUENCE: 45
tagctcttgt tatatcgttt ggt                                             23

<210> SEQ ID NO 46
<211> LENGTH: 20
<212> TYPE: DNA
<213> ORGANISM: Artificial Sequence
<220> FEATURE:
<223> OTHER INFORMATION: KHM-1 reverse primer

<400> SEQUENCE: 46
tagctgcaag cgcttcaact                                                 20

<210> SEQ ID NO 47
<211> LENGTH: 19
<212> TYPE: DNA
<213> ORGANISM: Artificial Sequence
<220> FEATURE:
<223> OTHER INFORMATION: FEZ-1 forward primer

<400> SEQUENCE: 47
gtcacaccga gagggaaca                                                  19

<210> SEQ ID NO 48
<211> LENGTH: 20
<212> TYPE: DNA
<213> ORGANISM: Artificial Sequence
<220> FEATURE:
<223> OTHER INFORMATION: FEZ-1 reverse primer

<400> SEQUENCE: 48
tacagcctgt gggatcaaca                                                 20

<210> SEQ ID NO 49
<211> LENGTH: 28
<212> TYPE: DNA
<213> ORGANISM: Artificial Sequence
<220> FEATURE:
<223> OTHER INFORMATION: GOB type forward primer

<400> SEQUENCE: 49
tatattacgt aggaacctat gatttggc                                        28

<210> SEQ ID NO 50
<211> LENGTH: 29
<212> TYPE: DNA
<213> ORGANISM: Artificial Sequence
<220> FEATURE:
<223> OTHER INFORMATION: GOB type reverse primer

<400> SEQUENCE: 50
```

```
aacttcagaa aatttcttat caacaataa                                29
```

<210> SEQ ID NO 51
<211> LENGTH: 26
<212> TYPE: DNA
<213> ORGANISM: Artificial Sequence
<220> FEATURE:
<223> OTHER INFORMATION: BlaB type forward primer

<400> SEQUENCE: 51

```
gccggaggtc ttgaatattt tggtaa                                   26
```

<210> SEQ ID NO 52
<211> LENGTH: 27
<212> TYPE: DNA
<213> ORGANISM: Artificial Sequence
<220> FEATURE:
<223> OTHER INFORMATION: BlaB type reverse primer

<400> SEQUENCE: 52

```
ttaatttgaa gcctttgtt tttgttg                                   27
```

<210> SEQ ID NO 53
<211> LENGTH: 23
<212> TYPE: DNA
<213> ORGANISM: Artificial Sequence
<220> FEATURE:
<223> OTHER INFORMATION: SPM-1 forward primer

<400> SEQUENCE: 53

```
gaagccgaag aaagtagtag cca                                      23
```

<210> SEQ ID NO 54
<211> LENGTH: 22
<212> TYPE: DNA
<213> ORGANISM: Artificial Sequence
<220> FEATURE:
<223> OTHER INFORMATION: SPM-1 reverse primer

<400> SEQUENCE: 54

```
gccgccaaac agcagtttct tc                                       22
```

<210> SEQ ID NO 55
<211> LENGTH: 27
<212> TYPE: DNA
<213> ORGANISM: Artificial Sequence
<220> FEATURE:
<223> OTHER INFORMATION: EBR-1 forward primer

<400> SEQUENCE: 55

```
gcaaatggaa tgtatttggt aacgaat                                  27
```

<210> SEQ ID NO 56
<211> LENGTH: 27
<212> TYPE: DNA
<213> ORGANISM: Artificial Sequence
<220> FEATURE:
<223> OTHER INFORMATION: EBR-1 reverse primer

<400> SEQUENCE: 56

```
caatctcaaa tttagaagtc gcttttc                                  27
```

<210> SEQ ID NO 57
<211> LENGTH: 22
<212> TYPE: DNA

```
<213> ORGANISM: Artificial Sequence
<220> FEATURE:
<223> OTHER INFORMATION: JOHN-1 forward primer

<400> SEQUENCE: 57
agatttctgc caatgctatg ta                                               22

<210> SEQ ID NO 58
<211> LENGTH: 23
<212> TYPE: DNA
<213> ORGANISM: Artificial Sequence
<220> FEATURE:
<223> OTHER INFORMATION: JOHN-1 reverse primer

<400> SEQUENCE: 58
tcttgtaaaa atcaaatcct cct                                              23

<210> SEQ ID NO 59
<211> LENGTH: 21
<212> TYPE: DNA
<213> ORGANISM: Artificial Sequence
<220> FEATURE:
<223> OTHER INFORMATION: ACC (AmpC-1) type forward primer

<400> SEQUENCE: 59
gttatccgtg attacctgtc t                                                21

<210> SEQ ID NO 60
<211> LENGTH: 23
<212> TYPE: DNA
<213> ORGANISM: Artificial Sequence
<220> FEATURE:
<223> OTHER INFORMATION: ACC (AmpC-1) type reverse primer

<400> SEQUENCE: 60
atccacacat tttcctgtgg cgg                                              23

<210> SEQ ID NO 61
<211> LENGTH: 23
<212> TYPE: DNA
<213> ORGANISM: Artificial Sequence
<220> FEATURE:
<223> OTHER INFORMATION: DHA (AmpC-2) type forward primer

<400> SEQUENCE: 61
gcaacactga tttccgctct gct                                              23

<210> SEQ ID NO 62
<211> LENGTH: 23
<212> TYPE: DNA
<213> ORGANISM: Artificial Sequence
<220> FEATURE:
<223> OTHER INFORMATION: DHA (AmpC-2) type reverse primer

<400> SEQUENCE: 62
tctttctgct gcggccagtc ata                                              23

<210> SEQ ID NO 63
<211> LENGTH: 26
<212> TYPE: DNA
<213> ORGANISM: Artificial Sequence
<220> FEATURE:
<223> OTHER INFORMATION: MIR (ACT, CHE, GC1, AmpC-3) type forward primer

<400> SEQUENCE: 63
tgcgctttta tcaaaactgg cagccg                                           26
```

<210> SEQ ID NO 64
<211> LENGTH: 21
<212> TYPE: DNA
<213> ORGANISM: Artificial Sequence
<220> FEATURE:
<223> OTHER INFORMATION: MIR (ACT, CHE, GC1, AmpC-3) type reverse primer

<400> SEQUENCE: 64
ggtatgccgc ctcaacgcgt g                                             21

<210> SEQ ID NO 65
<211> LENGTH: 20
<212> TYPE: DNA
<213> ORGANISM: Artificial Sequence
<220> FEATURE:
<223> OTHER INFORMATION: PDC (AmpC-4) type forward primer

<400> SEQUENCE: 65
gatcgcctga aggcactggt                                               20

<210> SEQ ID NO 66
<211> LENGTH: 20
<212> TYPE: DNA
<213> ORGANISM: Artificial Sequence
<220> FEATURE:
<223> OTHER INFORMATION: PDC (AmpC-4) type reverse primer

<400> SEQUENCE: 66
gcacgtcgag gtgggtctgt                                               20

<210> SEQ ID NO 67
<211> LENGTH: 22
<212> TYPE: DNA
<213> ORGANISM: Artificial Sequence
<220> FEATURE:
<223> OTHER INFORMATION: ADC (AmpC-5) type forward primer

<400> SEQUENCE: 67
ccgcgacagc aggtggatat gc                                            22

<210> SEQ ID NO 68
<211> LENGTH: 24
<212> TYPE: DNA
<213> ORGANISM: Artificial Sequence
<220> FEATURE:
<223> OTHER INFORMATION: ADC (AmpC-5) type reverse primer

<400> SEQUENCE: 68
gtctgtttgt acttcatctg gaaa                                          24

<210> SEQ ID NO 69
<211> LENGTH: 20
<212> TYPE: DNA
<213> ORGANISM: Artificial Sequence
<220> FEATURE:
<223> OTHER INFORMATION: CMY-2 (CFE, LAT, BIL, AmpC-6) type forward
      primer

<400> SEQUENCE: 69
gcaggagcag gctattccgg                                               20

<210> SEQ ID NO 70
<211> LENGTH: 24
<212> TYPE: DNA
<213> ORGANISM: Artificial Sequence

```
<220> FEATURE:
<223> OTHER INFORMATION: CMY-2 (CFE, LAT, BIL, AmpC-6) type reverse
      primer

<400> SEQUENCE: 70
gttttatgca cccatgaggc tttc                                           24

<210> SEQ ID NO 71
<211> LENGTH: 22
<212> TYPE: DNA
<213> ORGANISM: Artificial Sequence
<220> FEATURE:
<223> OTHER INFORMATION: Ear (AmpC-7) type forward primer

<400> SEQUENCE: 71
cgaactggtc aatcagacca tc                                             22

<210> SEQ ID NO 72
<211> LENGTH: 23
<212> TYPE: DNA
<213> ORGANISM: Artificial Sequence
<220> FEATURE:
<223> OTHER INFORMATION: Ear (AmpC-7) type reverse primer

<400> SEQUENCE: 72
tcaatgctcg acttcacgcc gta                                            23

<210> SEQ ID NO 73
<211> LENGTH: 21
<212> TYPE: DNA
<213> ORGANISM: Artificial Sequence
<220> FEATURE:
<223> OTHER INFORMATION: 520R (SRT-1, HD, SMSA, AmpC-8) type forward
      primer

<400> SEQUENCE: 73
ctatgcgcag cagcagggca a                                              21

<210> SEQ ID NO 74
<211> LENGTH: 23
<212> TYPE: DNA
<213> ORGANISM: Artificial Sequence
<220> FEATURE:
<223> OTHER INFORMATION: 520R (SRT-1, HD, SMSA, AmpC-8) type reverse
      primer

<400> SEQUENCE: 74
agatagcgaa tcagatcgcg agc                                            23

<210> SEQ ID NO 75
<211> LENGTH: 21
<212> TYPE: DNA
<213> ORGANISM: Artificial Sequence
<220> FEATURE:
<223> OTHER INFORMATION: CMY-1 (MOX, FOX, AmpC-9) type forward primer

<400> SEQUENCE: 75
tcagcgagca gaccctgttc g                                              21

<210> SEQ ID NO 76
<211> LENGTH: 23
<212> TYPE: DNA
<213> ORGANISM: Artificial Sequence
<220> FEATURE:
<223> OTHER INFORMATION: CMY-1 (MOX, FOX, AmpC-9) type reverse primer

<400> SEQUENCE: 76
```
ctatgctggg gttggagtac tgg                                              23

<210> SEQ ID NO 77
<211> LENGTH: 24
<212> TYPE: DNA
<213> ORGANISM: Artificial Sequence
<220> FEATURE:
<223> OTHER INFORMATION: BER (EC2, KL, AmpC-10) type forward primer

<400> SEQUENCE: 77
taccgcctct tgctccacat ttgc                                             24

<210> SEQ ID NO 78
<211> LENGTH: 23
<212> TYPE: DNA
<213> ORGANISM: Artificial Sequence
<220> FEATURE:
<223> OTHER INFORMATION: BER (EC2, KL, AmpC-10) type reverse primer

<400> SEQUENCE: 78
gccaccaagc acgcccgtaa atg                                              23

<210> SEQ ID NO 79
<211> LENGTH: 20
<212> TYPE: DNA
<213> ORGANISM: Artificial Sequence
<220> FEATURE:
<223> OTHER INFORMATION: OXA-23 type forward primer

<400> SEQUENCE: 79
ctggttgtac ggttcagcat                                                  20

<210> SEQ ID NO 80
<211> LENGTH: 23
<212> TYPE: DNA
<213> ORGANISM: Artificial Sequence
<220> FEATURE:
<223> OTHER INFORMATION: OXA-23 type reverse primer

<400> SEQUENCE: 80
ggcatttctg accgcatttc cat                                              23

<210> SEQ ID NO 81
<211> LENGTH: 19
<212> TYPE: DNA
<213> ORGANISM: Artificial Sequence
<220> FEATURE:
<223> OTHER INFORMATION: OXA-2 type forward primer

<400> SEQUENCE: 81
agttgtggca gacgaacgc                                                   19

<210> SEQ ID NO 82
<211> LENGTH: 19
<212> TYPE: DNA
<213> ORGANISM: Artificial Sequence
<220> FEATURE:
<223> OTHER INFORMATION: OXA-2 type reverse primer

<400> SEQUENCE: 82
aggattgccc gcacgattg                                                   19

<210> SEQ ID NO 83
<211> LENGTH: 19
<212> TYPE: DNA

<213> ORGANISM: Artificial Sequence
<220> FEATURE:
<223> OTHER INFORMATION: OXA-10 type forward primer

<400> SEQUENCE: 83
ctctgccgaa gccgtcaat                                              19

<210> SEQ ID NO 84
<211> LENGTH: 19
<212> TYPE: DNA
<213> ORGANISM: Artificial Sequence
<220> FEATURE:
<223> OTHER INFORMATION: OXA-10 type reverse primer

<400> SEQUENCE: 84
gactcagttc ccacaccag                                              19

<210> SEQ ID NO 85
<211> LENGTH: 20
<212> TYPE: DNA
<213> ORGANISM: Artificial Sequence
<220> FEATURE:
<223> OTHER INFORMATION: OXA-51 type forward primer

<400> SEQUENCE: 85
agtatgtacc tgcttcgacc                                             20

<210> SEQ ID NO 86
<211> LENGTH: 19
<212> TYPE: DNA
<213> ORGANISM: Artificial Sequence
<220> FEATURE:
<223> OTHER INFORMATION: OXA-51 type reverse primer

<400> SEQUENCE: 86
ggctgaacaa cccatccag                                              19

<210> SEQ ID NO 87
<211> LENGTH: 23
<212> TYPE: DNA
<213> ORGANISM: Artificial Sequence
<220> FEATURE:
<223> OTHER INFORMATION: OXA-1 type forward primer

<400> SEQUENCE: 87
caatcataca ccaaagacgt gga                                         23

<210> SEQ ID NO 88
<211> LENGTH: 23
<212> TYPE: DNA
<213> ORGANISM: Artificial Sequence
<220> FEATURE:
<223> OTHER INFORMATION: OXA-1 type reverse primer

<400> SEQUENCE: 88
agtttcctgt aagtgcggac aca                                         23

<210> SEQ ID NO 89
<211> LENGTH: 21
<212> TYPE: DNA
<213> ORGANISM: Artificial Sequence
<220> FEATURE:
<223> OTHER INFORMATION: OXA-24 type forward primer

<400> SEQUENCE: 89
gactttaggt gaggcaatgg c                                           21

<210> SEQ ID NO 90
<211> LENGTH: 20
<212> TYPE: DNA
<213> ORGANISM: Artificial Sequence
<220> FEATURE:
<223> OTHER INFORMATION: OXA-24 type reverse primer

<400> SEQUENCE: 90
gctccaccca accagtcaac                                              20

<210> SEQ ID NO 91
<211> LENGTH: 23
<212> TYPE: DNA
<213> ORGANISM: Artificial Sequence
<220> FEATURE:
<223> OTHER INFORMATION: OXA-63 type forward primer

<400> SEQUENCE: 91
ctaatagcaa tgctgaagga aca                                          23

<210> SEQ ID NO 92
<211> LENGTH: 22
<212> TYPE: DNA
<213> ORGANISM: Artificial Sequence
<220> FEATURE:
<223> OTHER INFORMATION: OXA-63 type reverse primer

<400> SEQUENCE: 92
ctttatatgc cggtacttgc ga                                           22

<210> SEQ ID NO 93
<211> LENGTH: 20
<212> TYPE: DNA
<213> ORGANISM: Artificial Sequence
<220> FEATURE:
<223> OTHER INFORMATION: OXA-42 type forward primer

<400> SEQUENCE: 93
tgcgaagacg atctgcacgg                                              20

<210> SEQ ID NO 94
<211> LENGTH: 20
<212> TYPE: DNA
<213> ORGANISM: Artificial Sequence
<220> FEATURE:
<223> OTHER INFORMATION: OXA-42 type reverse primer

<400> SEQUENCE: 94
caggaagcct gcgtcgtagc                                              20

<210> SEQ ID NO 95
<211> LENGTH: 20
<212> TYPE: DNA
<213> ORGANISM: Artificial Sequence
<220> FEATURE:
<223> OTHER INFORMATION: OXA-235 type forward primer

<400> SEQUENCE: 95
cttgagcctg acagcctgta                                              20

<210> SEQ ID NO 96
<211> LENGTH: 24
<212> TYPE: DNA
<213> ORGANISM: Artificial Sequence
<220> FEATURE:

<223> OTHER INFORMATION: OXA-235 type reverse primer

<400> SEQUENCE: 96
catattactt tgcatctgca tatt     24

<210> SEQ ID NO 97
<211> LENGTH: 20
<212> TYPE: DNA
<213> ORGANISM: Artificial Sequence
<220> FEATURE:
<223> OTHER INFORMATION: OXA-228 type forward primer

<400> SEQUENCE: 97
caacgcccag tcatatcaga     20

<210> SEQ ID NO 98
<211> LENGTH: 20
<212> TYPE: DNA
<213> ORGANISM: Artificial Sequence
<220> FEATURE:
<223> OTHER INFORMATION: OXA-228 type reverse primer

<400> SEQUENCE: 98
gtcaccttgc cattgggttg     20

<210> SEQ ID NO 99
<211> LENGTH: 20
<212> TYPE: DNA
<213> ORGANISM: Artificial Sequence
<220> FEATURE:
<223> OTHER INFORMATION: OXA-58 type forward primer

<400> SEQUENCE: 99
gatcagaatg ttcaagcgct     20

<210> SEQ ID NO 100
<211> LENGTH: 20
<212> TYPE: DNA
<213> ORGANISM: Artificial Sequence
<220> FEATURE:
<223> OTHER INFORMATION: OXA-58 type reverse primer

<400> SEQUENCE: 100
acagccattc cccagccact     20

<210> SEQ ID NO 101
<211> LENGTH: 18
<212> TYPE: DNA
<213> ORGANISM: Artificial Sequence
<220> FEATURE:
<223> OTHER INFORMATION: OXA-48 type forward primer

<400> SEQUENCE: 101
gggcgtagtt gtgctctg     18

<210> SEQ ID NO 102
<211> LENGTH: 20
<212> TYPE: DNA
<213> ORGANISM: Artificial Sequence
<220> FEATURE:
<223> OTHER INFORMATION: OXA-48 type reverse primer

<400> SEQUENCE: 102
cttcggtcag catggcttgt     20

```
<210> SEQ ID NO 103
<211> LENGTH: 22
<212> TYPE: DNA
<213> ORGANISM: Artificial Sequence
<220> FEATURE:
<223> OTHER INFORMATION: OXA-214 type forward primer

<400> SEQUENCE: 103
catacggtaa tgatctgaat cg                                              22

<210> SEQ ID NO 104
<211> LENGTH: 21
<212> TYPE: DNA
<213> ORGANISM: Artificial Sequence
<220> FEATURE:
<223> OTHER INFORMATION: OXA-214 type reverse primer

<400> SEQUENCE: 104
aaggtccaat gagccagaag t                                               21

<210> SEQ ID NO 105
<211> LENGTH: 20
<212> TYPE: DNA
<213> ORGANISM: Artificial Sequence
<220> FEATURE:
<223> OTHER INFORMATION: OXA-211 type forward primer

<400> SEQUENCE: 105
tgcaagcatc tgccgttccc                                                 20

<210> SEQ ID NO 106
<211> LENGTH: 22
<212> TYPE: DNA
<213> ORGANISM: Artificial Sequence
<220> FEATURE:
<223> OTHER INFORMATION: OXA-211 type reverse primer

<400> SEQUENCE: 106
ttcaatcagc agcatgtctt gt                                              22

<210> SEQ ID NO 107
<211> LENGTH: 18
<212> TYPE: DNA
<213> ORGANISM: Artificial Sequence
<220> FEATURE:
<223> OTHER INFORMATION: OXA-20 type forward primer

<400> SEQUENCE: 107
gctattcgcc tgcgtcca                                                   18

<210> SEQ ID NO 108
<211> LENGTH: 20
<212> TYPE: DNA
<213> ORGANISM: Artificial Sequence
<220> FEATURE:
<223> OTHER INFORMATION: OXA-20 type reverse primer

<400> SEQUENCE: 108
gaattgcgca ttgccgatcg                                                 20
```

PRIMERS AND KITS FOR COLONY MULTIPLEX PCR FOR THE DETECTION OF CLASS A, B, C, AND D BETA-LACTAMASE GENES AND METHODS OF USING THEREOF

CROSS-REFERENCE TO RELATED APPLICATION AND CLAIM OF PRIORITY

This application is a divisional application of application Ser. No. 14/283,823, filed on May 21, 2014, which claims the benefit of U.S. Provisional Patent Application No. 61/825,768, filed May 21, 2013, the disclosures of which are incorporated herein in their entirety by reference.

BACKGROUND

1. Technical Field

The present invention relates to a primer pairs for detection of β-lactamase genes. The present invention is also directed to kits for the detection of β-lactamase gene.

2. Description of the Related Art

The emergence and spread of multiple antibiotic resistances among pathogenic bacteria is a global health crisis1. β-Lactam antibiotics are one of the most successful drugs for the treatment of bacterial infections and represent approximately 65% of the total world market for antibiotics2. Therefore, resistance to β-lactam antibiotics by the acquisition of genes that encode β-lactamases is one of the most serious problems in Gram-negative pathogenic bacteria, such as the members of the Enterobacteriaceae, *Pseudomonas* spp., and *Acinetobacter baumannii*3,4. Since the first report observing a β-lactamase was published in 19405, a year before the introduction of first commercial antibiotic, penicillin, more than 1,200 distinct β-lactamase (bla) genes have been identified in clinical strains, showing the remarkable diversity of bla genes due to their continuous mutation4. They can be separated into the four major classes, A-D, based on their amino acid sequence and functional groups. Class A, C, and D enzymes utilize serine for β-lactam hydrolysis, while class B metalloenzymes require divalent zinc ions for substrate hydrolysis4. Of these enzymes, β-lactamases attracting the largest amount of clinical concern are extended-spectrum β-lactamases (ESBLs) which hydrolyze most penicillins and 3rd- or 4th-generation cephalosporins with an oxyimino side chain, and carbapenemases which can hydrolyze almost all β-lactam classes including carbapenems6-8. ESBL gene-harboring and carbapenemase gene-harboring Gram-negative pathogens have been responsible for increasing mortality and for serious hospital outbreaks that presented major therapeutic and infection control challenges3,7.

SUMMARY

For earlier detection of outbreaks and minimizing the spread of resistant bacteria, the availability of rapid diagnostic methods to detect resistance genes is also significantly important. Determination of susceptibility or resistance using classical culture-based phenotypic tests is the general method used in clinical microbiological laboratories, but this procedure is time consuming and can easily not detect ESBL and carbapenemase production by Enterobacteriaceae owing to variable levels of enzyme expression and the poor specificity of some antibiotic combinations9,10. In contrast, implementation of molecular-based diagnostic methods easily overcome these limitations and can increase the speed and accuracy of detecting resistance genes, which is important for both infection control and therapeutic options in hospital and community settings9. However, previous developed methods for bla gene detection are restricted to the identification of several bla genes and the molecular diagnostic method for detecting all clinically-important bla genes is not available11-17. Because these methods can detect only partial types of bla genes, they cannot replace for the susceptibility test.

For solve such problem, the present inventors designed ready-to-use 54 PCR primer pairs with optimal features that are readily usable for rapid and accurate detection of all clinically-important bla genes with perfect specificity and sensitivity. This large-scale bla detection method (designated as LARGE-SCALEblaFinder) can rapidly and accurately determine the bla gene typing of clinical strains at low cost and thus can help minimize antibiotic resistance. Notably, the LARGE-SCALEblaFinder detects 24 additional unreported bla genes in the strains that were previously studied, suggesting that this method have the ability to detect all bla genes existing in a clinical strain.

According to an aspect, the present invention provides a primer pair for identifying β-lactamase nucleic acid. The primer pair could be selected from the primer pair group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, a pair of Seq. No. 15 and 16, a pair of Seq. No. 17 and 18, a pair of Seq. No. 19 and 20, a pair of Seq. No. 21 and 22, a pair of Seq. No. 23 and 24, a pair of Seq. No. 25 and 26, a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, a pair of Seq. No. 41 and 42, a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, a pair of Seq. 57 and 58, a pair of Seq. No. 59 and 60, a pair of Seq. No. 61 and 62, a pair of Seq. No. 63 and 64, a pair of Seq. No. 65 and 66, a pair of Seq. No. 67 and 68, a pair of Seq. No. 69 and 70, a pair of Seq. No. 71 and 72, a pair of Seq. No. 73 and 74, a pair of Seq. No. 75 and 76, a pair of Seq. No. 77 and 78, a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, a pair of Seq. No. 93 and 94, a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108; and each of full-length complement primer pairs thereof. For example, the primer pairs could have at least two (2) primer pairs selected from the group. More specifically, the primer pairs could have at least five (5) primer pairs selected from the group. More further specifically, the primer pairs could have at least eight (8) primer pairs selected from the group. Most specifically, the primer pairs could be the group having all of the primer pairs (total 54 primer pairs).

The terms "complement" and "complementary," as used herein, refer to a nucleic acid that is capable of hybridizing to a specified nucleic acid molecule under stringent hybridization conditions. Thus, a specified DNA molecule is typically "complementary" to a nucleic acid if hybridization occurs between the specified DNA molecule and the nucleic acid. If the specified DNA molecule hybridizes to the full length of the nucleic acid molecule, then the specified DNA molecule is typically a "full-length complement." "Complementary," further refers to the capacity of purine and pyrimidine nucleotides to associate through hydrogen bonding in double stranded nucleic acid molecules. The following base pairs are complementary: guanine and cytosine; adenine and thymine; and adenine and uracil Hereinafter we use the classification of β-lactamase according to Ambler's molecular classification. The most widely used classification of β-lactamases is the Ambler classification35 that divides β-lactamases into four classes (A, B, C, and D) based upon their amino acid sequences. Ambler originally specified two classes: class A, the active-site serine β-lactamases; and class B, the metallo-β-lactamases that require a bivalent metal ion, usually Zn2+, for activity. Later a new class of serine β-lactamases was found that bore little sequence similarity to the then-known class A enzymes. Designated class C, its members are also known as the 'AmpC' β-lactamases. Another class of serine β-lactamases, familiarly known as the OXA β-lactamases, was found to bear little resemblance to either class A or class C and was designated class D. The three classes of serine β-lactamases are sufficiently different that alignment programs such as BLAST find no detectable sequence similarity, yet there is sufficient structural similarity among the three classes of serine β-lactamases that it is clear that they are homologous, i.e. descended from a common ancestor.

According to an aspect, the present invention provides one or more of primer pair for identifying Class A β-lactamase nucleic acid. The primer pair could be one or more of primer pair selected from the primer pair group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, a pair of Seq. No. 15 and 16, a pair of Seq. No. 17 and 18, a pair of Seq. No. 19 and 20, a pair of Seq. No. 21 and 22, a pair of Seq. No. 23 and 24, and a pair of Seq. No. 25 and 26; and each of full-length complement primer pairs thereof for identifying Class A β-lactamase nucleic acid. Specifically, the present invention provides primer pairs consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, a pair of Seq. No. 15 and 16, a pair of Seq. No. 17 and 18, a pair of Seq. No. 19 and 20, a pair of Seq. No. 21 and 22, a pair of Seq. No. 23 and 24, and a pair of Seq. No. 25 and 26 for identifying Class A β-lactamase nucleic acid.

According to an aspect, the present invention provides one or more of primer pair selected from the primer pair group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, a pair of Seq. No. 41 and 42, a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58; and each of full-length complement primer pairs thereof for identifying Class B β-lactamase nucleic acid. Specifically, the present invention provides primer pairs consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, a pair of Seq. No. 41 and 42, a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58 for identifying Class B β-lactamase nucleic acid.

According to an aspect, the present invention provides one or more of primer pair selected from the primer pair group consisting of a pair of Seq. No. 59 and 60, a pair of Seq. No. 61 and 62, a pair of Seq. No. 63 and 64, a pair of Seq. No. 65 and 66, a pair of Seq. No. 67 and 68, a pair of Seq. No. 69 and 70, a pair of Seq. No. 71 and 72, a pair of Seq. No. 73 and 74, a pair of Seq. No. 75 and 76, and a pair of Seq. No. 77 and 78; and each of full-length complement primer pairs thereof for identifying Class C β-lactamase nucleic acid. Specifically, the present invention provides primer pairs consisting of a pair of Seq. No. 59 and 60, a pair of Seq. No. 61 and 62, a pair of Seq. No. 63 and 64, a pair of Seq. No. 65 and 66, a pair of Seq. No. 67 and 68, a pair of Seq. No. 69 and 70, a pair of Seq. No. 71 and 72, a pair of Seq. No. 73 and 74, a pair of Seq. No. 75 and 76, and a pair of Seq. No. 77 and 78 for identifying Class C β-lactamase nucleic acid.

According to an aspect, the present invention provides one or more of primer pair selected from the primer pair group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, a pair of Seq. No. 93 and 94, a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108; and each of full-length complement primer pairs thereof for identifying Class D β-lactamase nucleic acid. Specifically, the present invention provides primer pairs consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, a pair of Seq. No. 93 and 94, a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108 for identifying Class D β-lactamase nucleic acid.

According to an aspect, the present invention provides a detection kit for identifying β-lactamase nucleic acid, wherein the kit comprises the primer pair Specifically, the primer pairs could have at least two (2) primer pairs selected from the group. More specifically, the primer pairs could have at least five (5) primer pairs selected from the group. Further more specifically, the primer pairs could have at least eight (8) primer pairs selected from the group. Most specifically, the primer pairs could be the group having all of the primer pairs (total 54 primer pairs).

According to an aspect of the present invention, a method for treating a patient with bacterial infection includes determining a β-lactamase (bla) gene of a bacterial pathogen in the patient by performing a multiplex polymerase chain reaction (PCR) with the primer pairs, determining a β-Lactam antibiotics to which the bacterial pathogen is not resistant, in accordance with the determination of the β-lactamase (bla) gene, and administering the β-Lactam antibiotics to the patient.

According to an aspect, the present invention provides a detection kit for identifying β-lactamase nucleic acid, wherein the kit comprises:

a) at least one of the primer pair capable of hybridizing to β-lactamase nucleic acid;
b) at least one positive control and at least one negative control; and
c) a protocol for identification of β-lactamase nucleic acid.

Specifically, the kit is for identifying class A β-lactamase nucleic acid comprising one or more of primer pair selected from the group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16, a pair of Seq. No. 17 and 18, a pair of Seq. No. 19 and 20, a pair of Seq. No. 21 and 22, a pair of Seq. No. 23 and 24, and a pair of Seq. No. 25 and 26; and each of full-length complement primer pairs thereof.

Specifically, the kit is for identifying class A (A1) β-lactamase nucleic acid comprising one or more of primer pair selected from the group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16.

Specifically, the kit is for identifying class A (A2) β-lactamase nucleic acid comprising one or more of primer pair selected from the group consisting of a pair of Seq. No. 17 and 18, a pair of Seq. No. 19 and 20, a pair of Seq. No. 21 and 22, a pair of Seq. No. 23 and 24, and a pair of Seq. No. 25 and 26; and each of full-length complement primer pairs thereof.

Specifically, the kit is for identifying class B β-lactamase nucleic acid comprising one or more of primer pair selected from the group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, a pair of Seq. No. 41 and 42, a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58; and each of full-length complement primer pairs thereof.

Specifically, the kit is for identifying class B (B1) β-lactamase nucleic acid comprising one or more of primer pair selected from the group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, and a pair of Seq. No. 41 and 42; and each of full-length complement primer pairs thereof.

Specifically, the kit is for identifying class B (B2) β-lactamase nucleic acid comprising one or more of primer pair selected from the group consisting of a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58; and each of full-length complement primer pairs thereof.

Specifically, the kit is for identifying class C β-lactamase nucleic acid comprising one or more of primer pair selected from the group consisting of a pair of Seq. No. 59 and 60, a pair of Seq. No. 61 and 62, a pair of Seq. No. 63 and 64, a pair of Seq. No. 65 and 66, a pair of Seq. No. 67 and 68, a pair of Seq. No. 69 and 70, a pair of Seq. No. 71 and 72, a pair of Seq. No. 73 and 74, a pair of Seq. No. 75 and 76, a pair of Seq. No. 77 and 78; and each of full-length complement primer pairs thereof.

Specifically, the kit is for identifying class C (C1) β-lactamase nucleic acid comprising one or more of primer pair selected from the group consisting of a pair of Seq. No. 59 and 60, a pair of Seq. No. 61 and 62, a pair of Seq. No. 63 and 64, a pair of Seq. No. 65 and 66, and a pair of Seq. No. 67 and 68; and each of full-length complement primer pairs thereof.

Specifically, the kit is for identifying class C (C2) β-lactamase nucleic acid comprising one or more of primer pair selected from the group consisting of a pair of Seq. No. 69 and 70, a pair of Seq. No. 71 and 72, a pair of Seq. No. 73 and 74, a pair of Seq. No. 75 and 76, a pair of Seq. No. 77 and 78; and each of full-length complement primer pairs thereof.

Specifically, the kit is for identifying class D β-lactamase nucleic acid comprising one or more of primer pair selected from the group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, a pair of Seq. No. 93 and 94, a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108; and each of full-length complement primer pairs thereof.

Specifically, the kit is for identifying class D (D1) β-lactamase nucleic acid comprising one or more of primer pair selected from the group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, and a pair of Seq. No. 93 and 94; and each of full-length complement primer pairs thereof.

Specifically, the kit is for identifying class D (D2) β-lactamase nucleic acid comprising one or more of primer pair selected from the group consisting of a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108; and each of full-length complement primer pairs thereof.

According to an aspect, the present invention provides a method of identifying β-lactamase type from a sample, comprising:
(a) contacting in solution the sample with one of more of the primer pairs;
(b) simultaneously amplifying by polymerase chain reaction (PCR) in one reaction chamber using the primer pair to produce amplified nucleic acid products; and
(c) detecting the nucleic acid products by gel electrophoresis.

More specifically, the present invention could comprise further step for sequencing of PCR product.

According to an embodiment of the present invention, a detection kit is for identifying β-lactamase nucleic acid, wherein the kit comprises: a) at least one of the primer pair capable of hybridizing to β-lactamase nucleic acid; b) at least one positive control and at least one negative control; and c) a protocol for identification of β-lactamase nucleic acid.

According to an embodiment of the present invention, a method of identifying β-lactamase type from a sample, includes: (a) contacting in solution the sample with one of more of the primer pairs; (b) simultaneously amplifying by polymerase chain reaction (PCR) in one reaction chamber using the primer pair to produce amplified nucleic acid products; and (c) detecting the nucleic acid products by gel electrophoresis.

According to an embodiment of the present invention, the method further includes sequencing of PCR product.

The present invention provides a rapid and accurate molecular method to overcome the failure (a) to detect all clinically-important bla genes and (b) to explain phenotypic tests' results well by using 54 primer pairs, which are designed through novel and elaborate optimization processes. With perfect specificity and sensitivity in 172 control strains and 403 clinical strains, the present method (LARGE-SCALEblaFinder) could detect all clinically-important bla genes. Therefore, this large-scale bla detection ability of LARGE-SCALEblaFinder enables prompt and clinical application to the identification of all bla genes in bacterial pathogens.

BRIEF DESCRIPTION OF THE DRAWINGS

FIGS. 3a-1 to 3a-5 show results from multiplex PCR assays for the detection of A1-specific bla genes in positive (17) or negative (9) control strains. (1) E. coli TOPC015 harboring CTX-M-15 (lane A2) and BER (EC2, KL, AmpC-10) type (lane C2). (2) E. coli TOPC055 harboring CTX-M-55 (lane A2) and BER (EC2, KL, AmpC-10) type (lane C2). (3) E. coli JAEE1 harboring IMP-1 (lane B1) and BER (EC2, KL, AmpC-10) type (lane C2). (4) E. coli C600 harboring MIR-1 (lane C1) and BER (EC2, KL, AmpC-10) type (lane C2). (5) E. cloacae 10-12 703 harboring ACT-2 (lane C1). (6) E. coli TOPCMY010 harboring CMY-10 (lane C2) and BER (EC2, KL, AmpC-10) type (lane C2). (7) E. coli BER harboring BER (lane C2). (8) P. aeruginosa 08PAE8 harboring OXA-2 (lane D1) and MIR (ACT, CHE, GC1, AmpC-3) type (lane C1). (9) E. coli TOPO210 harboring OXA-210 (lane D1) and BER (EC2, KL, AmpC-10) type (lane C2). (10) *E. coli* CF804 harboring TEM-8 (lane A1) and BER (EC2, KL, AmpC-10) type (lane C2). (11) *E. coli* CF244 harboring TEM-15 (lane A1) and BER (EC2, KL, AmpC-10) type (lane C2). (12) *E. coli* CF0022 harboring TEM-30 (lane 1) and BER (EC2, KL, AmpC-10) type (lane C2). (13) *E. coli* CF0012 harboring TEM-31 (lane A1) and BER (EC2, KL, AmpC-10) type (lane C2). (14) *E. coli* 57461 harboring TEM-34 (lane A1) and BER (EC2, KL, AmpC-10) type (lane C2). (15) *E. coli* CF0042 harboring TEM-35 (lane A1) and BER (EC2, KL, AmpC-10) type (lane C2). (16) *K. pneumoniae* L-867 harboring TEM-49 (lane A1) and SHV type (lane A1). (17) *E. coli* L267 harboring TEM-47 (lane A1) and BER (EC2, KL, AmpC-10) type (lane C2). (18) *E. coli* ECLA-4 harboring SHV-2a (lane A1) [In addition, TEM type (lane A1) and BER (EC2, KL, AmpC-10) type (lane C2) were newly detected by bla detection method]. (19) *E. coli* HB101 harboring SHV-11 (lane A1) and BER (EC2, KL, AmpC-10) type (lane C2). (20) *E. coli* ECZP-1 harboring SHV-12 (lane A1) [In addition, TEM type (lane A1) and BER (EC2, KL, AmpC-10) type (lane C2)were newly detected by bla detection method]. (21) *K. pneumoniae* CL5761 harboring KPC-3 (lane A1) [In addition, TEM type (lane A1) and SHV type (lane A1) were newly detected by bla detection method]. (22) *E. coli* TOPSME01 harboring SME-1 (lane A1), TEM type (lane A1), and BER (EC2, KL, AmpC-10) type (lane C2). (23) *K. pneumoniae* CHAK36 harboring GES-5 (lane A1), SHV-12 (lane A1), and OXA-17 (lane D1) [In addition, TEM type (lane A1) was newly detected by bla detection method]. (24) *E. coli* pCCLLimiA harboring IMI-1 (lane A1) and BER (EC2, KL, AmpC-10) type (lane C2). (25) *E. coli* TOPVEB02 harboring VEB-2 (lane A1), TEM type (lane A1), and BER (EC2, KL, AmpC-10) type (lane C2). (26) *E. coli* TOPPER02 harboring PER-2 (lane A1),TEM type (lane A1), and BER (EC2, KL, AmpC-10) type (lane C2). Lane M1, 100 bp DNA size marker (Biosesang, Korea); Lane M2, 100 bp plus DNA size marker (Bioneer, Korea); lane A1, A1 multiplex tube; lane A2, A2 multiplex tube; lane B1, B1 multiplex tube; lane B2, B2 multiplex tube; lane C1, C1 multiplex tube; lane C2, C2 multiplex tube; lane D1, D1 multiplex tube; lane D2, D2 multiplex tube.

FIGS. 3b-1 to 3b-4 show results from multiplex PCR assays for the detection of A2-specific bla genes in positive (11) or negative (9) control strains. (1) *E. coli* CF804 harboring TEM-8 (lane A1) and BER (EC2, KL, AmpC-10) type (lane C2). (2) *E. coli* CF244 harboring TEM-15 (lane A1) and BER (EC2, KL, AmpC-10) type (lane C2). (3) *C. freundii* 11-7F4560 harboring VIM-2 (lane B1), TEM type (lane A1), CMY-2 (CFE, LAT, BIL, AmpC-6) type (lane C2), CMY-1 (MOX, FOX, AmpC-9) type (lane C2), OXA-1 type (lane D1), and OXA-23 type (lane D1). (4) *E. coli* TOPIND06 harboring IND-6 (lane B1), TEM type (lane A1), and BER (EC2, KL, AmpC-10) type (lane C2). (5) *E. coli* TOPACC04 harboring ACC-4 (lane C1), TEM type (lane A1), and BER (EC2, KL, AmpC-10) type (lane C2). (6) *E. coli* TOPPDC03 harboring PDC-3 (lane C1), TEM type (lane A1), and BER (EC2, KL, AmpC-10) type (lane C2). (7) *P. aeruginosa* 08PAE4 harboring OXA-2 (lane D1), TEM type (lane A1), MIR (ACT, CHE, GC1, AmpC-3) type (lane C1), and CMY-1 (MOX, FOX, AmpC-9) type (lane C2). (8) *E. coli* TOPDXA040 harboring OXA-40 (lane D1), TEM type (lane A1), and BER (EC2, KL, AmpC-10) type (lane C2). (9) *E. coli* TOPDXA020 harboring OXA-20 (lane D2), TEM type (lane A1), and BER (EC2, KL, AmpC-10) type (lane C2). (10) *E. coli* A15R(+) harboring CTX-M-3 (lane A2) [In addition, TEM type (lane A1) and BER (EC2, KL, AmpC-10) type (lane C2) were newly detected by bla detection method]. (11) *E. coli* TOPC008 harboring CTX-M-8 (lane A2), TEM type (lane A1), and BER (EC2, KL, AmpC-10) type (lane C2). (12) *E. coli* K0519020 harboring CTX-M-15 (lane A2) [In addition, TEM type (lane A1), BER (EC2, KL, AmpC-10) type (lane C2), and OXA-1 type (lane D1) were newly detected by bla detection method]. (13) *E. coli* TOPC015 harboring CTX-M-15 (lane A2) and BER (EC2, KL, AmpC-10) type (lane C2). (14) *E. coli* TOPC025 harboring CTX-M-25 (lane A2), TEM type (lane A1), and BER (EC2, KL, AmpC-10) type (lane C2). (15) *E. coli* TOPC027 harboring CTX-M-27 (lane A2), TEM type (lane A1), and BER (EC2, KL, AmpC-10) type (lane C2). (16) *E. coli* TOPC043 harboring CTX-M-43 (lane A2), TEM type (lane A1), and BER (EC2, KL, AmpC-10) type (lane C2). (17) *E. coli* T034 harboring CTX-M-55 (lane A2), TEM type (lane A1), and BER (EC2, KL, AmpC-10) type (lane C2). (18) *E. coli* TOPC055 harboring CTX-M-55 (lane A2) and BER (EC2, KL, AmpC-10) type (lane C2). (19) *P. rettgeri* PS022 harboring CTX-M-114 (lane A2). (20) *E. coli* TOPC114 harboring CTX-M-114 (lane A2) and BER (EC2, KL, AmpC-10) type (lane C2).

FIGS. 3c-1 to 3c-4 show results from multiplex PCR assays for the detection of B1-specific bla genes in positive (10) or negative (9) control strains. (1) *E. coli* CF0022 harboring TEM-30 (lane A1) and BER (EC2, KL, AmpC-10) type (lane C2). (2) *E. coli* L267 harboring TEM-47 (lane A1) and BER (EC2, KL, AmpC-10) type (lane C2). (3) *E. coli* CF0012 harboring TEM-31 (lane A1) and BER (EC2, KL, AmpC-10) type (lane C2). (4) *E. coli* TOPAIM01 harboring AIM-1 (lane B2), TEM type (lane A1), and BER (EC2, KL, AmpC-10) type (lane C2). (5) *E. coli* E07-39524 harboring DHA-1 (lane C1), TEM type (lane A1), CTX-M-1 type (lane A2), CTX-M-9 type (lane A2), BER (EC2, KL, AmpC-10) type (lane C2), and OXA-1 type (lane D1). (6) *E. aerogenes* K9911729 harboring CMY-10 (lane C2), TEM type (lane A1), SHV type, (lane A1), and MIR (ACT, CHE, GC1, AmpC-3) type (lane C1). (7) *E. coli* K986110 harboring CMY-11 (lane C2) [In addition, TEM type (lane A1), OXA-1 type (lane D1), and BER (EC2, KL, AmpC-10) type (lane C2) were newly detected by bla detection method]. (8) *E. coli* TOPO002 harboring OXA-2 (lane D1) and BER (EC2, KL, AmpC-10) type (lane C2). (9) *E. coli* TOPDXA048 harboring OXA-48 (lane D2), TEM type (lane A1), and BER (EC2, KL, AmpC-10) type (lane C2). (10) *E. coli* JAEE1 harboring IMP-1 (lane B1) and BER (EC2, KL, AmpC-10) type (lane C2). (11) *C. freundii* 11-7F4560 harboring VIM-2 (lane B1), TEM type (lane A1), CMY-2 (CFE, LAT, BIL, AmpC-6) type (lane C2), CMY-1 (MOX, FOX, AmpC-9) type (lane C2), OXA-1 type (lane D1), and OXA-23 type (lane D1). (12) *E. coli* TOPIND06 harboring IND-6 (lane B1), TEM type (lane A1), and BER (EC2, KL, AmpC-10) type (lane C2). (13) *E. coli* TOPNDM01 harboring NDM-1 (lane B1), TEM type (lane A1), and BER (EC2, KL, AmpC-10) type (lane C2). (14) *E. coli* TOPCPHA harboring CphA (lane B1), TEM type (lane A1), and BER (EC2, KL, AmpC-10) type (lane C2). (15) *E. coli* TOPIMIS harboring ImiS (lane B1), TEM type (lane A1), and BER (EC2, KL, AmpC-10) type (lane C2). (16) *E. coli* TOPCAU01 harboring CAU-1 (lane B1), TEM type (lane A1), and BER (EC2, KL, AmpC-10) type (lane C2). (17) *E. coli* TOPMBL1B harboring Mbl1b (lane B1), TEM type (lane A1), and BER (EC2, KL, AmpC-10) type (lane C2). (18) *E. coli* TOPSIM01harboring SIM-1 (lane B1), TEM type (lane A1), and BER (EC2, KL, AmpC-10) type (lane C2). (19) *E. coli* TOPTHINB harboring THIN-B (lane B1), TEM type (lane A1), and BER (EC2, KL, AmpC-10) type (lane C2).

FIGS. 3d-1 to 3d-3 show results from multiplex PCR assays for the detection of B2-specific bla genes in positive (8) or negative (9) control strains. (1) E. coli 57461 harboring TEM-34 (lane A1) and BER (EC2, KL, AmpC-10) type (lane C2). (2) E. coli CF0042 harboring TEM-35 (lane A1) and BER (EC2, KL, AmpC-10) type (lane C2). (3) E. coli A15R(+) harboring CTX-M-3 (lane A2) [In addition, TEM type (lane A1) and BER (EC2, KL, AmpC-10) type (lane C2) were newly detected by bla detection method]. (4) E. coli TOPNDM01 harboring NDM-1 (lane B1), TEM type (lane A1), and BER (EC2, KL, AmpC-10) type (lane C2). (5) E. coli TOPGC1 harboring GC1 (lane C1), TEM type (lane A1), and BER (EC2, KL, AmpC-10) type (lane C2). (6) E. coli 520R harboring 520R (lane C2) and BER (EC2, KL, AmpC-10) type (lane C2). (7) E. coli MG1655 harboring BER (EC2, KL, AmpC-10) type (lane C2). (8) E. coli TOPO010 harboring OXA-10 (lane D1) and BER (EC2, KL, AmpC-10) type (lane C2). (9) E. coli TOPDXAO058 harboring OXA-58 (lane D2), TEM type (lane A1), and BER (EC2, KL, AmpC-10) type (lane C2). (10) E. coli TOPAIM01 harboring AIM-1 (lane B2), TEM type (lane A1), and BER (EC2, KL, AmpC-10) type (lane C2). (11) E. coli TOPKHM01 harboring KHM-1 (lane B2), TEM type (lane A1), and BER (EC2, KL, AmpC-10) type (lane C2). (12) E. coli TOPFEZ01 harboring FEZ-1 (lane B2), TEM type (lane A1), and BER (EC2, KL, AmpC-10) type (lane C2). (13) E. coli TOPGOB01 harboring GOB-1 (lane B2), TEM type (lane A1), and BER (EC2, KL, AmpC-10) type (lane C2). (14) E. coli TOPBLAB01 harboring BlaB-1 (lane B2), TEM type (lane A1), and BER (EC2, KL, AmpC-10) type (lane C2). (15) E. coli TOPSPM01 harboring SPM-1 (lane B2), TEM type (lane A1), and BER (EC2, KL, AmpC-10) type (lane C2). (16) E. coli TOPEBR01 harboring EBR-1 (lane B2), TEM type (lane A1), and BER (EC2, KL, AmpC-10) type (lane C2). (17) E. coli TOPJOHN01 harboring JOHN-1 (lane B2), TEM type (lane A1), and BER (EC2, KL, AmpC-10) type (lane C2).

FIGS. 3e-1 to 3e-3 show results from multiplex PCR assays for the detection of C1-specific bla genes in positive (9) or negative (9) control strains. (1) E. coli ECLA-4 harboring SHV-2a (lane A1) [In addition, TEM type (lane A1) and BER (EC2, KL, AmpC-10) type (lane C2) were newly detected by bla detection method]. (2) E. coli HB101 harboring SHV-11 (lane A1) and BER (EC2, KL, AmpC-10) type (lane C2). (3) E. coli TOPCPHA harboring CphA (lane B1), TEM type (lane A1), and BER (EC2, KL, AmpC-10) type (lane C2). (4) E. coli TOPIMIS harboring ImiS (lane B1), TEM type (lane A1), and BER (EC2, KL, AmpC-10) type (lane C2). (5) E. coli TOPFEZ01 harboring FEZ-1 (lane B2), TEM type (lane A1), and BER (EC2, KL, AmpC-10) type (lane C2). (6) E. coli TOPCMY011 harboring CMY-11 (lane C2) and BER (EC2, KL, AmpC-10) type (lane C2). (7) E. coli ATCC25922 harboring BER (EC2, KL, AmpC-10) type (lane C2). (8) E. coli TOPDXA031 harboring OXA-31 (lane D1), TEM type (lane A1), and BER (EC2, KL, AmpC-10) type (lane C2). (9) E. coli TOPDXAO097 harboring OXA-97 (lane D2), TEM type (lane A1), and BER (EC2, KL, AmpC-10) type (lane C2). (10) E. coli TOPACC04 harboring ACC-4 (lane C1), TEM type (lane A1), and BER (EC2, KL, AmpC-10) type (lane C2). (11) E. coli E07-39524 harboring DHA-1 (lane C1), TEM type (lane A1), CTX-M-1 type (lane A2), CTX-M-9 type (lane A2), BER (EC2, KL, AmpC-10) type (lane C2), and OXA 1 type (lane D1). (12) E. coli TOPPDC03 harboring PDC-3 (lane C1), TEM type (lane A1), and BER (EC2, KL, AmpC-10) type (lane C2). (13) E. coli C600 harboring MIR-1 (lane C1) and BER (EC2, KL, AmpC-10) type (lane C2). (14) E. cloacae 10-12 703 harboring ACT-2 (lane C1). (15) E. coli TOPGC1 harboring GC1 (lane C1), TEM type (lane A1), and BER (EC2, KL, AmpC-10) type (lane C2). (16) E. cloacae CHE harboring CHE (lane C1). (17) E. coli TOPADC002 harboring ADC-2 (lane C1), TEM type (lane A1), and BER (EC2, KL, AmpC-10) type (lane C2). (18) E. coli TOPADC033 harboring ADC-33 (lane C1), TEM type (lane A1), and BER (EC2, KL, AmpC-10) type (lane C2).

FIGS. 3f-1 to 3f-5 show results from multiplex PCR assays for the detection of C2-specific bla genes in positive (20) or negative (9) control strains. (1) K. pneumoniae CL5761 harboring KPC-3 (lane A1) [In addition, TEM type (lane A1) and SHV type (lane A1) were newly detected by bla detection method]. (2) K. pneumoniae CHAK36 harboring GES-5 (lane A1), SHV-12 (lane A1), OXA-17 (lane D1), [In addition, TEM type (lane A1) was newly detected by bla detection method]. (3) P. rettgeri PS022 harboring CTX-M-114 (lane A2). (4) E. cloacae CHE harboring CHE (lane C1). (5) P. aeruginosa 08PAE32 harboring OXA-10 (lane D1), VIM type (lane B1), MIR (ACT, CHE, GC1, AmpC-3) type (lane C1), and OXA-23 type (lane D1). (6) A. baumannii AB4-1 harboring OXA-21 (lane D1), TEM type (lane A1), ADC (AmpC-5) type (lane C1), and OXA-10 type (lane D1). (7) A. baumannii K0420859 harboring OXA-23 (lane D1) [In addition, ADC (AmpC-5) type (lane C1) and OXA-10 type (lane D1) were newly detected by bla detection method]. (8) P. aeruginosa WK20 harboring OXA-10 (lane D1) and MIR (ACT, CHE, GC1, AmpC-3) type (lane C1). (9) P. aeruginosa WK28 harboring OXA-240 (lane D1) and AmpCCARBA-2 type (lane C1). (10) E. coli JM109 harboring CMY-3 (lane C2) and BER (EC2, KL, AmpC-10) type (lane C2). (11) E. aerogenes K9911729 harboring CMY-10 (lane C2), TEM type (lane A1), SHV type, (lane A1), and MIR (ACT, CHE, GC1, AmpC-3) type (lane C1). (12) E. coli TOPCMY010 harboring CMY-10 (lane C2) and BER (EC2, KL, AmpC-10) type (lane C2). (13) E. coli K986110 harboring CMY-11 (lane C2) [In addition, TEM type (lane A1), OXA-1 type (lane D1), and BER (EC2, KL, AmpC-10) type (lane C2) were newly detected by bla detection method]. (14) E. coli TOPCMY011 harboring CMY-11 (lane C2) and BER (EC2, KL, AmpC-10) type (lane C2). (15) E. coli K0739377 harboring CMY-43 (lane C2), TEM type (lane A1), and BER (EC2, KL, AmpC-10) type (lane C2). (16) E. coli TOPCMY043 harboring CMY-43 (lane C2) and BER (EC2, KL, AmpC-10) type (lane C2). (17) E. coli CSH-2 harboring MOX-1 (lane C2), TEM type (lane A1), SHV type (lane A1), and MIR (ACT, CHE, GC1, AmpC-3) type (lane C1). (18) E. coli J53-2R(+) harboring FOX-3 (lane C2) [In addition, TEM type (lane A1) and BER (EC2, KL, AmpC-10) type (lane C2) were newly detected by bla detection method]. (19) E. coli BER harboring BER (lane C2). (20) E. coli 520R harboring 520R (lane C2) and BER (EC2, KL, AmpC-10) type (lane C2). (21) E. coli TOPEAR01 harboring Earl (lane C2) and BER (EC2, KL, AmpC-10) type (lane C2). (22) E. coli MG1655 harboring BER (EC2, KL, AmpC-10) type (lane C2). (23) E. coli ATCC25922 harboring BER (EC2, KL, AmpC-10) type (lane C2). (24) E. coli TOP10 harboring BER (EC2, KL, AmpC-10) type (lane C2). (25) E. coli DH5α harboring BER (EC2, KL, AmpC-10) type (lane C2). (26) E. coli BL21 (DE3) harboring BER (EC2, KL, AmpC-10) type (lane C2). (27) E. coli HB4 harboring BER (EC2, KL, AmpC-10) type (lane C2). (28) E. coli JF701 harboring BER (EC2, KL, AmpC-10) type (lane C2). (29) E. coli JF703 harboring BER (EC2, KL, AmpC-10) type (lane C2).

FIGS. 3g-1 to 3g-5 show results from multiplex PCR assays for the detection of D1-specific bla genes in positive

(17) or negative (9) control strains. (1) *E. coli* ECZP-1 harboring SHV-12 (lane A1) [In addition, TEM type (lane A1) and BER (EC2, KL, AmpC-10) type (lane C2) were newly detected by bla detection method]. (2) *E. coli* pCCLLimiA harboring IMI-1 (lane A1) and BER (EC2, KL, AmpC-10) type (lane C2). (3) *E. coli* TOPC008 harboring CTX-M-8 (lane A2), TEM type (lane A1), and BER (EC2, KL, AmpC-10) type (lane C2). (4) *E. coli* TOPCAU01 harboring CAU-1 (lane B1), TEM type (lane A1), and BER (EC2, KL, AmpC-10) type (lane C2). (5) *E. coli* TOPGOB01 harboring GOB-1 (lane B2), TEM type (lane A1), and BER (EC2, KL, AmpC-10) type (lane C2). (6) *E. coli* TOPADC002 harboring ADC-2 (lane C1), TEM type (lane A1), and BER (EC2, KL, AmpC-10) type (lane C2). (7) *E. coli* TOPCMY043 harboring CMY-43 (lane C2) and BER (EC2, KL, AmpC-10) type (lane C2). (8) *E. coli* DH5α harboring BER (EC2, KL, AmpC-10) type (lane C2). (9) *E. coli* TOPDXA211 harboring OXA-211 (lane D2), TEM type (lane A1), and BER (EC2, KL, AmpC-10) type (lane C2). (10) *P. aeruginosa* 08PAE4 harboring OXA-2 (lane D1), TEM type (lane A1), MIR (ACT, CHE, GC1, AmpC-3) type (lane C1), and CMY-1 (MOX, FOX, AmpC-9) type (lane C2). (11) *P. aeruginosa* 08PAE8 harboring OXA-2 (lane D1) and MIR (ACT, CHE, GC1, AmpC-3) type (lane C1). (12) *E. coli* TOP0002 harboring OXA-2 (lane D1) and BER (EC2, KL, AmpC-10) type (lane C2). (13) *P. aeruginosa* 08PAE32 harboring OXA-10 (lane D1), VIM type (lane B1), MIR (ACT, CHE, GC1, AmpC-3) type (lane C1), and OXA-23 type (lane D1). (14) *P. aeruginosa* WK20 harboring OXA-10 (lane D1) and MIR (ACT, CHE, GC1, AmpC-3) type (lane C1). (15) *E. coli* TOP010 harboring OXA-10 (lane D1) and BER (EC2, KL, AmpC-10) type (lane C2). (16) *A. baumannii* AB4-1 harboring OXA-21 (lane D1), TEM type (lane A1), ADC (AmpC-5) type (lane C1), and OXA-10 type (lane D1). (17) *A. baumannii* K0420859 harboring OXA-23 (lane D1) [In addition, ADC (AmpC-5) type (lane C1) and OXA-10 type (lane D1) were newly detected by bla detection method]. (18) *E. coli* TOPDXA031 harboring OXA-31 (lane D1), TEM type (lane A1), and BER (EC2, KL, AmpC-10) type (lane C2). (19) *E. coli* TOPDXA040 harboring OXA-40 (lane D1), TEM type (lane A1), and BER (EC2, KL, AmpC-10) type (lane C2). (20) *E. coli* TOPDXA042 harboring OXA-42 (lane D1), TEM type (lane A1), and BER (EC2, KL, AmpC-10) type (lane C2). (21) *E. coli* TOPDXA063 harboring OXA-63 (lane D1), TEM type (lane A1), and BER (EC2, KL, AmpC-10) type (lane C2). (22) *E. coli* TOPDXA069 harboring OXA-69 (lane D1), TEM type (lane A1), and BER (EC2, KL, AmpC-10) type (lane C2). (23) *P. aeruginosa* PAE0831 harboring OXA-210 (lane D1) and AmpCCARBA-2 type (lane C1). (24) *E. coli* TOPO210 harboring OXA-210 (lane D1) and BER (EC2, KL, AmpC-10) type (lane C2). (25) *P. aeruginosa* WK28 harboring OXA-240 (lane D1) and AmpCCARBA-2 type (lane C1). (26) *E. coli* TOPO240 harboring OXA-240 (lane D1) and BER (EC2, KL, AmpC-10) type (lane C2).

Figure 1:
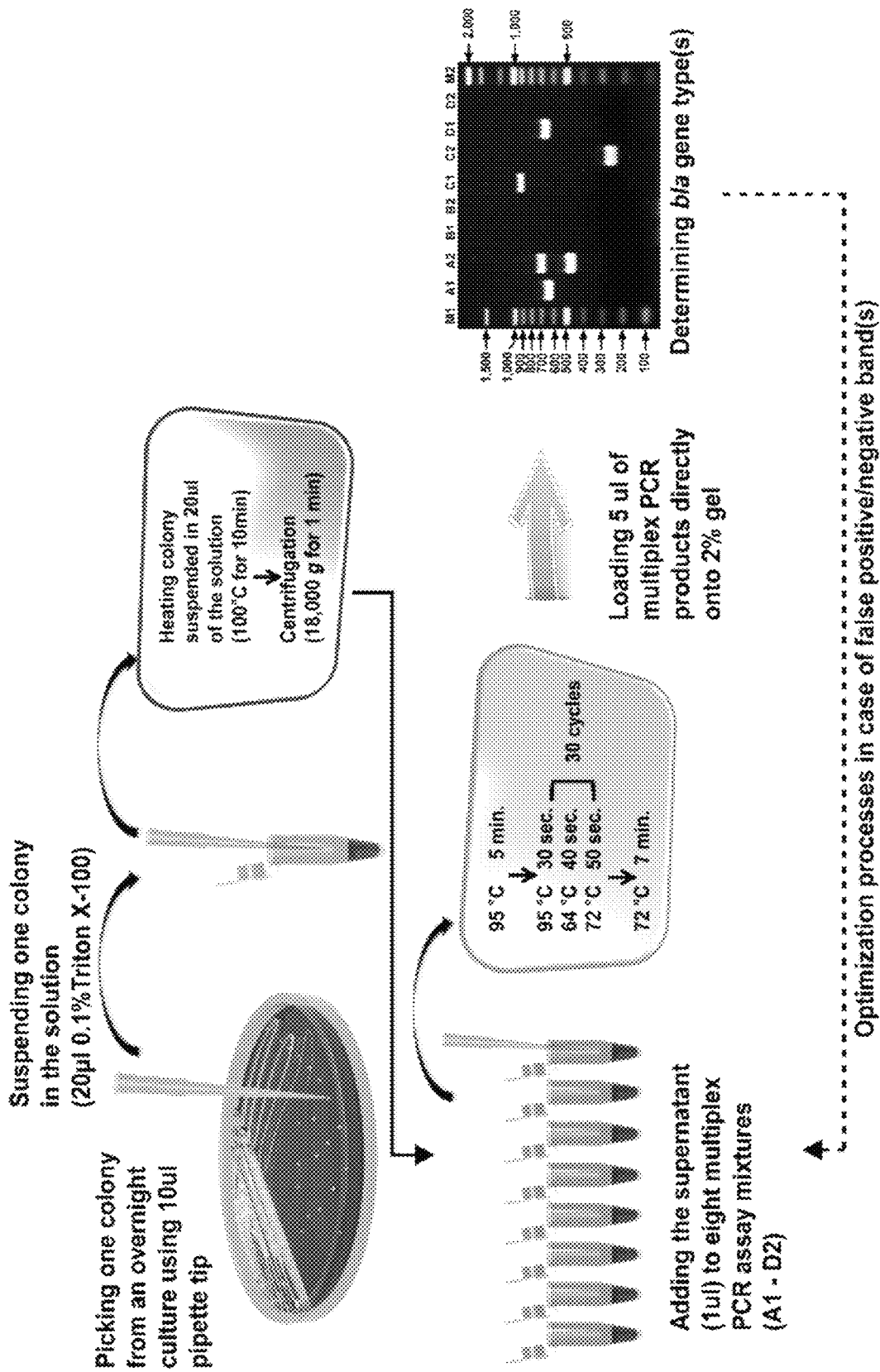
FIG. 1 shows the large-scale bla detection method (LARGE-SCALEblaFinder) using a single colony. A single colony from an overnight culture was suspended in the solution containing 0.1% Triton X-100, immediately followed by heating of the cell suspension at 100° C. for 10 min. After removing cellular debris by a centrifugation step at 18,000×g for 1 min, the supernatant (1 μl, template) was subjected to a multiplex PCR with eight multiplex PCR tubes (A1, A2, B1, B2, C1, C2, D1, and D2). 34 μl reaction mixture of each multiplex PCR tube contained 1×DiaStar™ Multiplex PCR Smart mix and 0.2 μM bla type-specific primers (e.g., 16 primers in case of the multiplex PCR tube A1, Table 1). All amplifications in eight multiplex PCR tubes were performed with the identical and following thermal cycling condition: initial denaturation at 95° C. for 5 min; 30 cycles of 95° C. for 30 sec, 64° C. for 40 sec, and 72° C. 50 sec; and a final elongation step at 72° C. for 7 min. All multiplex PCR products (5 μl) were separated in a 2% agarose gel. Each bla gene type was determined by comparing each band size on agarose gels with the corresponding size shown in FIGS. 2a to 2h (or the corresponding amplicon size of Table 1). In case of false positive and/or negative band(s), optimization processes of 54 primer pairs were performed through our novel and unique method.
Figure 2A:
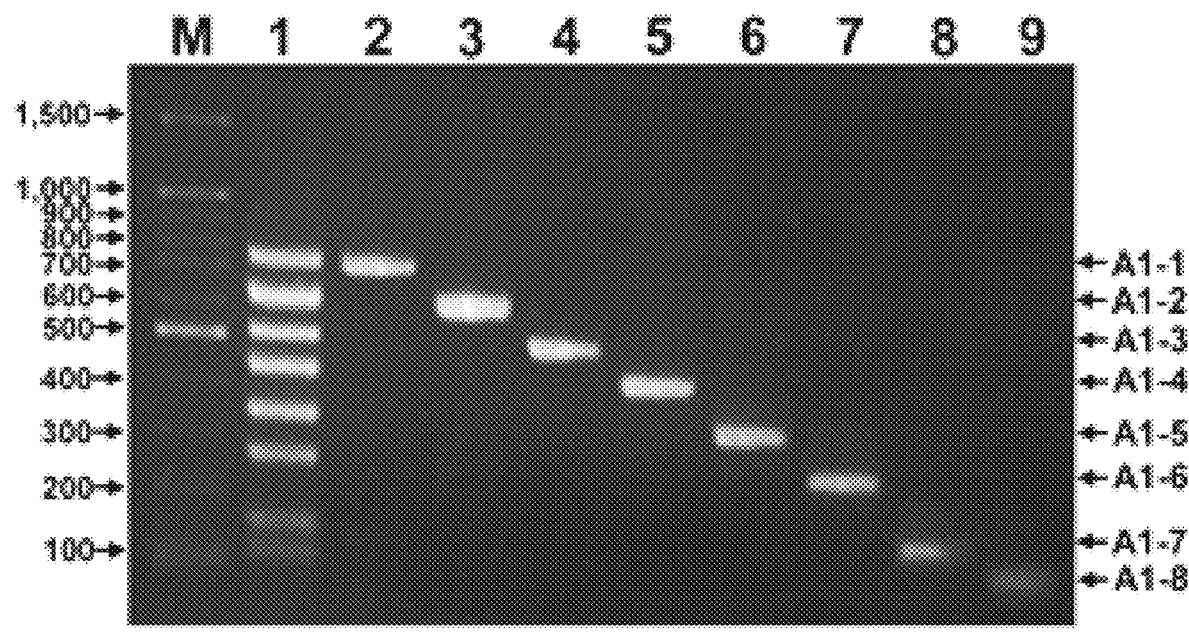
FIGS. 2a to 2h show the validation of primer pairs by simplex and multiplex PCR assays. To confirm whether primer pairs can correctly amplify their respective loci, primer pairs were evaluated in simplex and multiplex PCR assays. The supernatant obtained from a single colony (FIG. 1) with each bla gene type was used as a template. The supernatants were obtained from 54 representative and positive control strains harboring 54 bla gene types, respectively. Each (expected) size of 54 type-specific bla PCR products (A1-1~D2-7) was shown in the Table 1. Results from optimized multiplex PCR assays in 100 (including above 54) positive control strains were shown in FIGS. 3a-1 to 3h-3. Multiplex (lane 1) and simplex (lanes other than 1) PCR products were separated in a 2% agarose gel. Direct sequencing of all PCR products in 54 simplex and eight multiplex PCRs confirmed the exact detection of 54 bla gene types. Lane M is a molecular size marker. (a) Templates of multiplex and simplex PCRs for the detection of A1-specific bla genes are as follows: lane 1, eight templates used in lanes 2-9; lane 2, GES-5 from K. pneumoniae CHAK36; lane 3, TEM-30 from E. coli CF0022; lane 4, IMI-1 from E. coli pCCLLimiA; lane 5, KPC-3 from K. pneumoniae CL5761; lane 6, SHV-2a from E. coli ECLA-4; lane 7, VEB-2 from E. coli TOPVEB02; lane 8, PER-2 from E. coli TOPPER02; lane 9, SME-1 from E. coli TOPSME01. (b) Templates of multiplex and simplex PCRs for the detection of A2-specific bla genes are as follows: lane 1, five templates used in lanes 2-6; lane 2, CTX-M-27 from E. coli TOPC027; lane 3, CTX-M-114 from P. rettgeri PS022; lane 4, CTX-M-25 from E. coli TOPC025; lane 5, CTX-M-43 from E. coli TOPC043; lane 6, CTX-M-8 from E. coli TOPC008. (c) Templates of multiplex and simplex PCRs for the detection of B1-specific bla genes are as follows: lane 1, eight templates used in lanes 2-9; lane 2, THIN-B from E. coli TOPTHINB; lane 3, CAU-1 from E. coli TOPCAU01; lane 4, SIM-1 from E. coli TOPSIM01; lane 5, CphA from E. coli TOPCPHA; lane 6, IND-6 from E. coli TOPIND06; lane 7, IMP-1 from E. coli JAEE1; lane 8, NDM-1 from E. coli TOPNDM01; lane 9, VIM-2 from C. freundii 11-7F4560. (d) Templates of multiplex and simplex PCRs for the detection of B2-specific bla genes are as follows: lane 1, eight templates used in lanes 2-9; lane 2, AIM-1 from E. coli TOPAIM01; lane 3, KHM-1 from E. coli TOPKHM01; lane 4, FEZ-1 from E. coli TOPFEZ01; lane 5, GOB-1 from E. coli TOPGOB01; lane 6, BlaB-1 from E. coli TOPBLAB01; lane 7, SPM-1 from E. coli TOPSPM01; lane 8, EBR-1 from E. coli TOPEBR01; lane 9, JOHN-1 from E. coli TOPJOHN01. (e) Templates of multiplex and simplex PCRs for the detection of C1-specific bla genes are as follows: lane 1, five templates used in lanes 2-6; lane 2, ACC-4 from E. coli TOPACC04; lane 3, DHA-1 from E. coli E07-39524; lane 4, MIR-1 from E. coli C600; lane 5, PDC-3 from E. coli TOPPDC03; lane 6, ADC-2 from E. coli TOPADC002. (f) Templates of multiplex and simplex PCRs for the detection of C2-specific bla genes are as follows: lane 1, five templates used in lanes 2-6; lane 2, CMY-3 from E. coli JM109; lane 3, Earl from E. coli TOPEAR01; lane 4, 520R from E. coli 520R; lane 5, CMY-10 from E. aerogenes K9911729; lane 6, BER from E. coli BER. (g) Templates of multiplex and simplex PCRs for the detection of D1-specific bla genes are as follows: lane 1, eight templates used in lanes 2-9; lane 2, OXA-23 from A. baumannii K0420859; lane 3, OXA-2 from P. aeruginosa 08PAE4; lane 4, OXA-10 from P. aeruginosa WK20; lane 5, OXA-69 from E. coli TOPDXA069; lane 6, OXA-31 from E. coli TOPDXA031; lane 7, OXA-40 from E. coli TOPDXA040; lane 8, OXA-63 from E. coli TOPDXA063; lane 9, OXA-42 from E. coli TOPDXA042. (h) Templates of multiplex and simplex PCRs for the detection of D2-specific bla genes are as follows: lane 1, seven templates used in lanes 2-8; lane 2, OXA-235 from E. coli TOPDXA235; lane 3, OXA-228 from E. coli TOPDXA228; lane 4, OXA-58 from E. coli TOPDXA058; lane 5, OXA-48 from E. coli TOPDXA048; lane 6, OXA-214 from E. coli TOPDXA214; lane 7, OXA-211 from E. coli TOPDXA211; lane 8, OXA-20 from E. coli TOPDXA020.
Figure 2B:
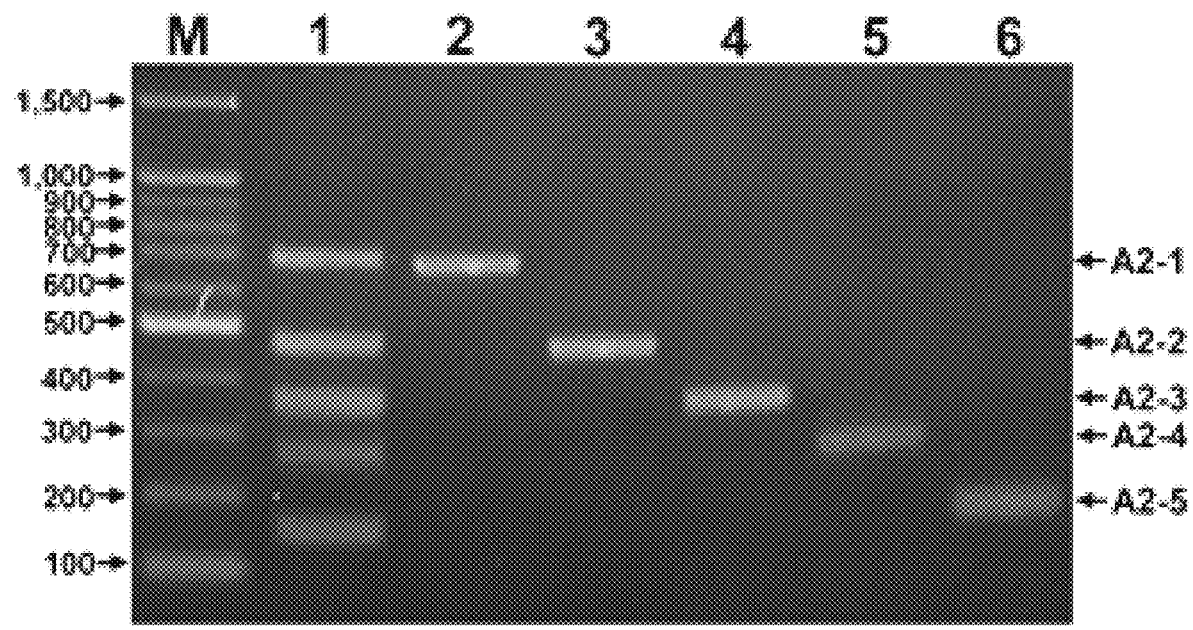
Figure 2C:
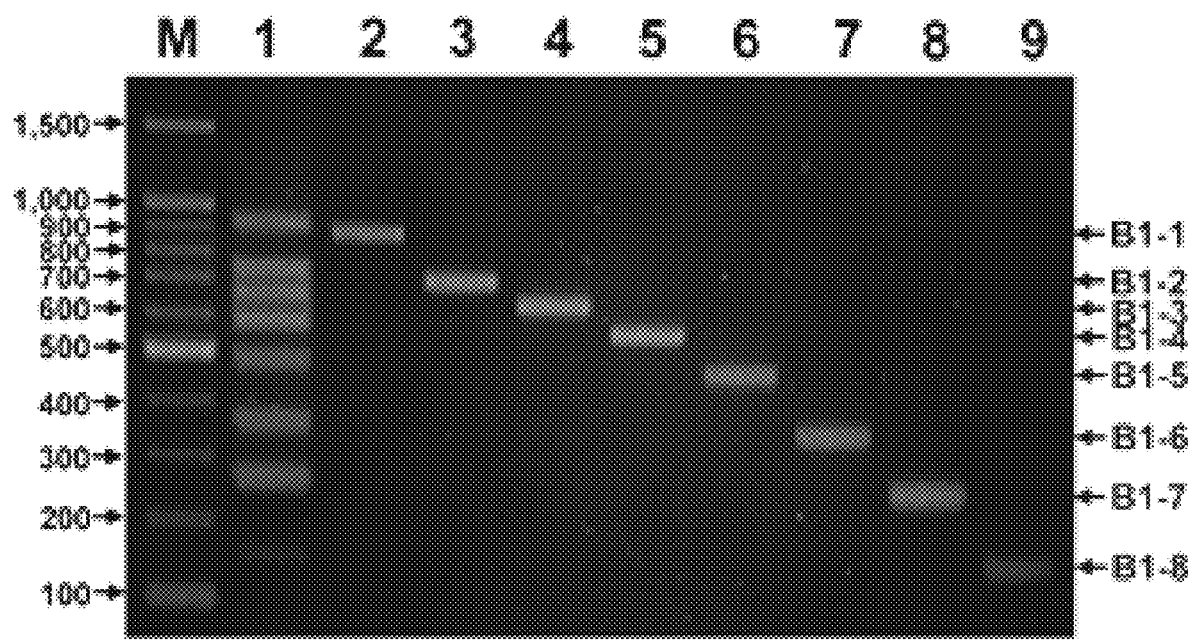
Figure 2D:
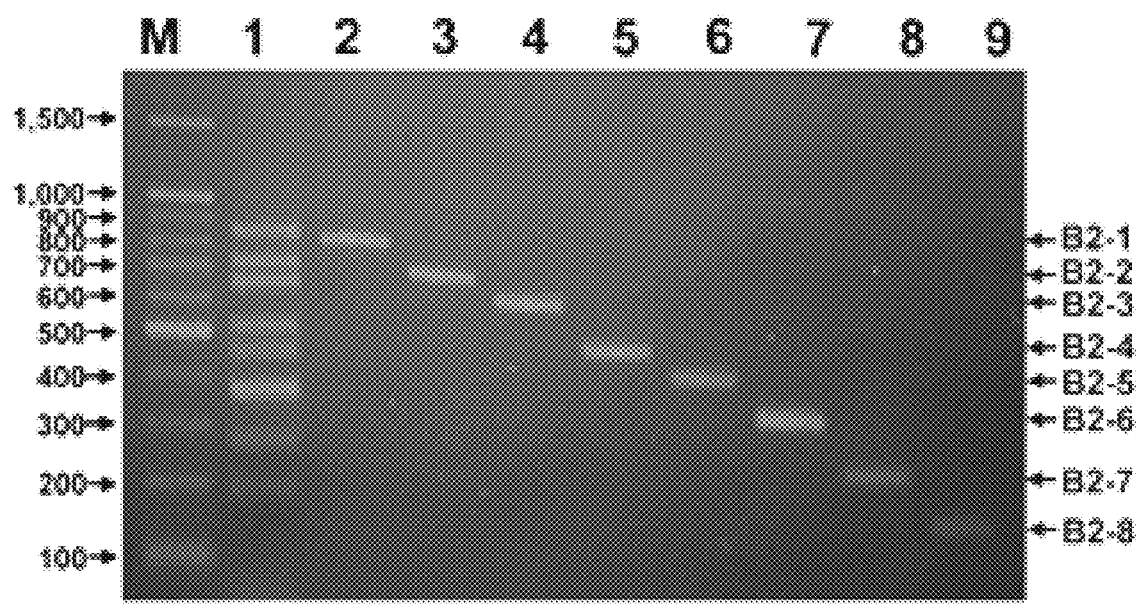
Figure 2E:
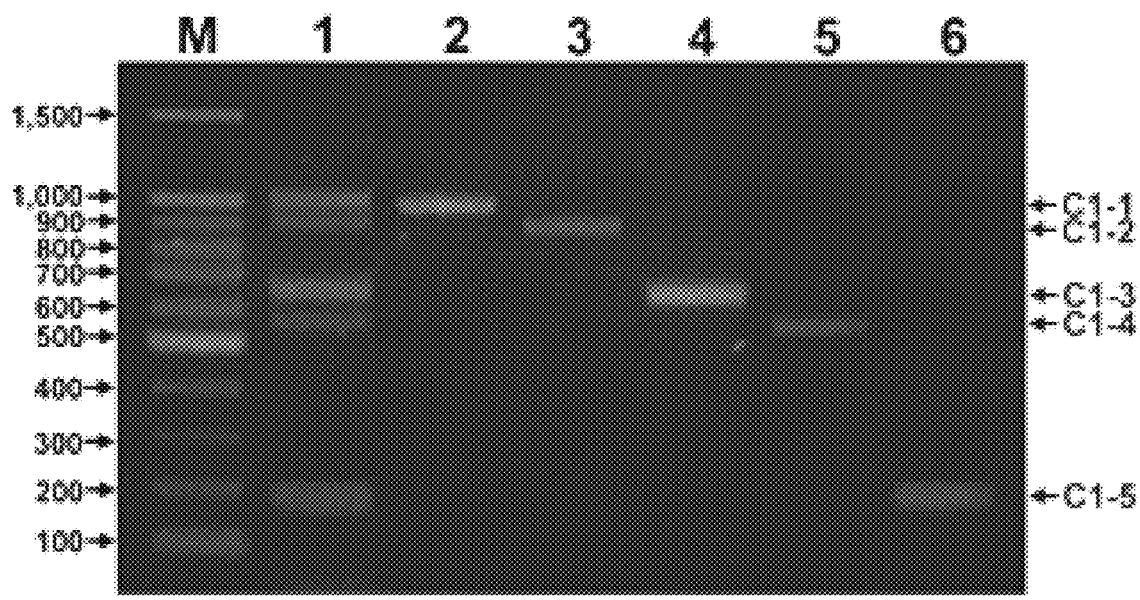
Figure 2F:
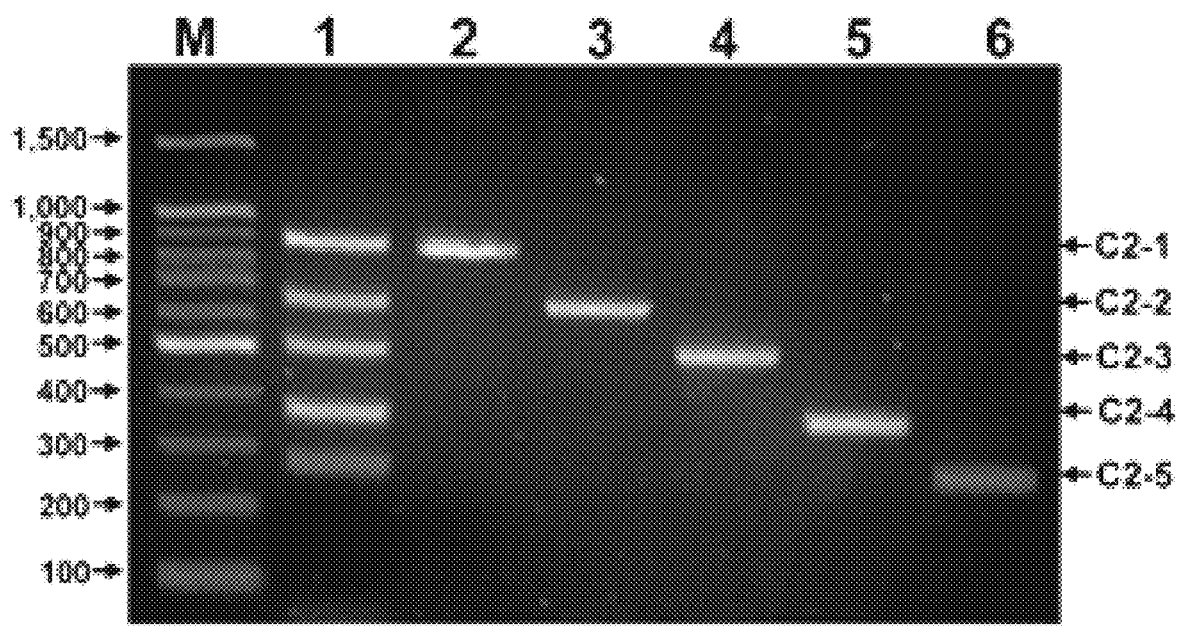
Figure 2G:
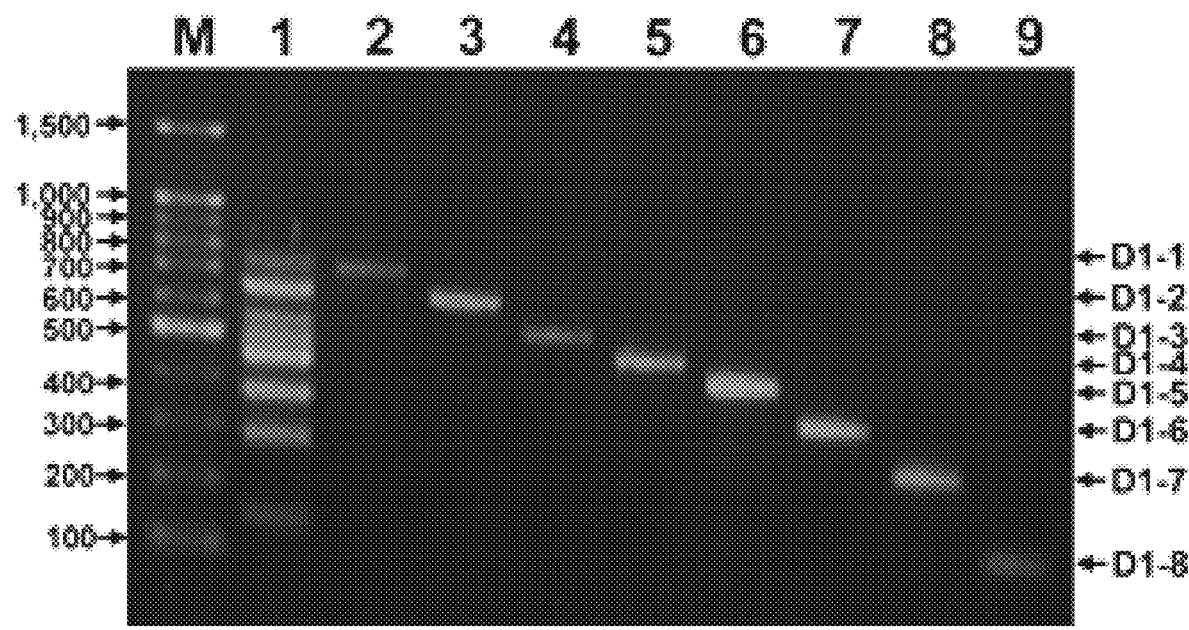
Figure 2H:
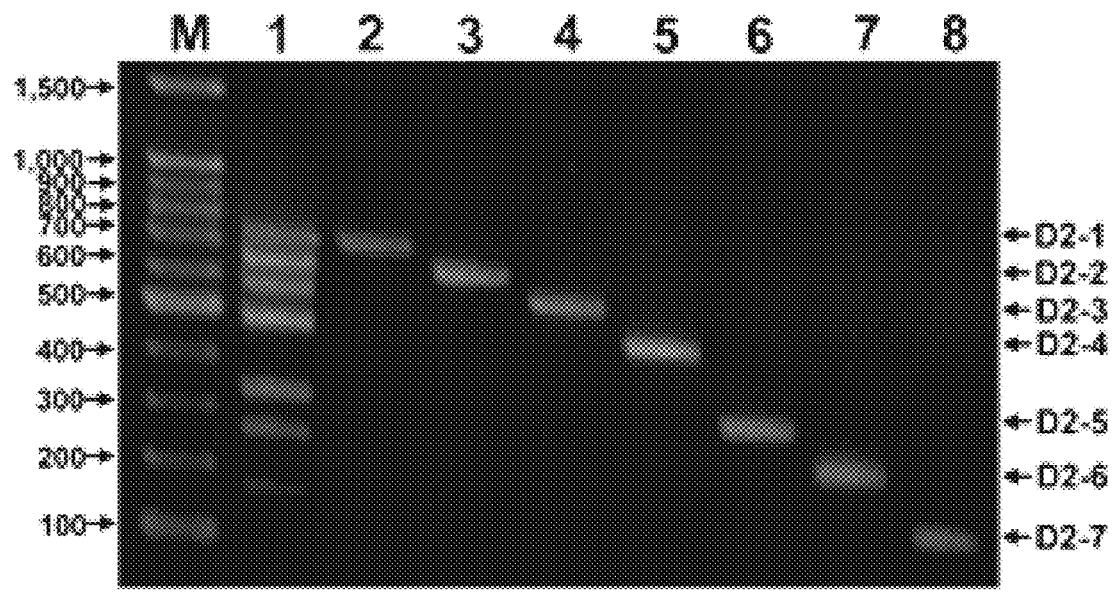
Figures 1, 3A:
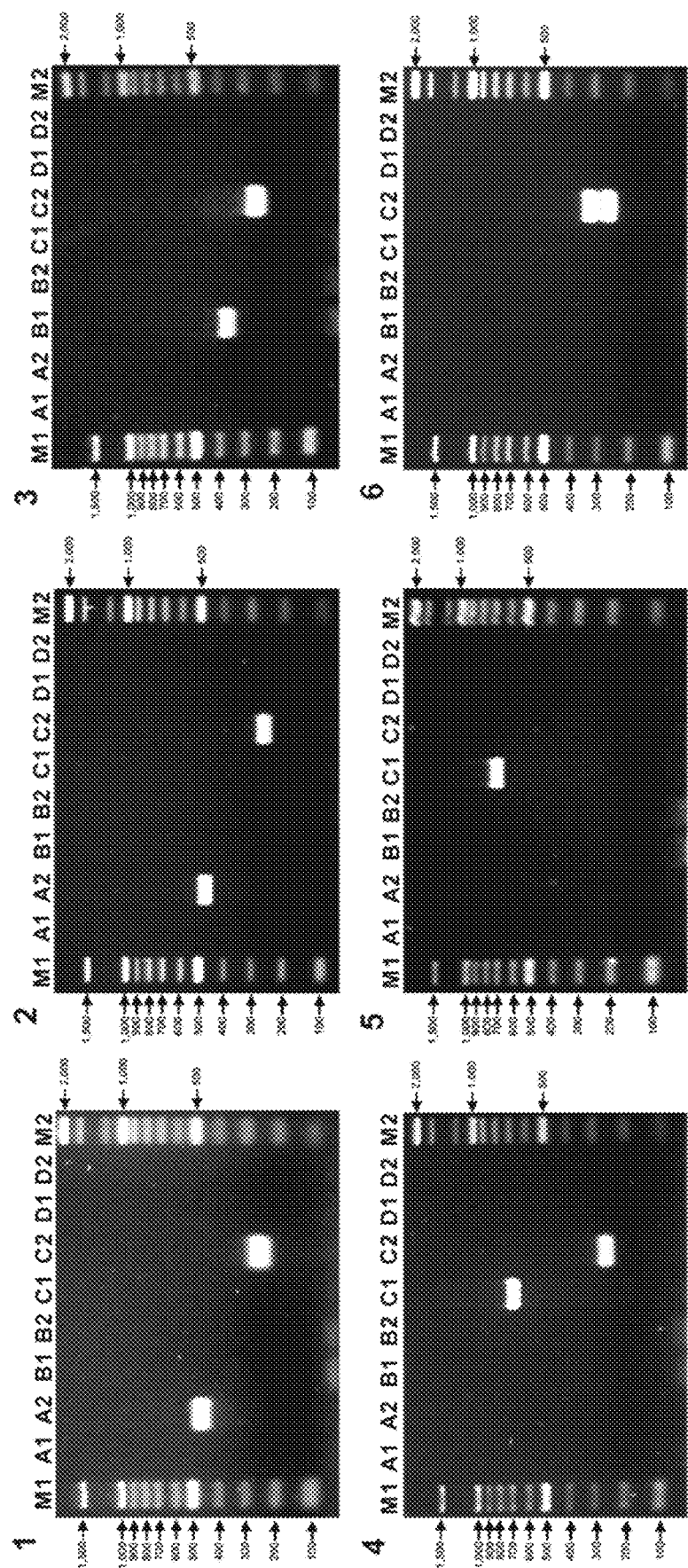
Figures 2, 3A:
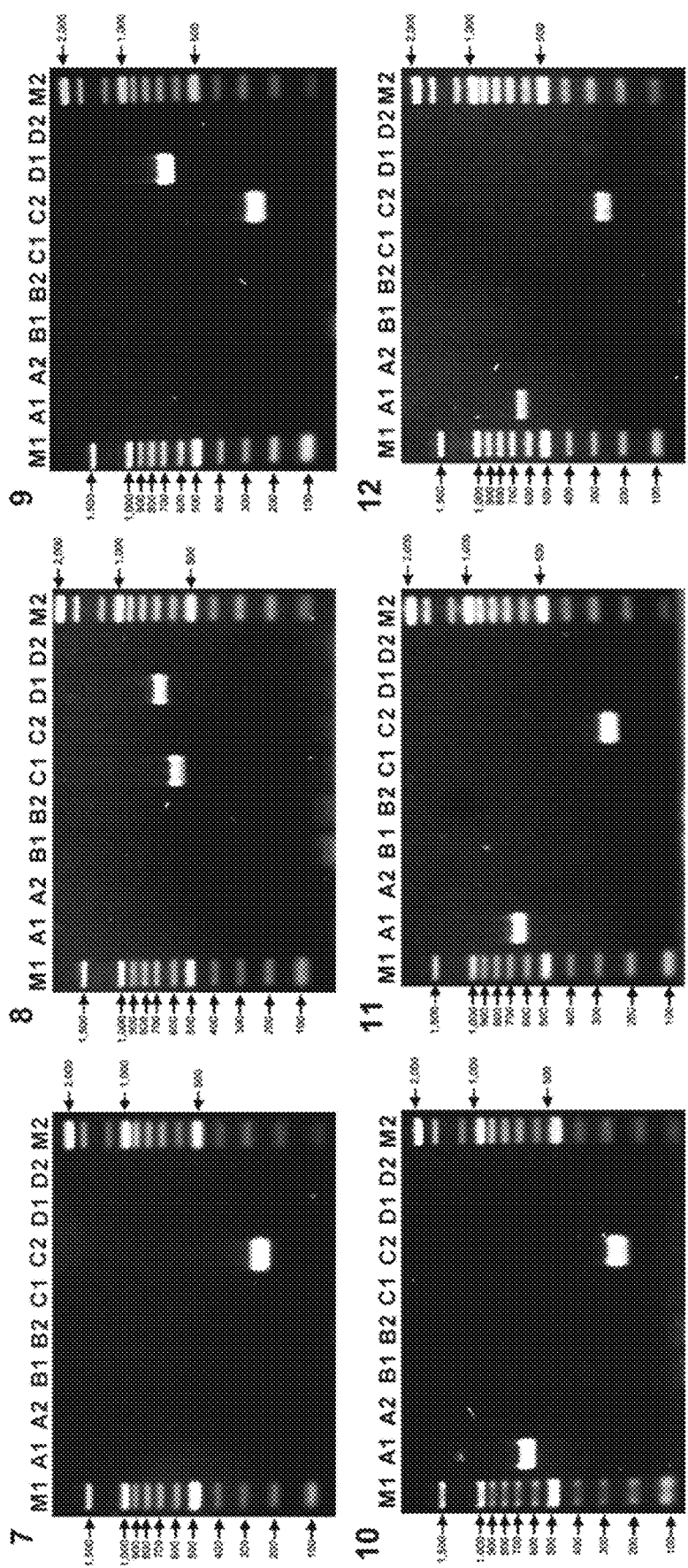
Figures 3, 3A:
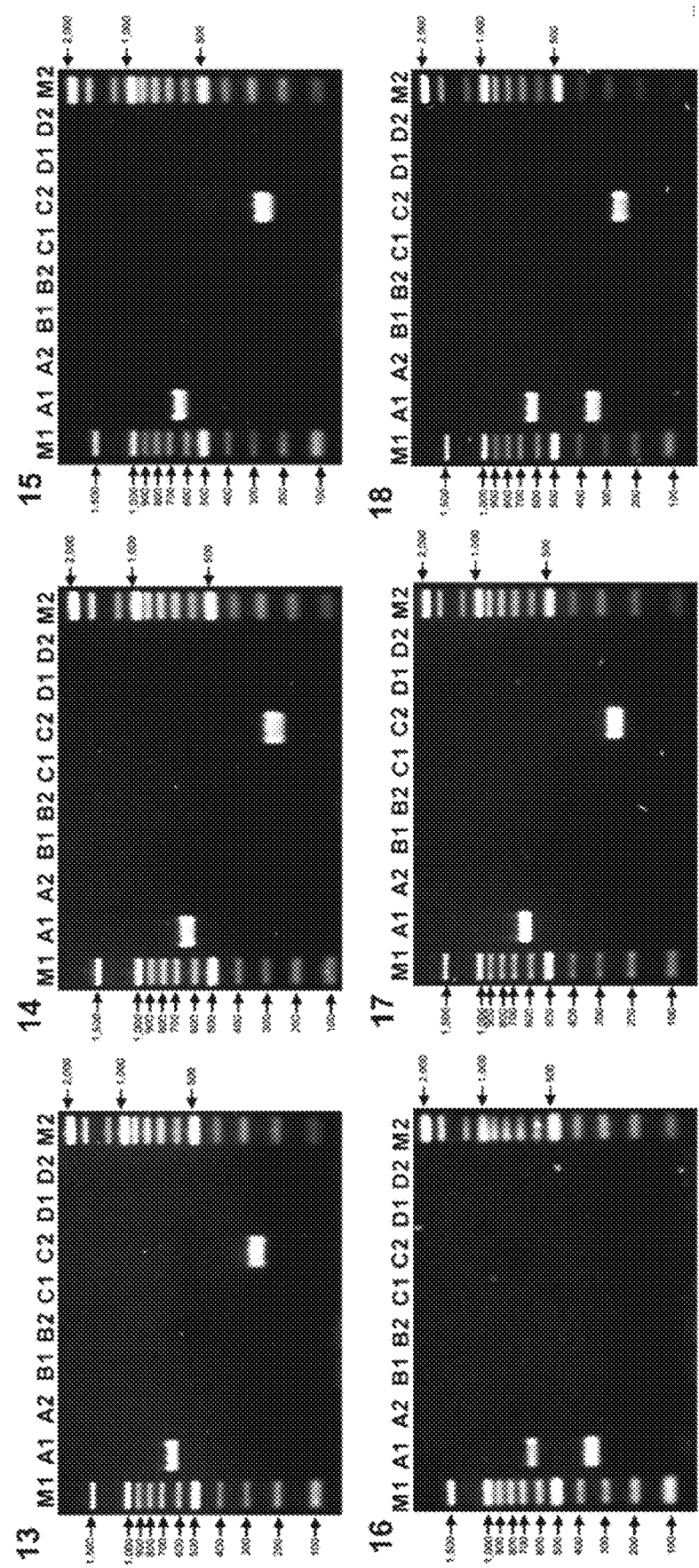
Figures 3, 3A, 4:
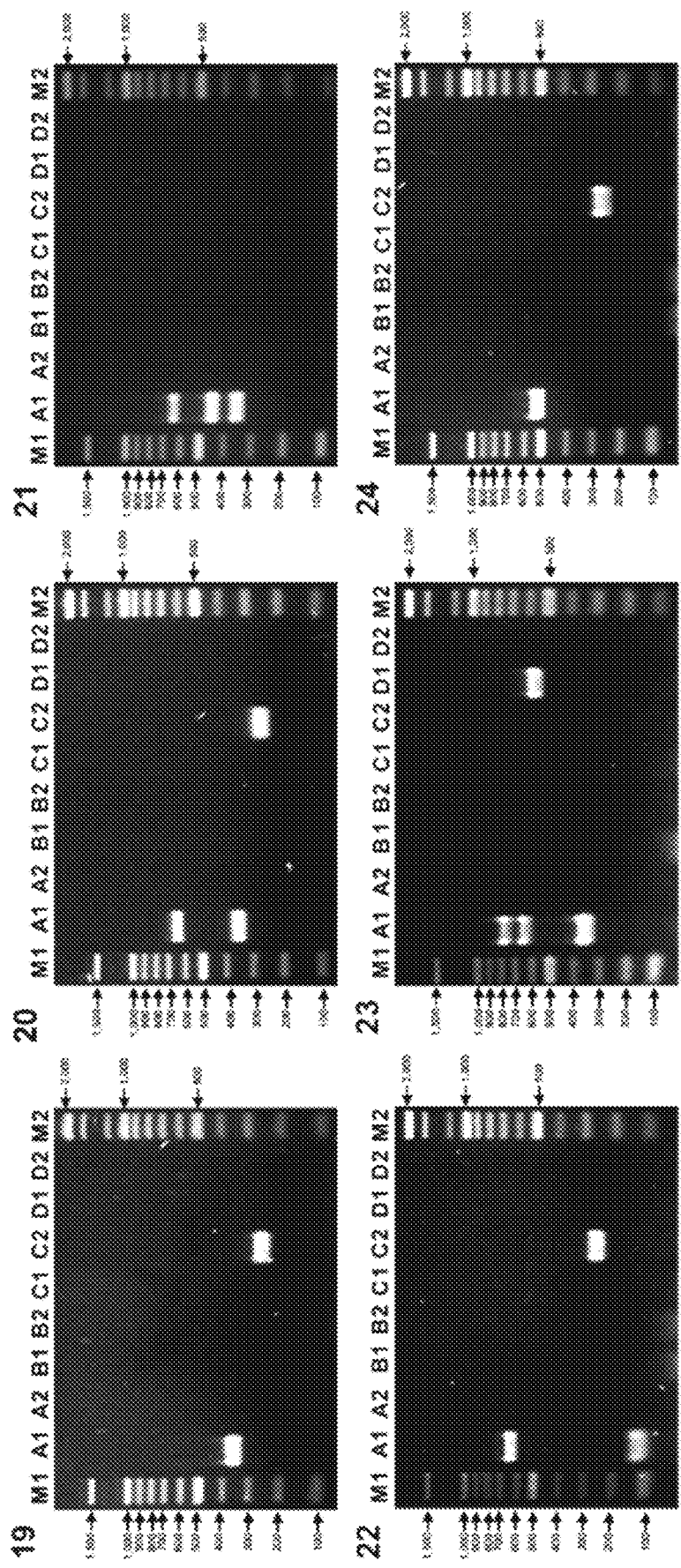
Figures 3, 3A, 4, 5:
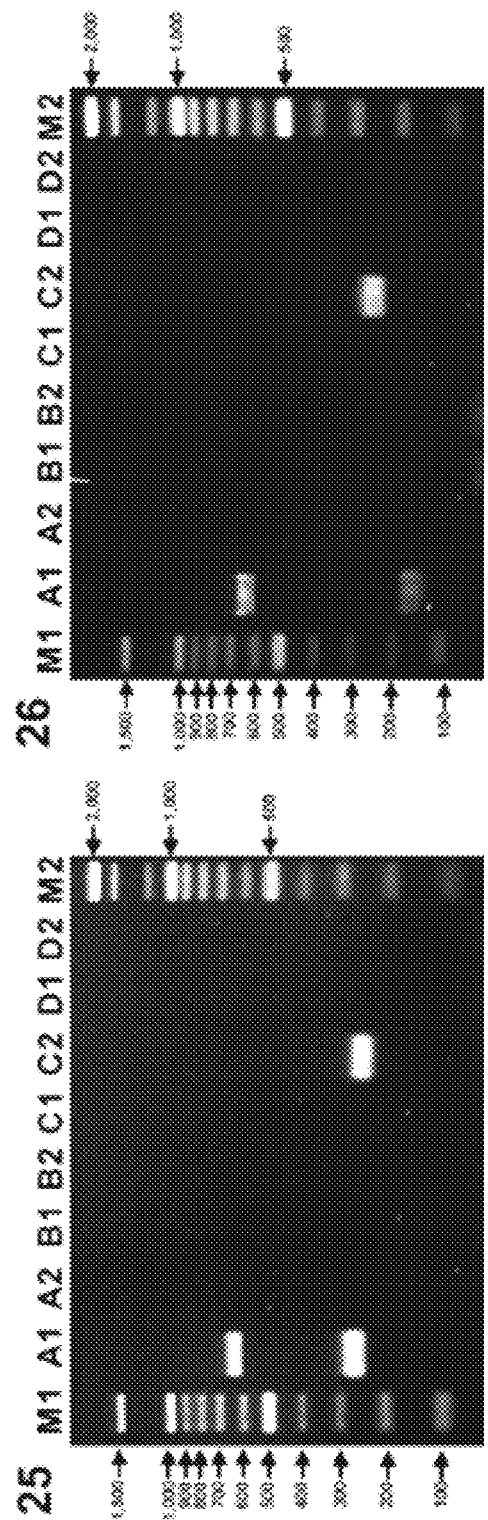
Figures 1, 3B:
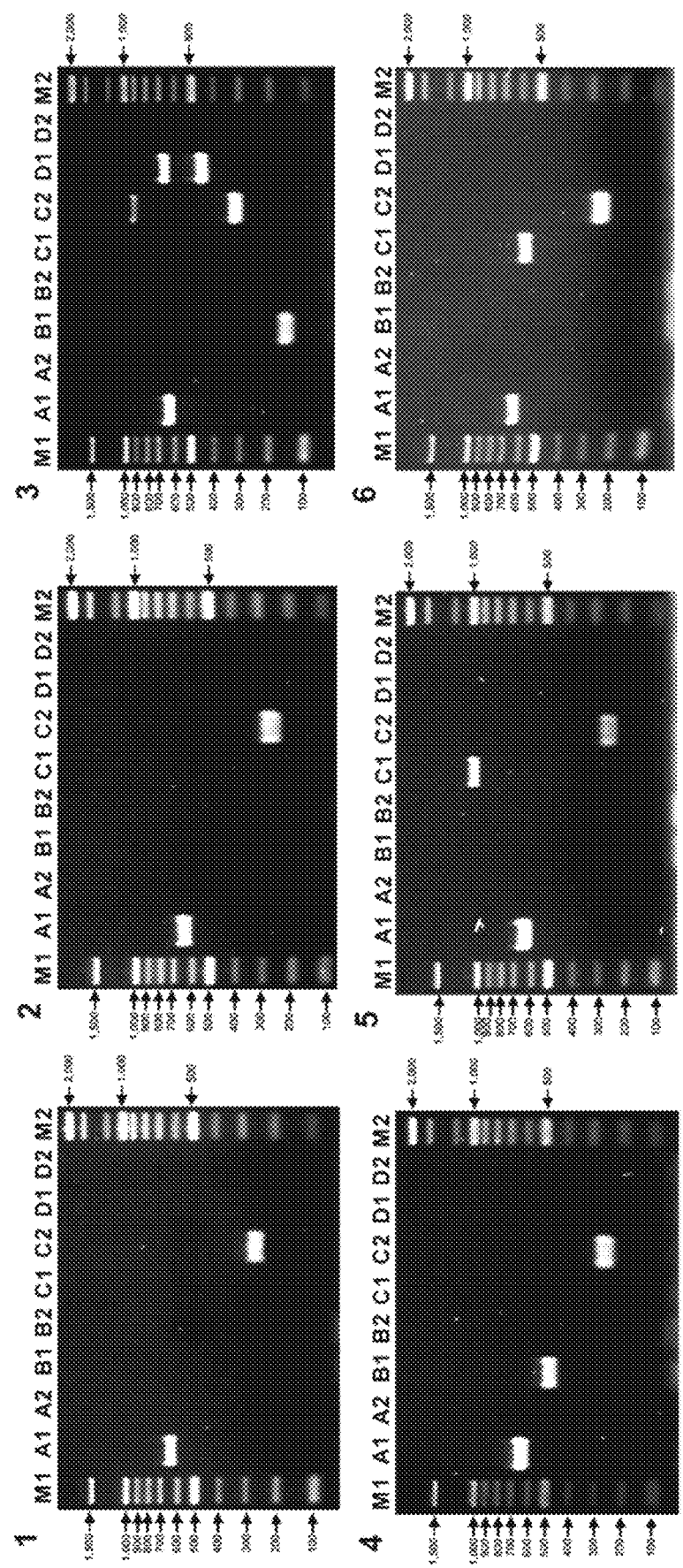
Figures 2, 3B:
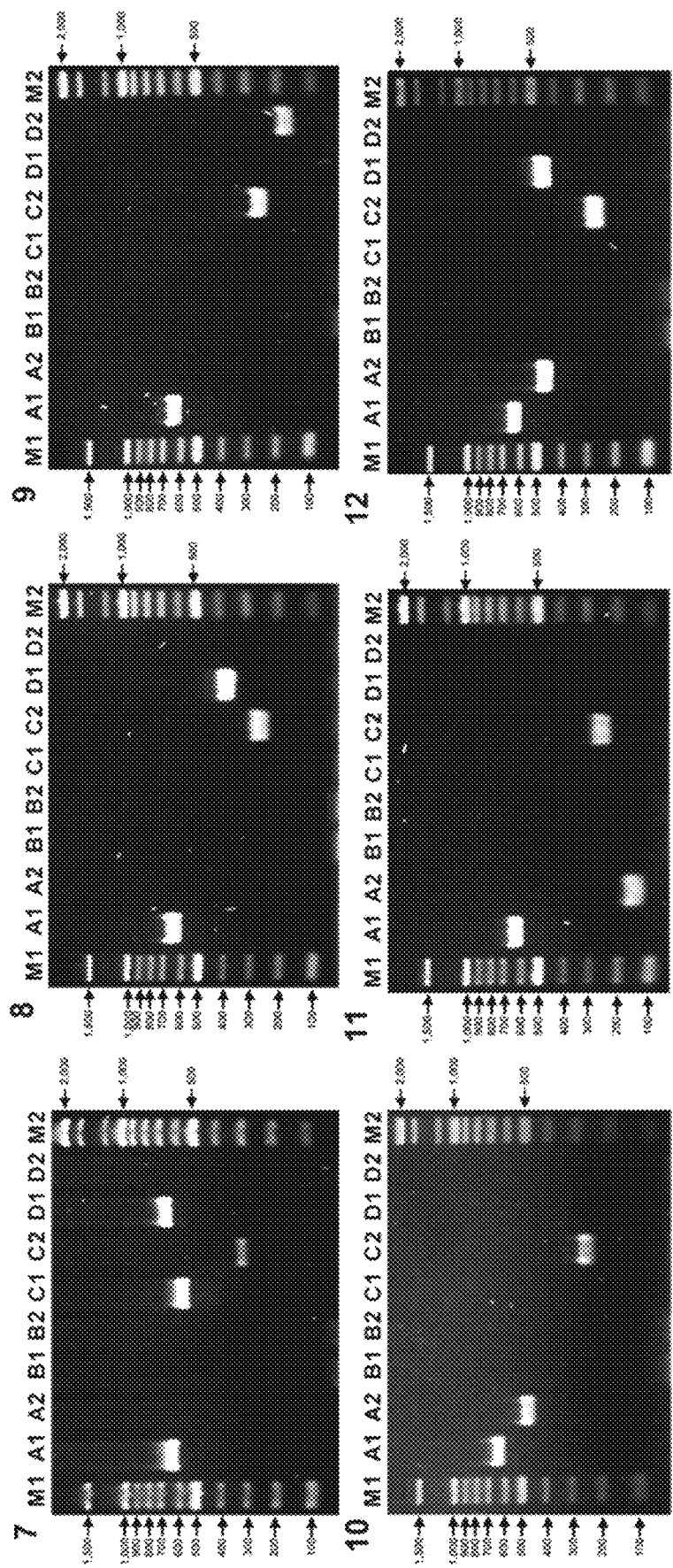
Figures 1, 3C:
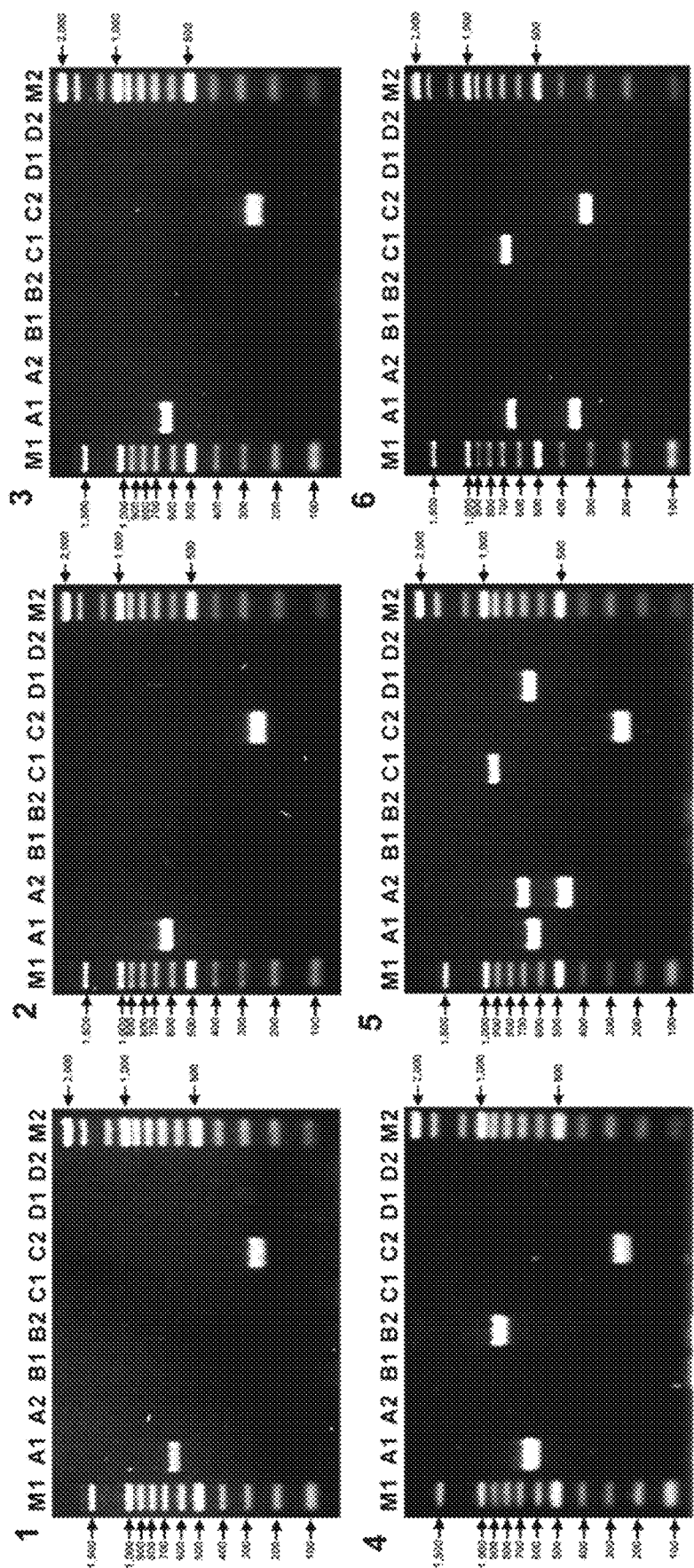
Figures 2, 3C:
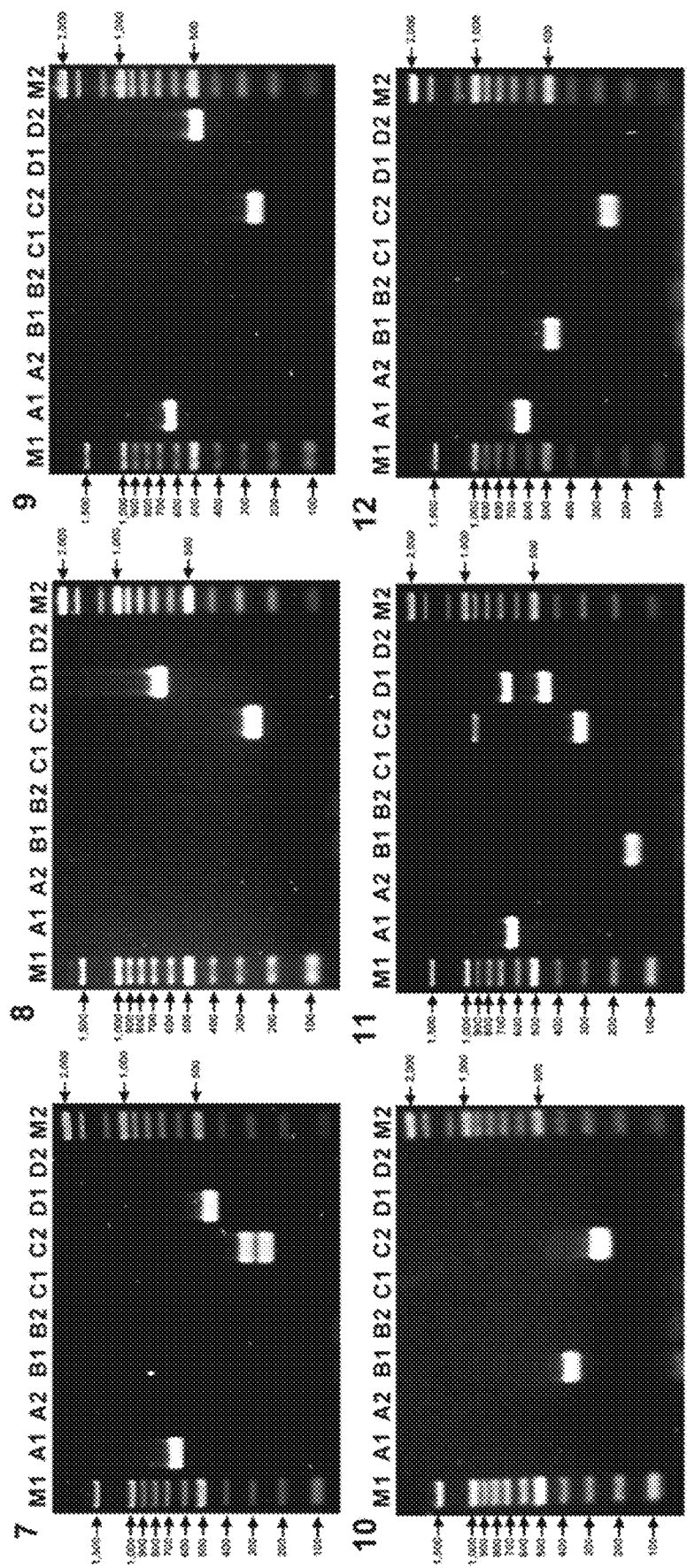
Figures 3, 3C:
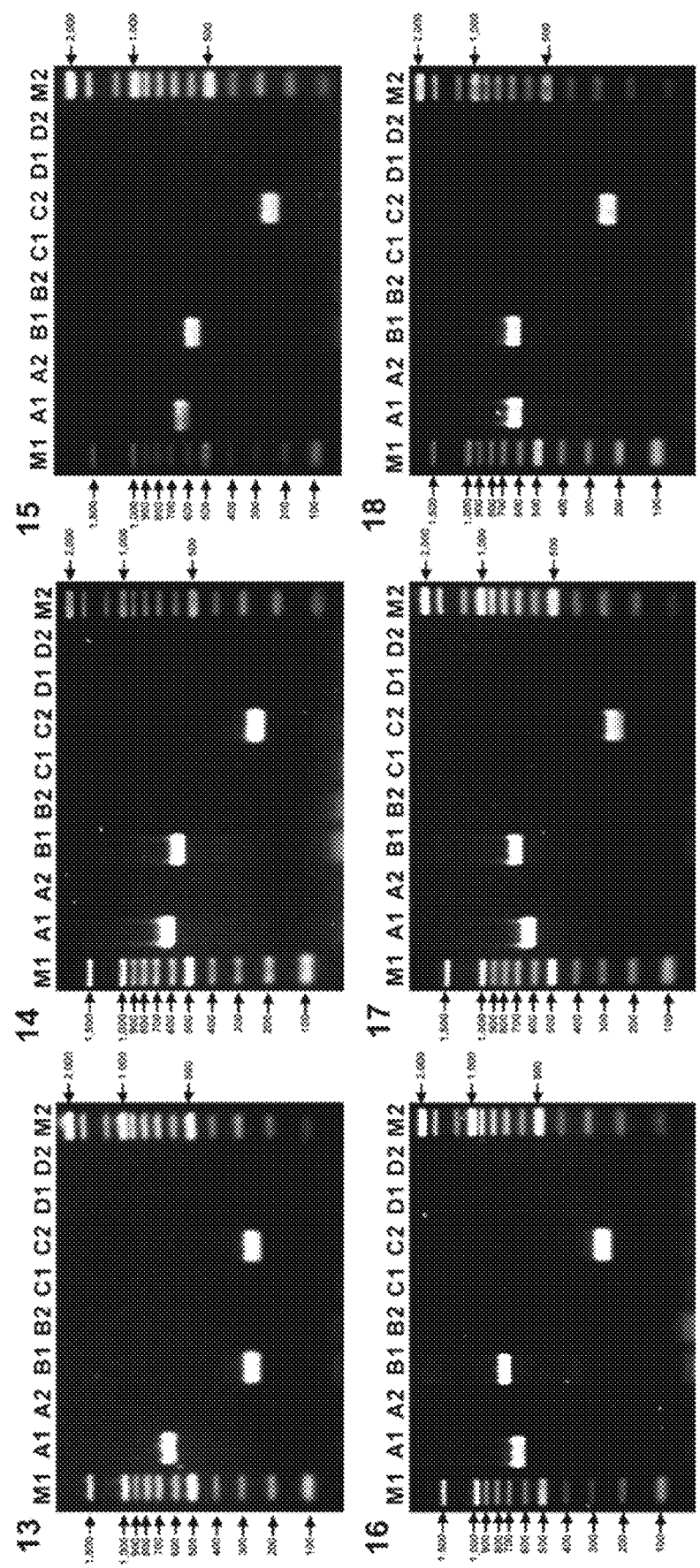
Figures 1, 3D:
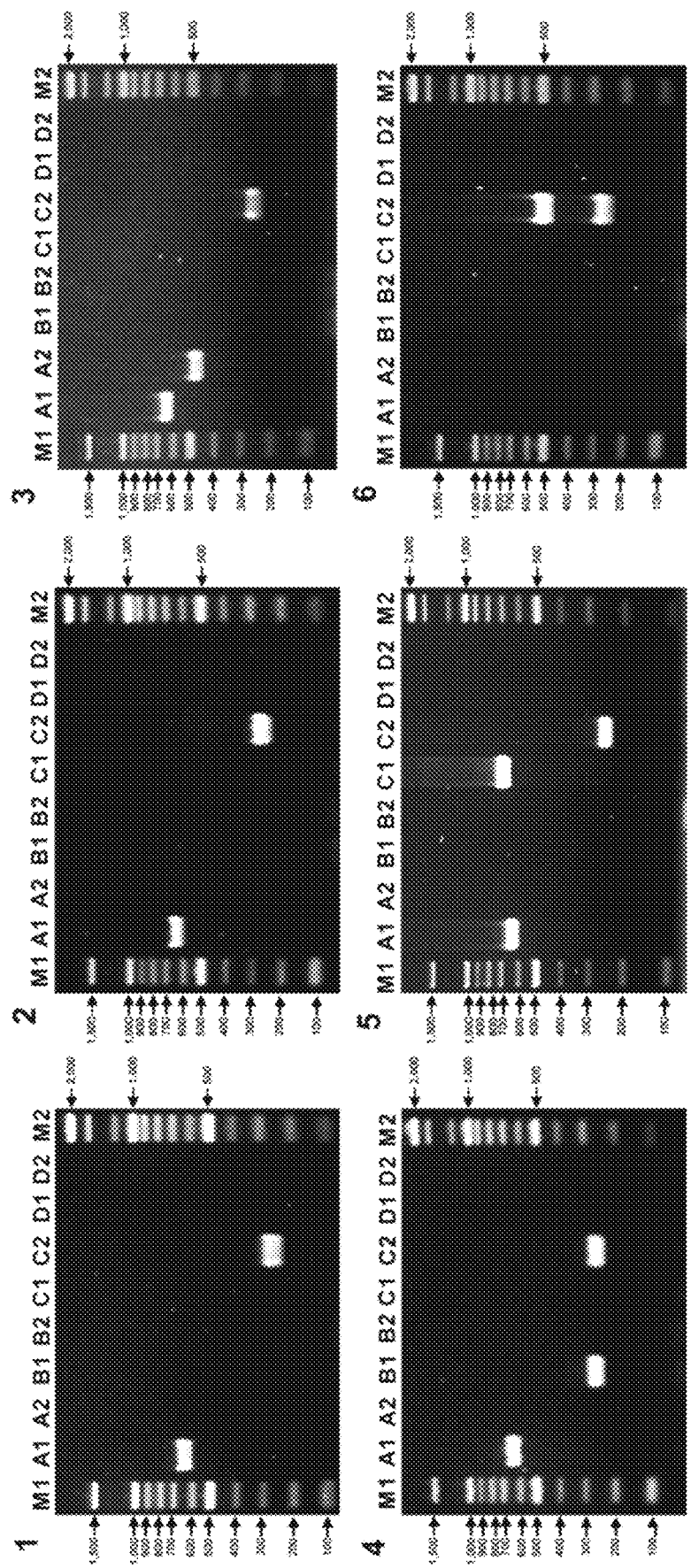
Figures 3, 3D:
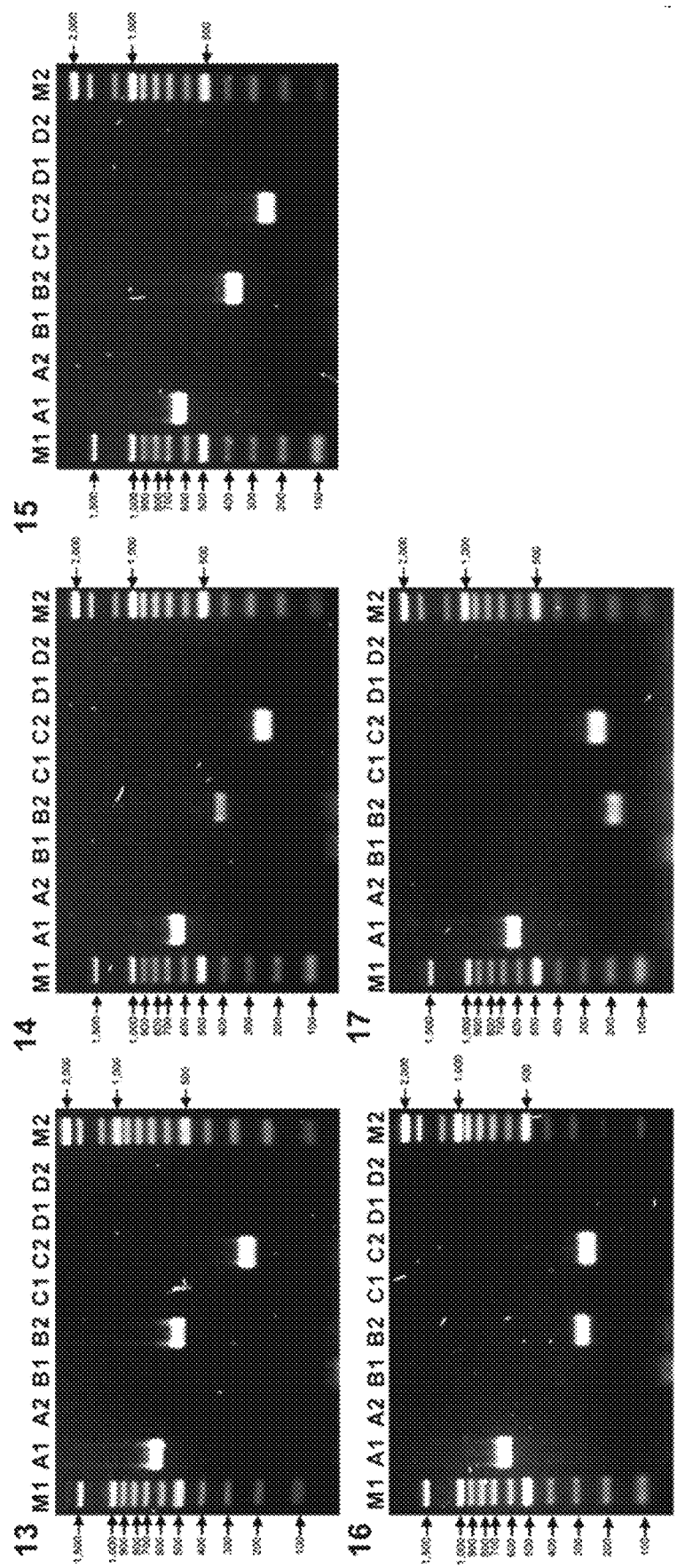
Figures 1, 3E:
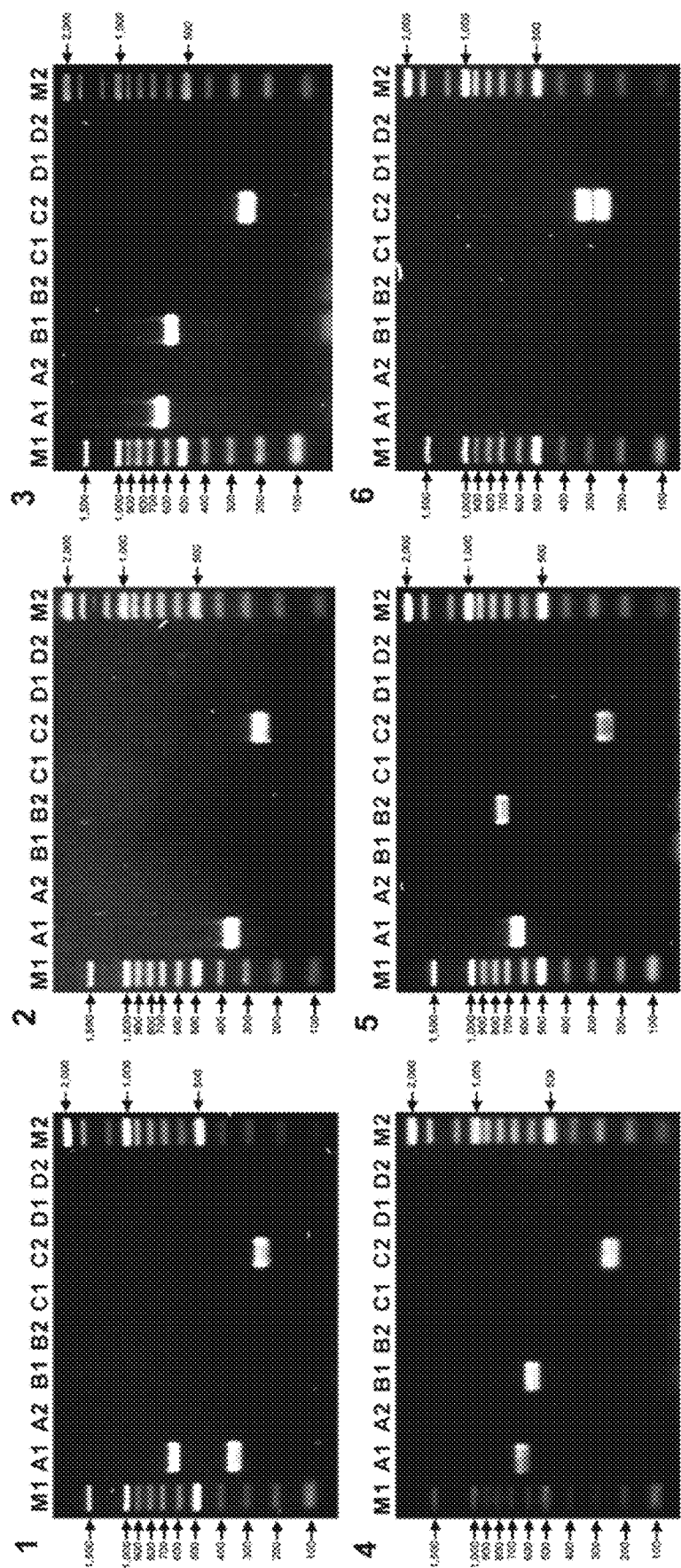
Figures 2, 3E:
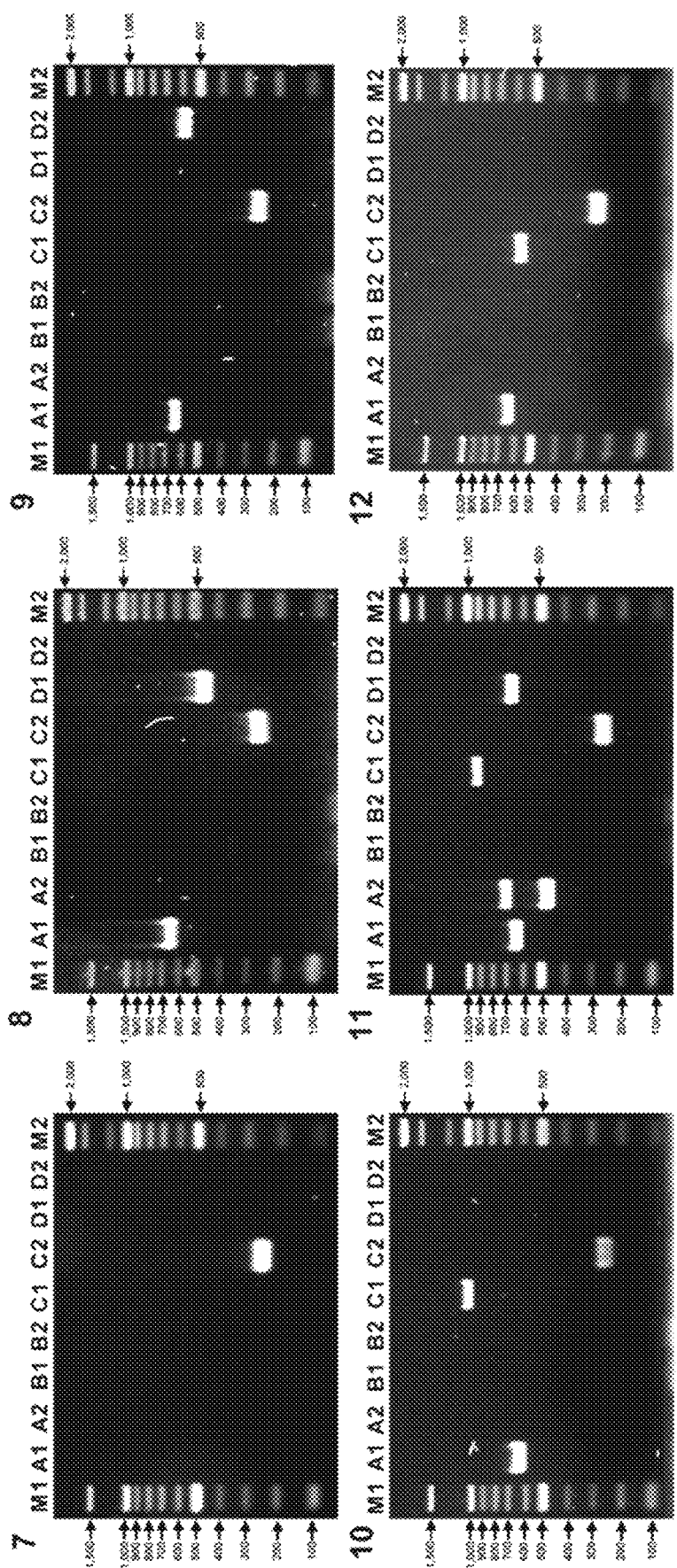
Figures 3, 3E:
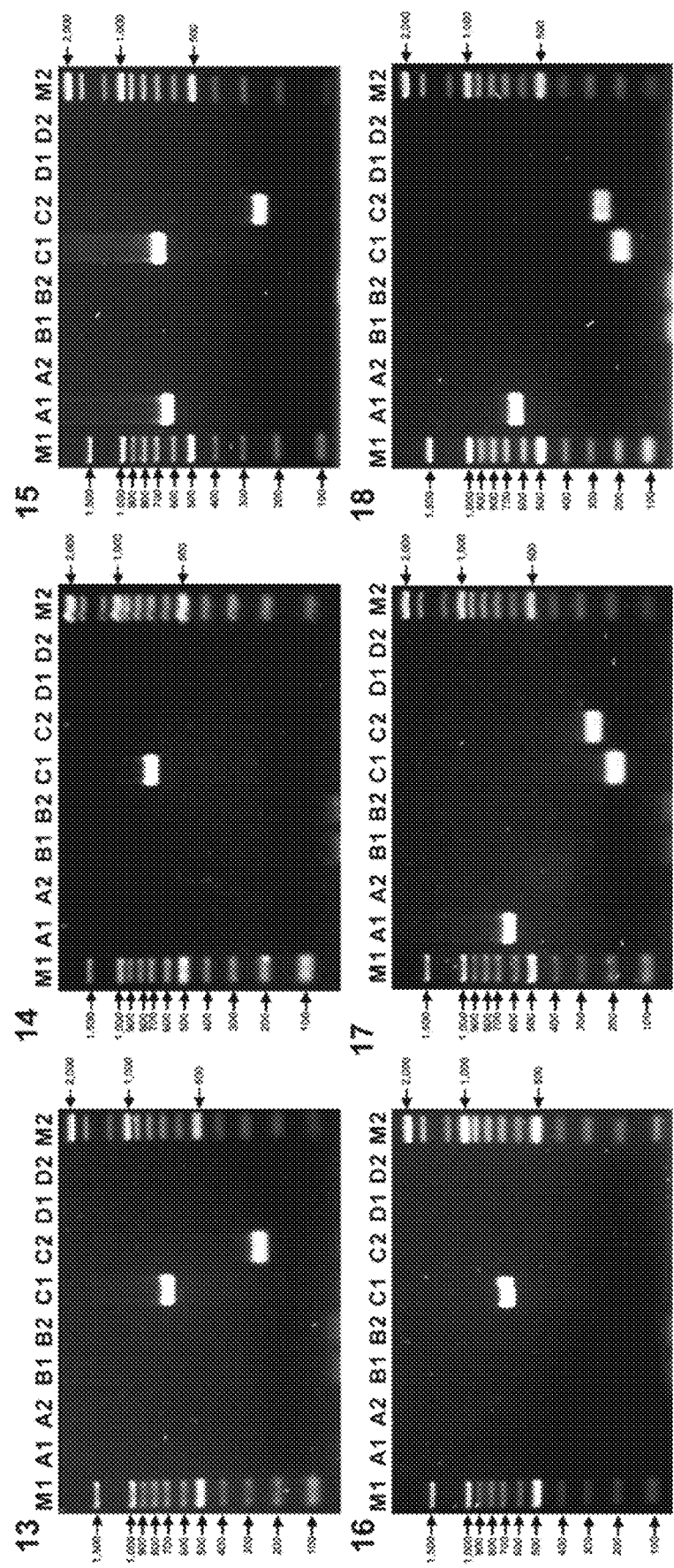
Figures 3, 3F, 4:
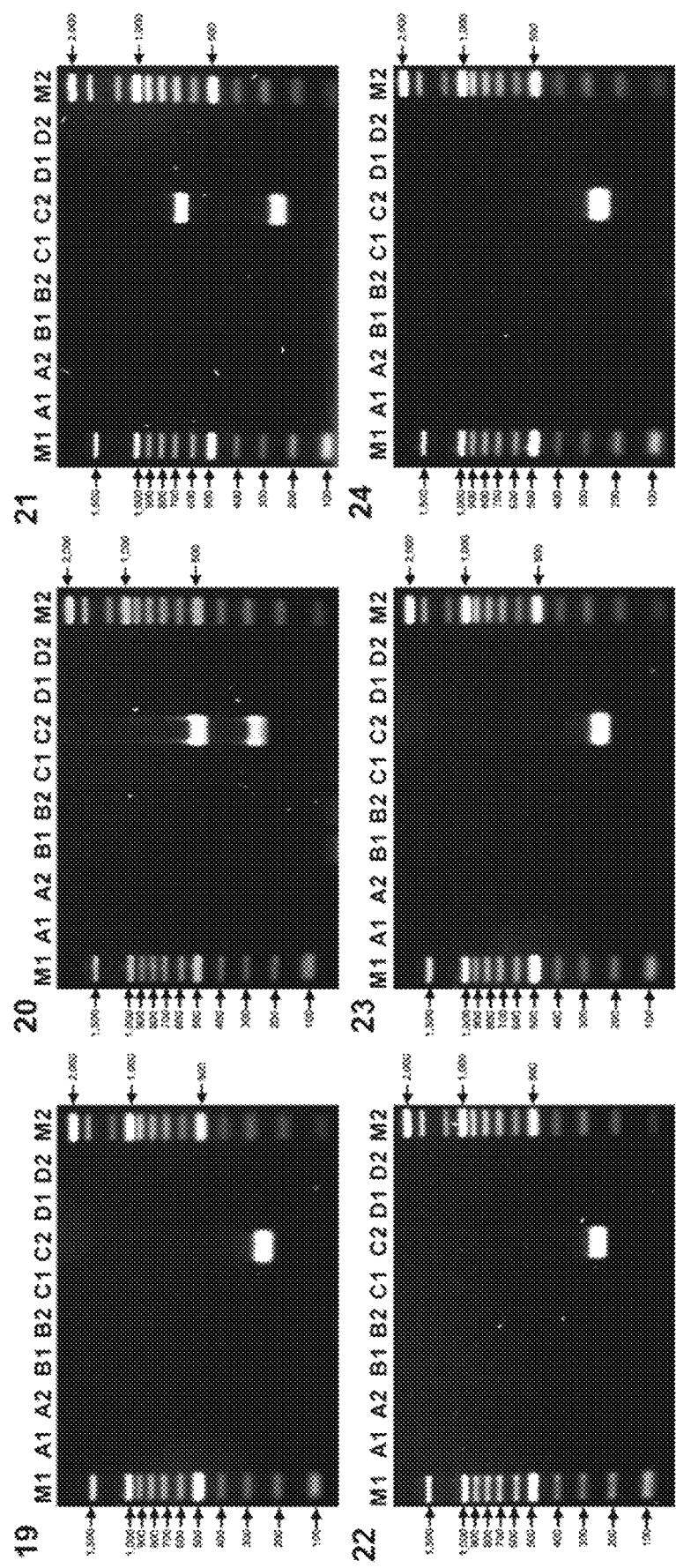
Figures 3, 3F, 4, 5:
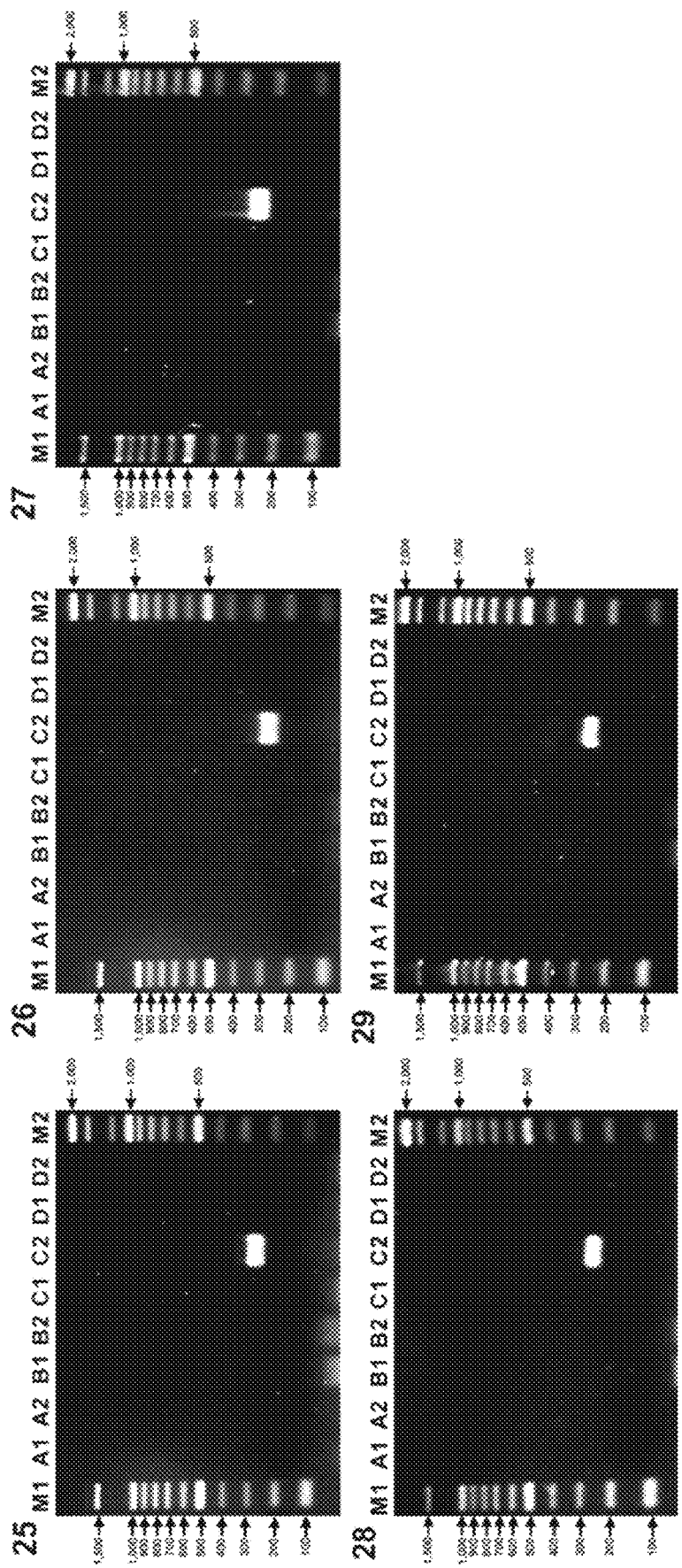
Figures 1, 3G:
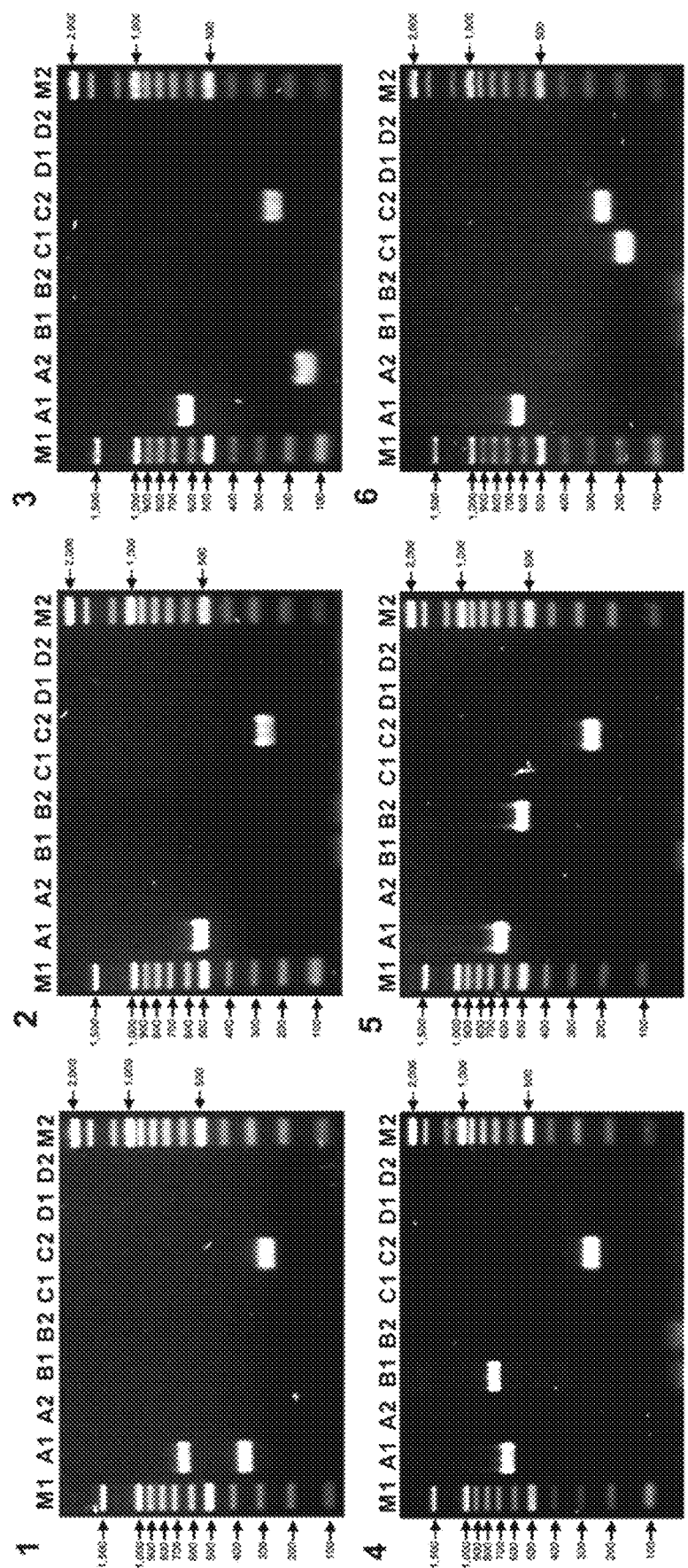
Figures 2, 3G:
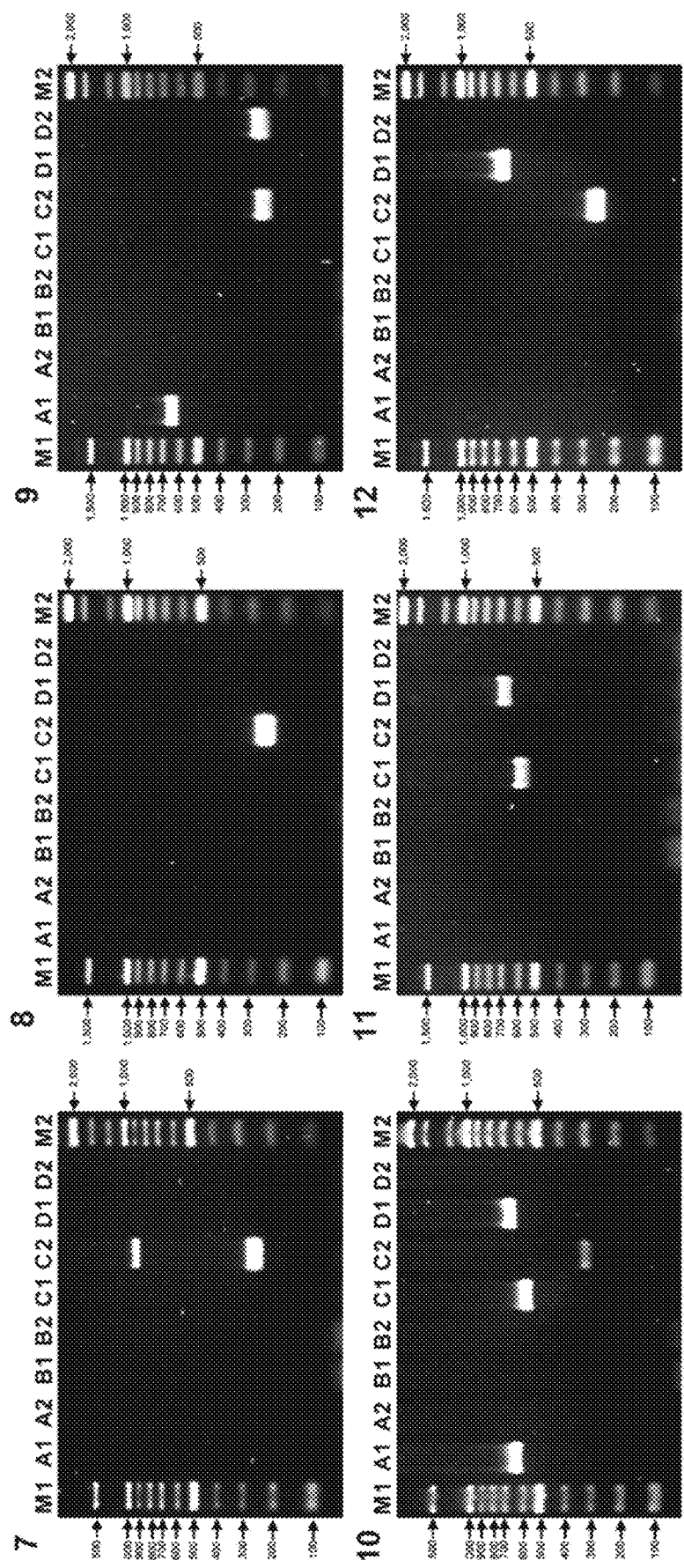
Figures 3, 3G:
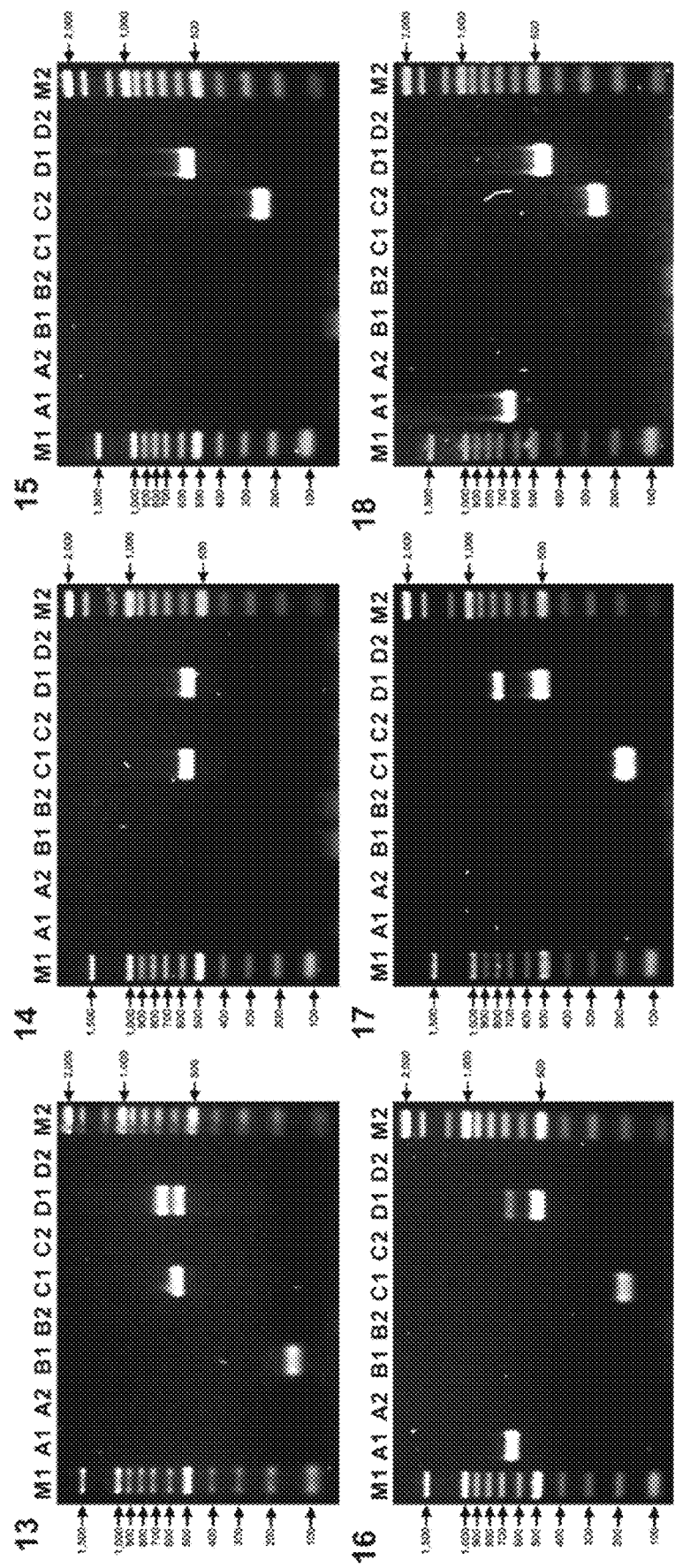
Figures 3, 3G, 4:
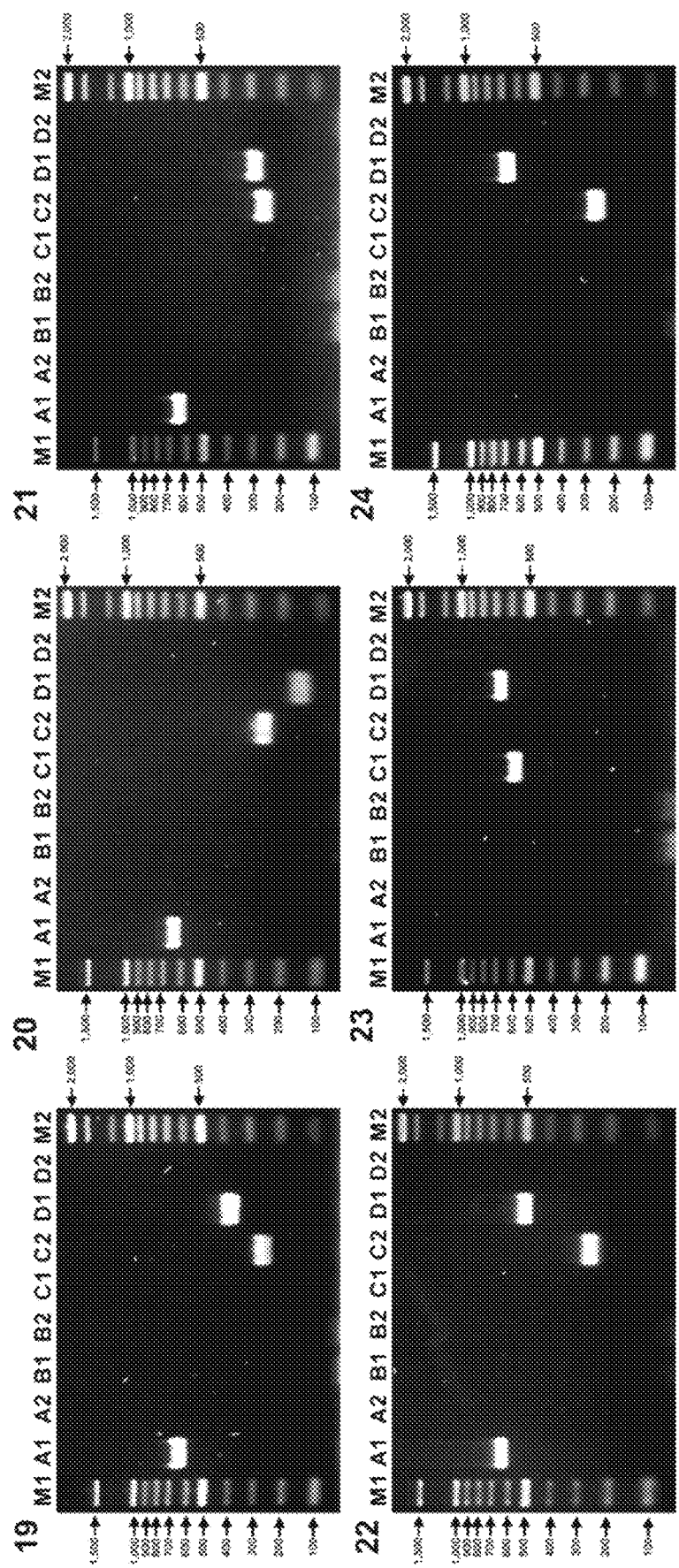
Figures 3, 3G, 4, 5:
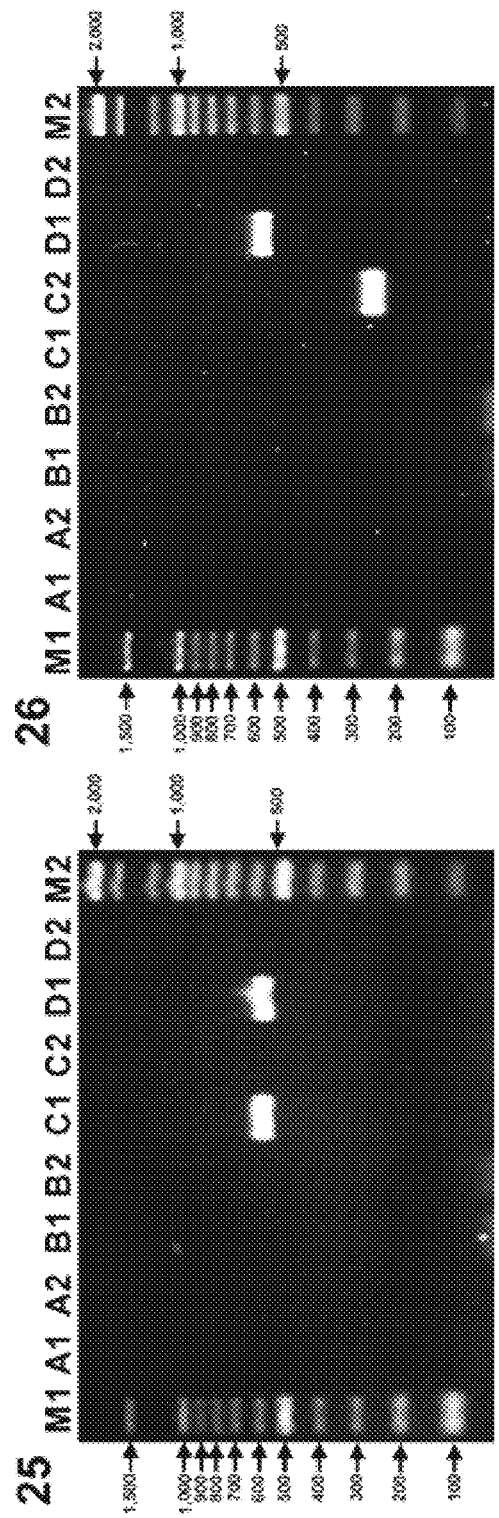
Figures 1, 3H:
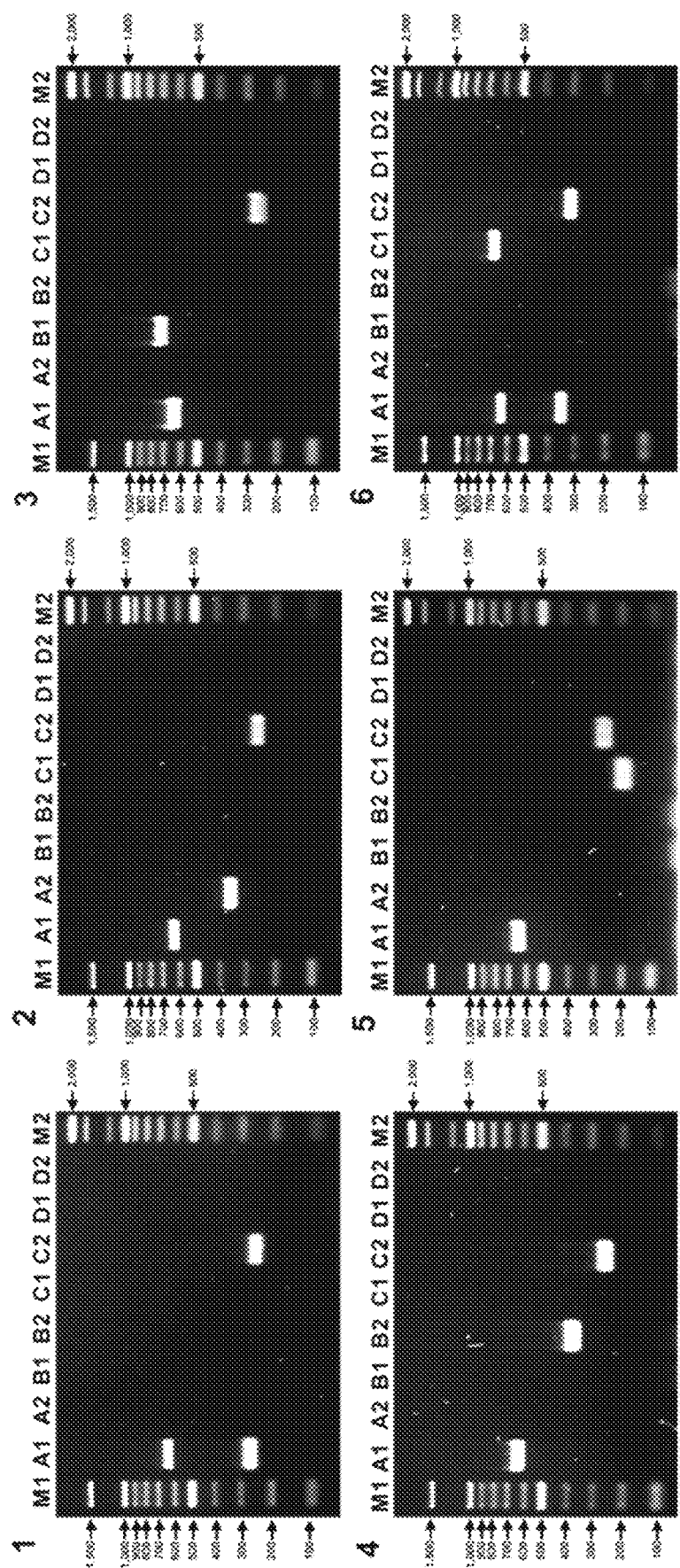
Figures 2, 3H:
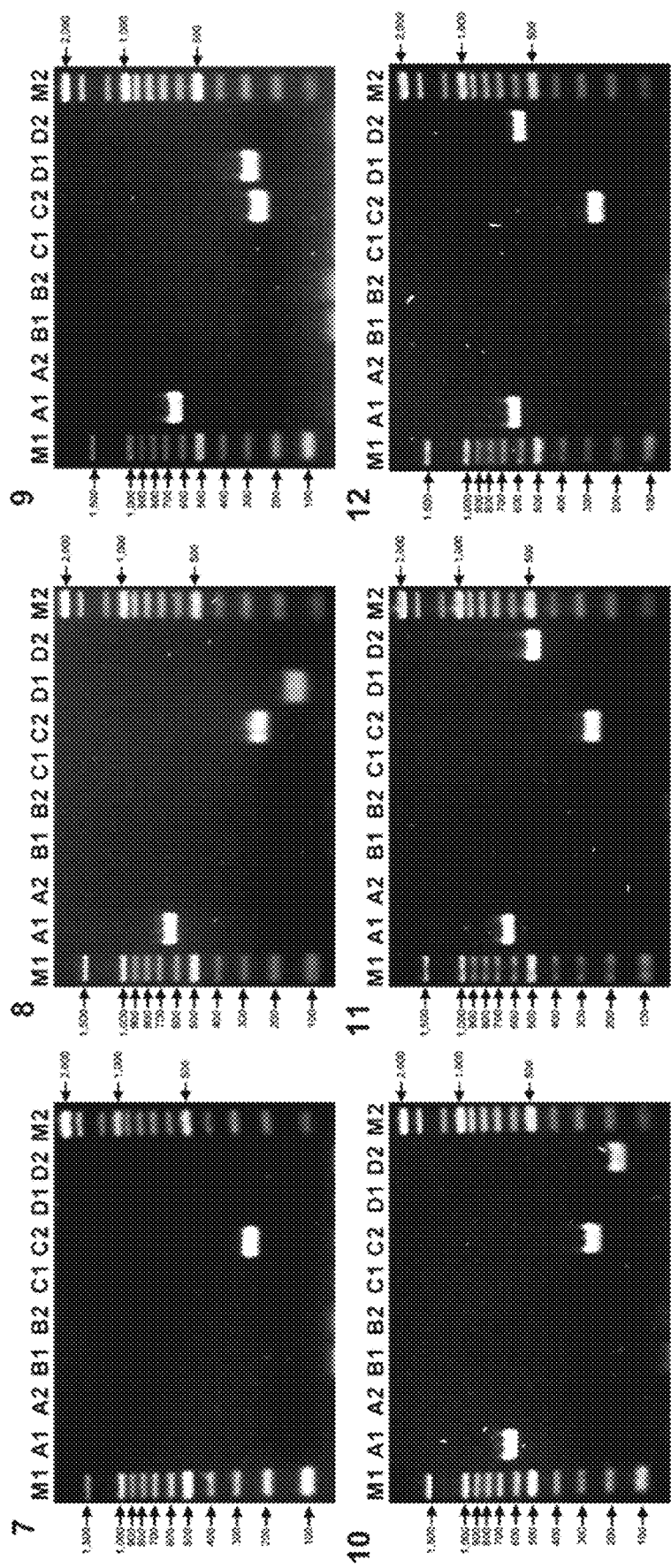
Figures 3, 3H:
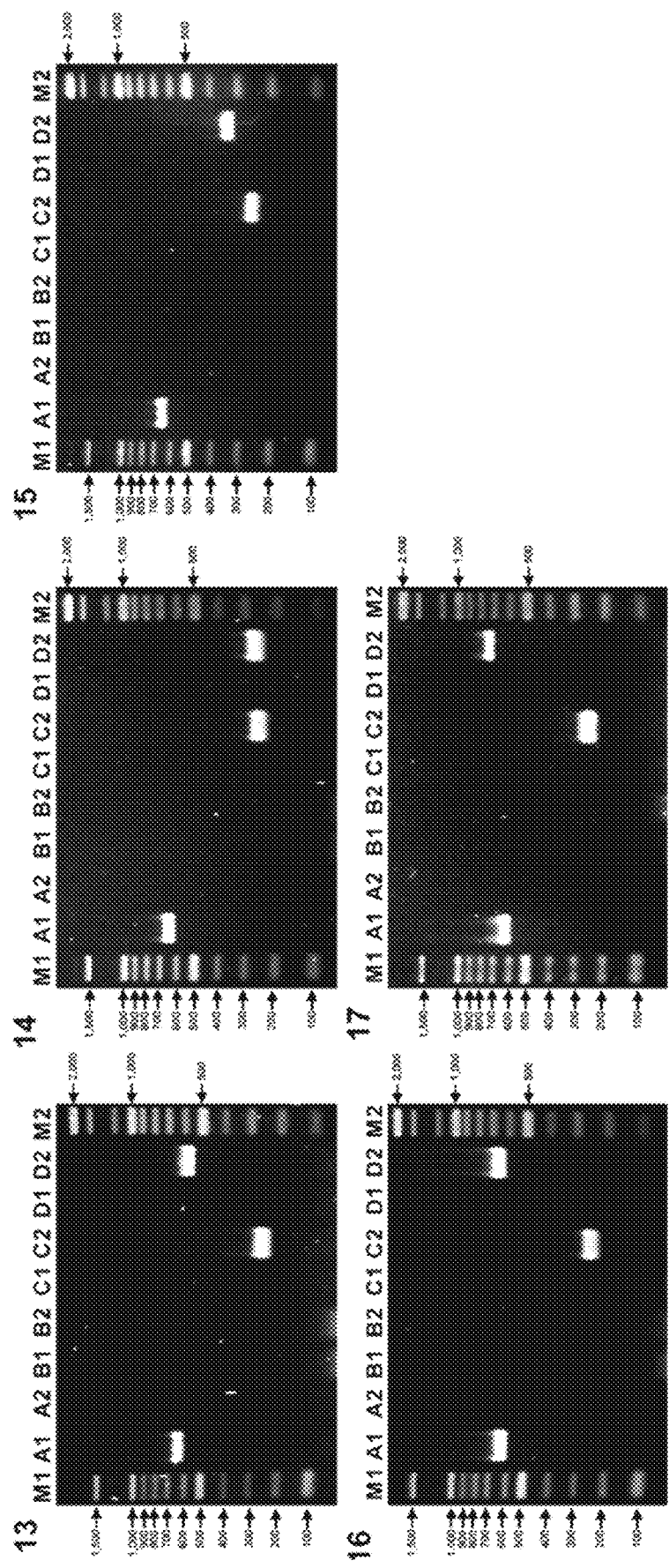

FIGS. 3*h*-1 to 3*h*-3 show results from multiplex PCR assays for the detection of A1-specific bla genes in positive (8) or negative (9) control strains. (1) *E. coli* TOPVEB02 harboring VEB-2 (lane A1), TEM type (lane A1), and BER (EC2, KL, AmpC-10) type (lane C2). (2) *E. coli* TOPC025 harboring CTX-M-25 (lane A2), TEM type (lane A1), and BER (EC2, KL, AmpC-10) type (lane C2). (3) *E. coli* TOPMBL1B harboring Mbl1b (lane B1), TEM type (lane A1), and BER (EC2, KL, AmpC-10) type (lane C2). (4) *E. coli* TOPSPM01 harboring SPM-1 (lane B2), TEM type (lane A1), and BER (EC2, KL, AmpC-10) type (lane C2). (5) *E. coli* TOPADC033 harboring ADC-33 (lane C1), TEM type (lane A1), and BER (EC2, KL, AmpC-10) type (lane C2). (6) *E. coli* CSH-2 harboring MOX-1 (lane C2), TEM type (lane A1), SHV type (lane A1), and MIR (ACT, CHE, GC1, AmpC-3) type (lane C1). (7) *E. coli* JF701 harboring BER (EC2, KL, AmpC-10) type (lane C2). (8) *E. coli* TOPDXA042 harboring OXA-42 (lane D1), TEM type (lane A1), and BER (EC2, KL, AmpC-10) type (lane C2). (9) *E. coli* TOPDXA063 harboring OXA-63 (lane D1), TEM type (lane A1), and BER (EC2, KL, AmpC-10) type (lane C2). (10) *E. coli* TOPDXA020 harboring OXA-20 (lane D2), TEM type (lane A1), and BER (EC2, KL, AmpC-10) type (lane C2). (11) *E. coli* TOPDXA048 harboring OXA-48 (lane D2), TEM type (lane A1), and BER (EC2, KL, AmpC-10) type (lane C2). (12) *E. coli* TOPDXA058 harboring OXA-58 (lane D2), TEM type (lane A1), and BER (EC2, KL, AmpC-10) type (lane C2). (13) *E. coli* TOPDXA097 harboring OXA-97 (lane D2), TEM type (lane A1), and BER (EC2, KL, AmpC-10) type (lane C2). (14) *E. coli* TOPDXA211 harboring OXA-211 (lane D2), TEM type (lane A1), and BER (EC2, KL, AmpC-10) type (lane C2). (15) *E. coli* TOPDXA214 harboring OXA-214 (lane D2), TEM type (lane A1), and BER (EC2, KL, AmpC-10) type (lane C2). (16) *E. coli* TOPDXA228 harboring OXA-228 (lane D2), TEM type (lane A1), and BER (EC2, KL, AmpC-10) type (lane C2). (17) *E. coli* TOPDXA235 harboring OXA-235 (lane D2), TEM type (lane A1), and BER (EC2, KL, AmpC-10) type (lane C2).

FIGS. 4*a* to 4*e* show optimization of primer pairs in multiplex PCR assays. Several false positive bands among 100 positive control strains were detected in some multiplex PCR tubes, including A1, A2, C1, C2, and D1 multiplex tubes. Here, representative optimization of primer pairs in A1, A2, and D1 multiplex tubes was shown. To identify which primer is responsible for the false positive band(s), multiplex PCR assays using primer mixtures without one primer were performed. All multiplex PCR products (10 µl) were separated in a 2% agarose gel. To exactly find false positive band(s) if false positive result(s) might happened, 10 µl (not 5 µl) of PCR products were used. (a) In case of *K. pneumoniae* CHAK36, the weak intensity (non-optimized result) of GES type (top band) in A1 multiplex tube (lane A1) was improved by a small increase in length of GES type primer pair (optimized result). Five conserved bases (5'-CATTC-3') were added in the 5' end of GES type-F primer, while a single conserved base (5'-A-3') was inserted in the 5' end of GES type-R primer. (b) Optimization process in case of *P. aeruginosa* WK28. Experimental procedures to identify the primer(s) responsible for false positive bands were described in the Online Methods. A false positive band (arrow) was shown in lanes 2-8 and 10 but the false positive band (dashed red box) was removed in lane 1 (without only CTX-M-1 type-F primer) and lane 9 (without only CTX-M-25 type-F primer. DNA sequence analysis showed that the false positive amplicon was the PCR product of a chromosomal gene coding for β-hexosaminidase in the control strain. The forward primer of CTX-M-1 type (5'-AGTTCACGCTGATGGCGAC-3') and the forward primer of CTX-M-25 type (5'-AAAAGCGTAAGGCGGGCGA-3') responsible for the false positive band were changed to new primers (CTX-M-1-F: 5'-CAGTTCACGCTGATGGCGAC-3'; CTX-M-25-F: 5'-TAATGACGACAGCCTGTGTTTC-3'). Lane 1: A2 multiplex tube without CTX-M-1 type-F; lane 2: A2 multiplex tube without CTX-M-1 type-R; lane 3: A2 multiplex tube without CTX-M-2 type-F; lane 4: A2 multiplex tube without CTX-M-2 type-R; lane 5: A2 multiplex tube without CTX-M-8 type-F; lane 6: A2 multiplex tube without CTX-M-8 type-R; lane 7: A2 multiplex tube without CTX-M-9 type-F; lane 8: A2 multiplex tube without CTX-M-9 type-R; lane 9: A2 multiplex tube without CTX-M-25 type-F; lane 10: A2 multiplex tube without CTX-M-25 type-R. (c) In case of *P. aeruginosa* WK28, a false positive band (non-optimized result with tow unchanged primers) in an A2 multiplex PCR tube (lane A2) was removed by redesigning two primers responsible for the false positive band (optimized result with two newly-changed primers). (d) Optimization process in case of *E. coli* CF0022. Experimental procedures to identify the primer(s) responsible for false positive bands were described in the Online Methods. One (or two) false positive band(s) (arrow) were shown in lanes 4-16 but two false positive bands (dashed red box) were removed in lanes 1 (without only OXA-1 type-F primer), lane 2 (without only OXA-1 type-R primer), and lane 3 (without only OXA-2 type-F primer). Therefore, these three primers were responsible for two false positive bands. DNA sequence analysis showed that the false positive amplicons were PCR products of chromosomal genes (two genes coding for periplasmic murein peptide-binding protein MppA and the catalytic subunit of acetolactate synthase) in the control strain. Lane 1: D1 multiplex tube without OXA-1 type-F; lane 2: D1 multiplex tube without OXA-1 type-R; lane 3: D1 multiplex tube without OXA-2 type-F; lane 4: D1 multiplex tube without OXA-2 type-R; lane 5: D1 multiplex tube without OXA-10 type-F; lane 6: D1 multiplex tube without OXA-10 type-R; lane 7: D1 multiplex tube without OXA-23 type-F; lane 8: D1 multiplex tube without OXA-23 type-R; lane 9: D1 multiplex tube without OXA-24 type-F; lane 10: D1 multiplex tube without OXA-24 type-R; lane 11: D1 multiplex tube without OXA-42 type-F; lane 12: D1 multiplex tube without OXA-42 type-R; lane 13: D1 multiplex tube without OXA-51 type-F; lane 14: D1 multiplex tube without OXA-51 type-R; lane 15: D1 multiplex tube without OXA-63 type-F; lane 16: D1 multiplex tube without OXA-63 type-R. (e) In case of *E. coli* CF0022, two false positive bands (non-optimized result) in a D1 multiplex PCR tube was removed by redesigning primers responsible for the false positive bands. Although three primers (OXA-1 type-F: 5'-CAATCATACAC-CAAAGACGTGGA-3'; OXA-1 type-R: 5'-GCTTCCTG-TAAGTGCGGACAC-3'; OXA-2-F: 5'-AGTTGTGGCA-GACGAACGC-3') were responsible for two false positive bands (non-optimized result), two false positive bands could be removed by the only one changed primer (OXA-1-R; 5'-AGCTTCCTGTAAGTGCGGACACA-3') (optimized result).

DETAILED DESCRIPTION

Hereinafter, the present invention will be described in further detail with reference to examples. It is to be understood, however, that these examples are for illustrative purposes only and are not to be construed to limit the scope of the present invention.

The terms "complement" and "complementary," as used herein, refer to a nucleic acid that is capable of hybridizing to a specified nucleic acid molecule under stringent hybridization conditions. Thus, a specified DNA molecule is typically "complementary" to a nucleic acid if hybridization occurs between the specified DNA molecule and the nucleic acid. If the specified DNA molecule hybridizes to the full length of the nucleic acid molecule, then the specified DNA molecule is typically a "full-length complement." "Complementary," further refers to the capacity of purine and pyrimidine nucleotides to associate through hydrogen bonding in double stranded nucleic acid molecules. The following base pairs are complementary: guanine and cytosine; adenine and thymine; and adenine and uracil.

Hereinafter we use the classification of β-lactamase according to Ambler's molecular classification. The most widely used classification of β-lactamases is the Ambler classification35 that divides β-lactamases into four classes (A, B, C, and D) based upon their amino acid sequences. Ambler originally specified two classes: class A, the active-site serine β-lactamases; and class B, the metallo-β-lactamases that require a bivalent metal ion, usually Zn2+, for activity. Later a new class of serine β-lactamases was found that bore little sequence similarity to the then-known class A enzymes. Designated class C, its members are also known as the 'AmpC' β-lactamases. Another class of serine β-lactamases, familiarly known as the OXA β-lactamases, was found to bear little resemblance to either class A or class C and was designated class D. The three classes of serine β-lactamases are sufficiently different that alignment programs such as BLAST find no detectable sequence similarity, yet there is sufficient structural similarity among the three classes of serine β-lactamases that it is clear that they are homologous, i.e. descended from a common ancestor.

Example 1

Primer Design for Detecting All Clinically-Important β-Lactamase (bla) Genes

Our strategy for the bla gene typing is the primer design using gene type-specific regions. We divided previously-reported bla genes into 54 types, which are comprised of 13 in class A, 16 in class B, 10 in class C, and 15 in class D (Table 1).

TABLE 1

| Class | Multiplex PCR tube | Type name | Gene type | β-Lactamase (s) targeted | Amplicon size (bp) | Sequence Number |
|---|---|---|---|---|---|---|
| A | A1 | A1-1 | GES type | GES-1* to GES-22 | 748 | Seq. No. 1 |
|  |  |  |  |  |  | Seq. No. 2 |
|  |  | A1-2 | TEM type | TEM-1* to TEM-209 | 626 | Seq. No. 3 |
|  |  |  |  |  |  | Seq. No. 4 |
|  |  | A1-3 | NMC (IMI) type | NMC-A*; IMI-1 to IMI-3 | 513 | Seq. No. 5 |
|  |  |  |  |  |  | Seq. No. 6 |
|  |  | A1-4 | KPC type | KPC-1* to KPC-10 | 438 | Seq. No. 7 |
|  |  |  |  |  |  | Seq. No. 8 |
|  |  | A1-5 | SHV type | SHV-1* to SHV-173 | 341 | Seq. No. 9 |
|  |  |  |  |  |  | Seq. No. 10 |
|  |  | A1-6 | VEB type | VEB-1* to VEB-8 | 257 | Seq. No. 11 |
|  |  |  |  |  |  | Seq. No. 12 |

TABLE 1-continued

| Class | Multiplex PCR tube | Type name | Gene type | β-Lactamase(s) targeted | Amplicon size (bp) | Sequence Number |
|---|---|---|---|---|---|---|
| | | A1-7 | PER type | PER-1* to PER-7 | 152 | Seq. No. 13<br>Seq. No. 14 |
| | | A1-8 | SME type | SME-1* to SME-3 | 110 | Seq. No. 15<br>Seq. No. 16 |
| | A2 | A2-1 | CTX-M-9 type | CTX-M-9*, 13, 14, 16 to 19, 21, 24, 27, 38, 45 to 51, 65, 67, 81, 83 to 87, 90, 98, 99, 102, 104 to 106, 110, 111, 113, 121, 122, 126, 129, 130, 134 | 689 | Seq. No. 17<br>Seq. No. 18 |
| | | A2-2 | CTX-M-1 type | CTX-M-1*, 3, 10, 11, 12, 15, 22, 23, 28, 29, 30, 32, 33, 34, 36, 37, 42, 52 to 55, 57, 58, 60, 61 62, 64, 66, 68, 69, 71, 72, 79 to 80, 82, 101, 107, 108, 109, 114, 116, 117, 133, 136, 139, 142 | 462 | Seq. No. 19<br>Seq. No. 20 |
| | | A2-3 | CTX-M-25 type | CTX-M-25*, 26, 39, 41, 78, 89, 91, 94 | 348 | Seq. No. 21<br>Seq. No. 22 |
| | | A2-4 | CTX-M-2 type | CTX-M-2*, 4 to 7, 20, 31, 35, 43, 44, 56, 59, 76, 77, 92, 95, 97, 124, 131 | 261 | Seq. No. 23<br>Seq. No. 24 |
| | | A2-5 | CTX-M-8 type | CTX-M-8*, 40, 63 | 150 | Seq. No. 25<br>Seq. No. 26 |
| B | B1 | B1-1 | THIN-B | THIN-B* | 896 | Seq. No. 27<br>Seq. No. 28 |
| | | B1-2 | CAU-1 (Mbl1b) | CAU-1*; Mbl1b | 720 | Seq. No. 29<br>Seq. No. 30 |
| | | B1-3 | SIM-1 | SIM-1* | 631 | Seq. No. 31<br>Seq. No. 32 |
| | | B1-4 | CphA (ImiS) type | CphA2*, 4 to 8; ImiS | 567 (570$^d$) | Seq. No. 33<br>Seq. No. 34 |
| | | B1-5 | IND type | IND-1, 3, 5, 6*, 7, 8, 10, 14 | 463 | Seq. No. 35<br>Seq. No. 36 |
| | | B1-6 | IMP type | IMP-1* to 16, 18 to 22, 24 to 35, 37, 38, 40 to 44 | 344 | Seq. No. 37<br>Seq. No. 38 |
| | | B1-7 | NDM type | NDM-1* to NDM-10 | 254 | Seq. No. 39<br>Seq. No. 40 |
| | | B1-8 | VIM type | VIM-1* to VIM-38 | 148 | Seq. No. 41<br>Seq. No. 42 |
| | B2 | B2-1 | AIM-1 | AIM-1* | 836 | Seq. No. 43<br>Seq. No. 44 |
| | | B2-2 | KHM-1 | KHM-1* | 711 | Seq. No. 45<br>Seq. No. 46 |
| | | B2-3 | FEZ-1 | FEZ-1* | 637 | Seq. No. 47<br>Seq. No. 48 |
| | | B2-4 | GOB type | GOB-1* to 15, 18 | 506 | Seq. No. 49<br>Seq. No. 50 |
| | | B2-5 | BlaB type | BlaB-1* to 3, 5 to 13 | 441 | Seq. No. 51<br>Seq. No. 52 |
| | | B2-6 | SPM-1 | SPM-1* | 355 | Seq. No. 53<br>Seq. No. 54 |
| | | B2-7 | EBR-1 | EBR-1* | 262 | Seq. No. 55<br>Seq. No. 56 |
| | | B2-8 | JOHN-1 | JOHN-1* | 186 | Seq. No. 57<br>Seq. No. 58 |
| C | C1 | C1-1 | ACC (AmpC-1) type | ACC-1* to 5; 6 other AmpCs | 984 | Seq. No. 59<br>Seq. No. 60 |
| | | C1-2 | DHA (AmpC-2) type | DHA-1* to 3, 5 to 7; 18 other AmpCs | 881 | Seq. No. 61<br>Seq. No. 62 |
| | | C1-3 | MIR (ACT, CHE, GC1, AmpC-3) type | MIR-1* to 6; ACT-1 to 8, 10, 14 to 16, 20, 21, 23; CHE; GC-1; 26 other AmpCs | 669 | Seq. No. 63<br>Seq. No. 64 |

TABLE 1-continued

| Class | Multiplex PCR tube | Type name | Gene type | β-Lactamase(s) targeted | Amplicon size (bp) | Sequence Number |
|---|---|---|---|---|---|---|
| | | C1-4 | PDC (AmpC-4) type | PDC-1* to 3; 37 other AmpCs | 562 | Seq. No. 65<br>Seq. No. 66 |
| | | C1-5 | ADC (AmpC-5) type | ADC-1* to 7, 10, 11 to 23, 25, 26, 29, 30, 38, 39, 41 to 44, 50 to 54, 56, 57, 64, 67; 23 other AmpCs | 176 | Seq. No. 67<br>Seq. No. 68 |
| | C2 | C2-1 | CMY-2 (CFE, LAT, BIL, AmpC-6) type | CMY-2* to 7, 12 to 18, 20 to 103, 110; CFE, LAT; BIL; 29 other AmpCs | 888 | Seq. No. 69<br>Seq. No. 70 |
| | | C2-2 | Ear (AmpC-7) type | Ear0* to 2; 13 other AmpCs | 657 | Seq. No. 71<br>Seq. No. 72 |
| | | C2-3 | 520R (SRT-1, HD, SMSA, AmpC-8) type | 520R*; SRT-1; HD; SMSA; 7 other AmpCs | 477 | Seq. No. 73<br>Seq. No. 74 |
| | | C2-4 | CMY-1 (MOX, FOX, AmpC-9) type | CMY-1*, 8 to 11, 19; MOX-1 to 7; FOX-1 to 10; 16 other AmpCs | 306 | Seq. No. 75<br>Seq. No. 76 |
| | | C2-5 | BER (EC2, KL, AmpC-10) type | BER*; EC2; KL; 85 other AmpCs | 241 | Seq. No. 77<br>Seq. No. 78 |
| D | D1 | D1-1 | OXA-23 type | OXA-23*, 27, 49, 73, 133, 134, 146, 165 to 171, 225, 239 | 718 | Seq. No. 79<br>Seq. No. 80 |
| | | D1-2 | OXA-2 type | OXA-2*, 3, 15, 21, 32, 34, 36, 141, 161, 210 | 639 | Seq. No. 81<br>Seq. No. 82 |
| | | D1-3 | OXA-10 type | OXA-7, 10*, 11, 13, 14, 16, 17, 19, 28, 35, 56, 74, 101, 142, 145, 147, 183, 240, 251, 256 | 549 | Seq. No. 83<br>Seq. No. 84 |
| | | D1-4 | OXA-51 type | OXA-51*, 64 to 71, 75 to 80, 82 to 84, 86 to 95, 98, 99, 106 to 113, 115 to 117, 128, 130 to 132, 138, 148 to 150, 172 to 180, 194 to 197, 200 to 203, 206, 208, 216 to 217, 241, 248, 250 | 490 | Seq. No. 85<br>Seq. No. 86 |
| | | D1-5 | OXA-1 type | OXA-1*, 4, 30, 31, 47, 224 | 437 | Seq. No. 87<br>Seq. No. 88 |
| | | D1-6 | OXA-24 type | OXA-24* to 26, 33, 40, 72, 139, 143, 160, 182, 207, 231 | 356 | Seq. No. 89<br>Seq. No. 90 |
| | | D1-7 | OXA-63 type | OXA-63*, 136, 137, 192 | 267 | Seq. No. 91<br>Seq. No. 92 |
| | | D1-8 | OXA-42 type | OXA-42*, 43, 57, 59 | 142 | Seq. No. 93<br>Seq. No. 94 |
| | D2 | D2-1 | OXA-235 type | OXA-235*, 237, 278 | 721 | Seq. No. 95<br>Seq. No. 96 |
| | | D2-2 | OXA-228 type | OXA-228* to 230, 257 | 641 | Seq. No. 97<br>Seq. No. 98 |
| | | D2-3 | OXA-58 type | OXA-58*, 96, 97, 164 | 560 | Seq. No. 99<br>Seq. No. 100 |
| | | D2-4 | OXA-48 type | OXA-48*, 162, 163, 181, 204, 232, 244, 245, 247 | 473 | Seq. No. 101<br>Seq. No. 102 |
| | | D2-5 | OXA-214 type | OXA-214*, 215 | 321 | Seq. No. 103<br>Seq. No. 104 |

TABLE 1-continued

| Class | Multiplex PCR tube | Type name | Gene type | β-Lactamase(s) targeted | Amplicon size (bp) | Sequence Number |
|---|---|---|---|---|---|---|
| | | D2-6 | OXA-211 type | OXA-211*, 212 | 251 | Seq. No. 105<br>Seq. No. 106 |
| | | D2-7 | OXA-20 type | OXA-20*, 37 | 160 | Seq. No. 107<br>Seq. No. 108 |

TABLE 2

| Sequence Number | Sequence (5'-3') | Length (bases) |
|---|---|---|
| Seq. No. 1 | CATTCACGCACTATTACTGGCA | 22 |
| Seq. No. 2 | AGCGTAATCTCTCTCCTGGG | 20 |
| Seq. No. 3 | CGTGTCGCCCTTATTCCCT | 19 |
| Seq. No. 4 | GCAACTTTATCCGCCTCCAT | 20 |
| Seq. No. 5 | GAACGATTTCCATTATGTAGTTC | 23 |
| Seq. No. 6 | ATCGCCAACTACCCAATCGCTTG | 23 |
| Seq. No. 7 | GACACACCCATCCGTTACG | 19 |
| Seq. No. 8 | GGTTCCGGTTTTGTCTCCG | 19 |
| Seq. No. 9 | ATCTGGTGGACTACTCGCC | 19 |
| Seq. No. 10 | ATCGTCCACCATCCACTGC | 19 |
| Seq. No. 11 | CCCGATGCAAAGCGTTATG | 19 |
| Seq. No. 12 | GAACAGAATCAGTTCCTCCG | 20 |
| Seq. No. 13 | TGGATGGTCGAAACCACCACAG | 22 |
| Seq. No. 14 | CGTCCATCAGGCAACAGAATGA | 22 |
| Seq. No. 15 | GGGGAATGTTCTCAATGCTAA | 21 |
| Seq. No. 16 | CTACAACCCAATCAGCAGGA | 20 |
| Seq. No. 17 | GAGAGTGCAACGGATGATGTT | 21 |
| Seq. No. 18 | CAGTCCACGACGTCGGTAAG | 20 |
| Seq. No. 19 | CAGTTCACGCTGATGGCGAC | 20 |
| Seq. No. 20 | TTCGTCTCCCAGCTGTCGGG | 20 |
| Seq. No. 21 | TAATGACGACAGCCTGTGTTTC | 22 |
| Seq. No. 22 | CGCTCAACTCCCCGAATGTCAT | 22 |
| Seq. No. 23 | CCTGCTATTTAGCAGCGCAA | 20 |
| Seq. No. 24 | AGGTCGCTCTTCTTGATT | 18 |
| Seq. No. 25 | AGACATCGCGTTAAGCGGA | 19 |
| Seq. No. 26 | CAGCGCCACTCCCAACCG | 18 |
| Seq. No. 27 | ACACTATTGGCGAAGTTGATG | 21 |
| Seq. No. 28 | TCCTTCGCCAGCCGTTTCG | 19 |
| Seq. No. 29 | TGGTCGGCAACATCTATTACGT | 22 |
| Seq. No. 30 | TGTTGAAGGCGGCTTCGGA | 19 |
| Seq. No. 31 | TGCGGAAGAAGCCCAGCCA | 19 |
| Seq. No. 32 | TGTGAGTTTCAATAGTGATGCG | 22 |

TABLE 2-continued

| Sequence Number | Sequence (5'-3') | Length (bases) |
|---|---|---|
| Seq. No. 33 | CGTGGTGCTGATGGCGAG | 18 |
| Seq. No. 34 | AGGTTGCCCAGCTTCTCCT | 19 |
| Seq. No. 35 | CAATACCAAAGCCTGATGGATC | 22 |
| Seq. No. 36 | CGCCGCCTTTCCATTCATC | 19 |
| Seq. No. 37 | AAACACGGTTTGGTGGTTCTTGT | 23 |
| Seq. No. 38 | CAAACCACTACGTTATCTGGAG | 22 |
| Seq. No. 39 | ATCTCGACATGCCGGGTTTCGG | 22 |
| Seq. No. 40 | AAGCTGGTTCGACAACGCAT | 20 |
| Seq. No. 41 | GTGTTTGGTCGCATATCGCAAC | 22 |
| Seq. No. 42 | TTCTCAATCTCCGCGAGAAGT | 21 |
| Seq. No. 43 | TCGCCCTCTCATCCACAGC | 19 |
| Seq. No. 44 | TTCCTCGGCCAGGCGCTT | 18 |
| Seq. No. 45 | TAGCTCTTGTTATATCGTTTGGT | 23 |
| Seq. No. 46 | TAGCTGCAAGCGCTTCAACT | 20 |
| Seq. No. 47 | GTCACACCGAGAGGGAACA | 19 |
| Seq. No. 48 | TACAGCCTGTGGGATCAACA | 20 |
| Seq. No. 49 | TATATTACGTAGGAACCTATGATTTGGC | 28 |
| Seq. No. 50 | AACTTCAGAAAATTTCTTATCAACAATAA | 29 |
| Seq. No. 51 | GCCGGAGGTCTTGAATATTTTGGTAA | 26 |
| Seq. No. 52 | TTAATTTGAAGCCTTTTGTTTTTGTTG | 27 |
| Seq. No. 53 | GAAGCCGAAGAAAGTAGTAGCCA | 23 |
| Seq. No. 54 | GCCGCCAAACAGCAGTTTCTTC | 22 |
| Seq. No. 55 | GCAAATGGAATGTATTTGGTAACGAAT | 27 |
| Seq. No. 56 | CAATCTCAAATTTAGAAGTCGCTTTTC | 27 |
| Seq. No. 57 | AGATTTCTGCCAATGCTATGTA | 22 |
| Seq. No. 58 | TCTTGTAAAAATCAAATCCTCCT | 23 |
| Seq. No. 59 | GTTATCCGTGATTACCTGTCT | 21 |
| Seq. No. 60 | ATCCACACATTTTCCTGTGGCGG | 23 |
| Seq. No. 61 | GCAACACTGATTTCCGCTCTGCT | 23 |
| Seq. No. 62 | TCTTTCTGCTGCGGCCAGTCATA | 23 |
| Seq. No. 63 | TGCGCTTTTATCAAAACTGGCAGCCG | 26 |
| Seq. No. 64 | GGTATGCCGCCTCAACGCGTG | 21 |

TABLE 2-continued

| Sequence Number | Sequence (5'-3') | Length (bases) |
|---|---|---|
| Seq. No. 65 | GATCGCCTGAAGGCACTGGT | 20 |
| Seq. No. 66 | GCACGTCGAGGTGGGTCTGT | 20 |
| Seq. No. 67 | CCGCGACAGCAGGTGGATATGC | 22 |
| Seq. No. 68 | GTCTGTTTGTACTTCATCTGGAAA | 24 |
| Seq. No. 69 | GCAGGAGCAGGCTATTCCGG | 20 |
| Seq. No. 70 | GTTTTATGCACCCATGAGGCTTTC | 24 |
| Seq. No. 71 | CGAACTGGTCAATCAGACCATC | 22 |
| Seq. No. 72 | TCAATGCTCGACTTCACGCCGTA | 23 |
| Seq. No. 73 | CTATGCGCAGCAGCAGGGCAA | 21 |
| Seq. No. 74 | AGATAGCGAATCAGATCGCGAGC | 23 |
| Seq. No. 75 | TCAGCGAGCAGACCCTGTTCG | 21 |
| Seq. No. 76 | CTATGCTGGGGTTGGAGTACTGG | 23 |
| Seq. No. 77 | TACCGCCTCTTGCTCCACATTTGC | 24 |
| Seq. No. 78 | GCCACCAAGCACGCCCGTAAATG | 23 |
| Seq. No. 79 | CTGGTTGTACGGTTCAGCAT | 20 |
| Seq. No. 80 | GGCATTTCTGACCGCATTTCCAT | 23 |
| Seq. No. 81 | AGTTGTGGCAGACGAACGC | 19 |
| Seq. No. 82 | AGGATTGCCCGCACGATTG | 19 |
| Seq. No. 83 | CTCTGCCGAAGCCGTCAAT | 19 |
| Seq. No. 84 | GACTCAGTTCCCACACCAG | 19 |
| Seq. No. 85 | AGTATGTACCTGCTTCGACC | 20 |
| Seq. No. 86 | GGCTGAACAACCCATCCAG | 19 |
| Seq. No. 87 | CAATCATACACCAAAGACGTGGA | 23 |
| Seq. No. 88 | AGTTTCCTGTAAGTGCGGACACA | 23 |
| Seq. No. 89 | GACTTTAGGTGAGGCAATGGC | 21 |
| Seq. No. 90 | GCTCCACCCAACCAGTCAAC | 20 |
| Seq. No. 91 | CTAATAGCAATGCTGAAGGAACA | 23 |
| Seq. No. 92 | CTTTATATGCCGGTACTTGCGA | 22 |
| Seq. No. 93 | TGCGAAGACGATCTGCACGG | 20 |
| Seq. No. 94 | CAGGAAGCCTGCGTCGTAGC | 20 |
| Seq. No. 95 | CTTGAGCCTGACAGCCTGTA | 20 |
| Seq. No. 96 | CATATTACTTTGCATCTGCATATT | 24 |
| Seq. No. 97 | CAACGCCCAGTCATATCAGA | 20 |
| Seq. No. 98 | GTCACCTTGCCATTGGGTTG | 20 |
| Seq. No. 99 | GATCAGAATGTTCAAGCGCT | 20 |
| Seq. No. 100 | ACAGCCATTCCCCAGCCACT | 20 |
| Seq. No. 101 | GGGCGTAGTTGTGCTCTG | 18 |
| Seq. No. 102 | CTTCGGTCAGCATGGCTTGT | 20 |
| Seq. No. 103 | CATACGGTAATGATCTGAATCG | 22 |
| Seq. No. 104 | AAGGTCCAATGAGCCAGAAGT | 21 |
| Seq. No. 105 | TGCAAGCATCTGCCGTTCCC | 20 |
| Seq. No. 106 | TTCAATCAGCAGCATGTCTTGT | 22 |
| Seq. No. 107 | GCTATTCGCCTGCGTCCA | 18 |
| Seq. No. 108 | GAATTGCGCATTGCCGATCG | 20 |

The sequences of all genes belonging to each gene type were aligned using Clustal W, and gene type-specific conserved regions were identified. Using these regions, primer pairs specific for each gene type were designed in silico and they were compared with all members of the different primer pairs in order to evade cross-hybridization. To easily define gene types of amplicons, primer pairs within each multiplex PCR tube (A1, A2, B1, B2, C1, C2, D1, and D2) were designed to make different PCR product sizes (expected amplicon sizes of Table 1). Therefore, a multiplex PCR was designed with eight reaction tubes including each primer mixture set (e.g., eight primer pairs in case of the multiplex PCR tube A1, Table 1) and to detect and distinguish 1,228 bla genes previously reported, which include 453 class A genes, 140 class B genes, 464 class C genes, and 171 class D genes. The number of total detectable bla gene accession numbers was 7,059 but total number of different and detectable bla genes was 1,228 due to the assignment of different accession numbers to a bla gene. This method ($_{LARGE-SCALE}$blaFinder), to our knowledge, is the first large-scale method showing that a multiplex PCR can detect and distinguish all clinically-important bla genes.

Design of 54 Primer Pairs for the Large-Scale β-Lactamase (bla) Detection Method ($_{LARGE-SCALE}$blaFinder: One Colony Multiplex PCR Assay per Clinical Strain)

Reference gene sequences (total number of bla gene accession numbers was 7,059 but total number of different bla genes was 1,228) for each of 54 bla gene types were obtained from GenBank (http://www.ncbi.nlm.nih.gov/GenBank). Based on multiple alignments of the sequences of all genes belonging to each gene type using Clustal W (http://www.genome.jp/tools/clustalw/), primer pairs were specifically designed within conserved sites to amplify all alleles of each bla gene type. The melting temperatures of designed primer pairs were calculated using Primer3[31] and OligoCalc, an online oligonucleotide properties calculator[32]. To avoid amplification of false positive (or negative) PCR products and to check the specificity of designed primers pairs, a software tool called Primer-BLAST[33] was used (http://www.ncbi.nlm.nih.gov/tools/primer-blast/). Sequences of 54 primer pairs and sizes of the expected products are detailed in Table 1 and Table 2. To confirm the specificity of the PCR assay, 54 primer pairs were evaluated in 54 simplex PCR assays to ensure that they correctly amplified the expected bla genes.

Templates for the $_{LARGE-SCALE}$blaFinder Using a Single Colony

After many trials and errors, the $_{LARGE-SCALE}$blaFinder for multiplex PCRs using a single colony was established as follows: (a) a single colony grown on agar plate overnight was emulsified in 20 μl of 0.1% Triton X-100 using the 10 μl pipette tip, and heated at 100° C. for 10 min; (b) after removing cell debris by a centrifugation step of the cell suspension at 18,000×g for 1 min, the supernatant (1 μl) was used as a template DNA for the multiplex PCR.

Example 2

The bla Detection Method ($_{LARGE-SCALE}$blaFinder) Using a Single Colony

To avoid time consuming steps such as genomic DNA extraction, we introduced the simple $_{LARGE-SCALE}$blaFinder using a single colony (FIG. 1). A single colony from an overnight culture was picked using 10 μl pipette tip and was suspended in the special solution containing 0.1% Triton X-100. The heated colony suspension followed by a centrifugation step was used as a template for the multiplex PCR. A single colony always yielded enough genomic DNA for the $_{LARGE-SCALE}$blaFinder when the heated colony supernatants from control and clinical (test) strains (*Escherichia coli, Enterobacter cloacae, Citrobacter freundii, Providencia rettgeri, Klebsiella pneumoniae, Pseudomonas aeruginosa, Acinetobacter baumannii, Enterobacter aerogenes,* and *Serratia marcescens*) were used as templates. Through precise optimization processes of colony multiplex PCRs, a DNA Taq polymerase, an annealing temperature, and concentrations of components, were selected for the most effective $_{LARGE-SCALE}$blaFinder as described in the Online Method. In case of false positive and/or negative band(s), optimization processes of 54 primer pairs were performed through our novel and unique method Example 3

Evaluation and Optimization of the $_{LARGE-SCALE}$blaFinder Using Control Strains Previously Reported to Harbor bla Gene(s)

In order to verify the ability of this method, PCR assays were performed on previously-reported bacterial strains, which have been reported to have bla gene(s) on chromosome or plasmid (FIGS. 2a to 2h). First, all primer pairs were validated as simplex PCRs before being employed in a multiplex PCR. Expectedly, only one amplification product of each bla gene with the expected size was detected in 54 simplex PCRs for detecting 54 bla gene types (FIGS. 2a to 2h). Besides the size of PCR product, direct sequencing of 54 PCR products confirmed the exact detection of 54 bla genes (FIGS. 2a to 2h). Notably, although there was not any optimization process, the multiplex PCR experiments with several templates (five-eight; e.g., five in C1 and eight in A1, Table 1) obtained from 54 positive control strains showed that 54 bla type-specific PCR products were exactly detected in eight multiplex PCR assays (eight lane is of FIGS. 2a to 2h), suggesting the good quality of 54 designed primer pairs. Similarly, the exact detection of bla genes was confirmed through direct sequencing of PCR products (FIGS. 2a to 2h). However, each multiplex PCR assay cannot discriminate whether one clinical strain harbors only one bla gene or more than two. If one of eight strains harbors two bla gene types (e.g., A1-1 and A1-5 of FIGS. 2a to 2h) and another strain harbors only one bla gene type (e.g., A1-5) in case of a multiplex PCR tube A1 containing eight primer pairs and eight templates obtained from eight positive control strains, one band (A1-5) is overlapped in an agarose gel of this multiplex PCR assay. To solve this problem, it was need that the multiplex PCR assay per a control strain had to be performed with eight multiplex PCR tubes (A1-D2) and only one template obtained from a control strain.

Figure 4A:
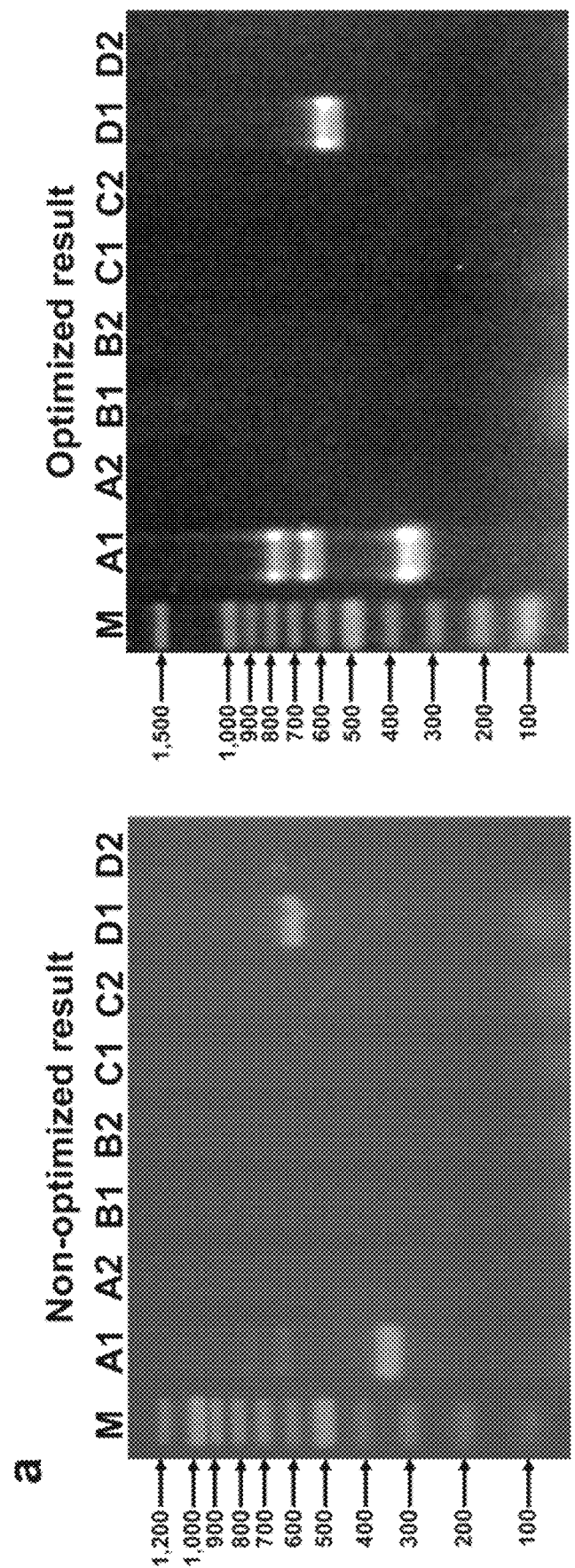
Figure 4C:
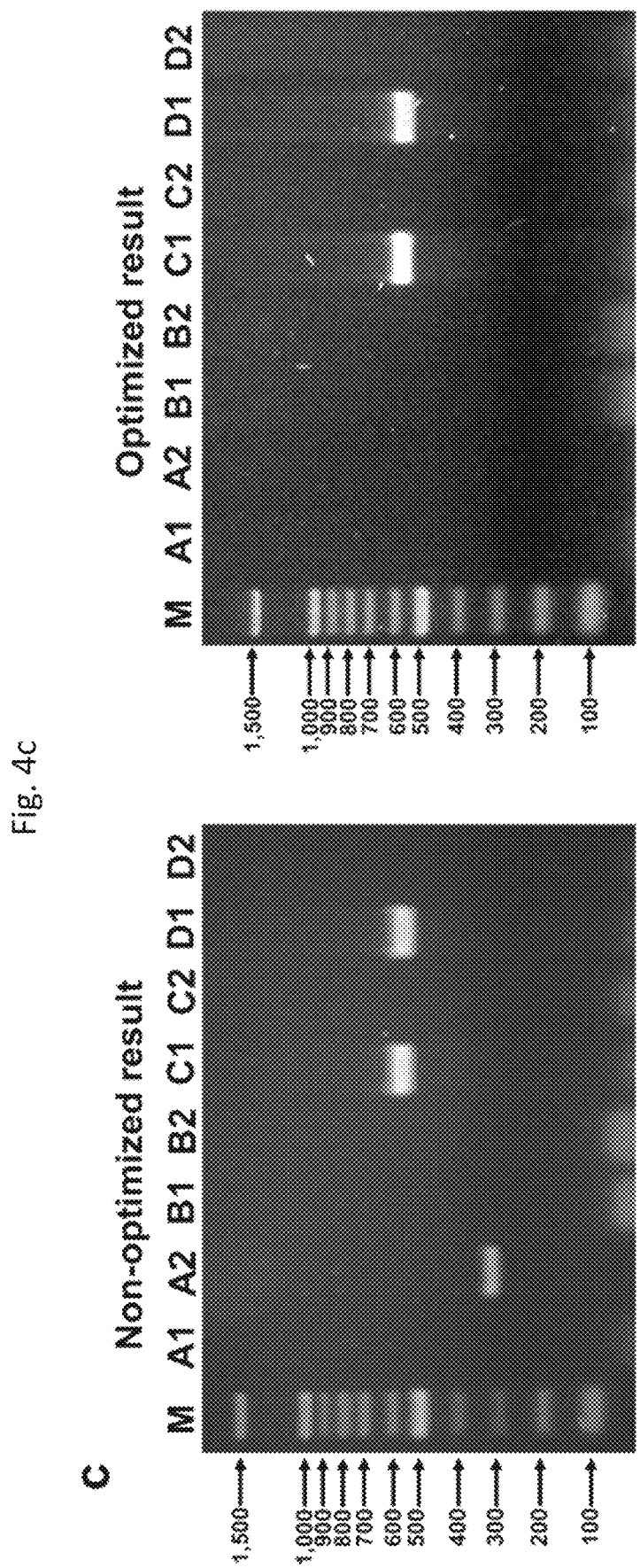
Figure 4D:
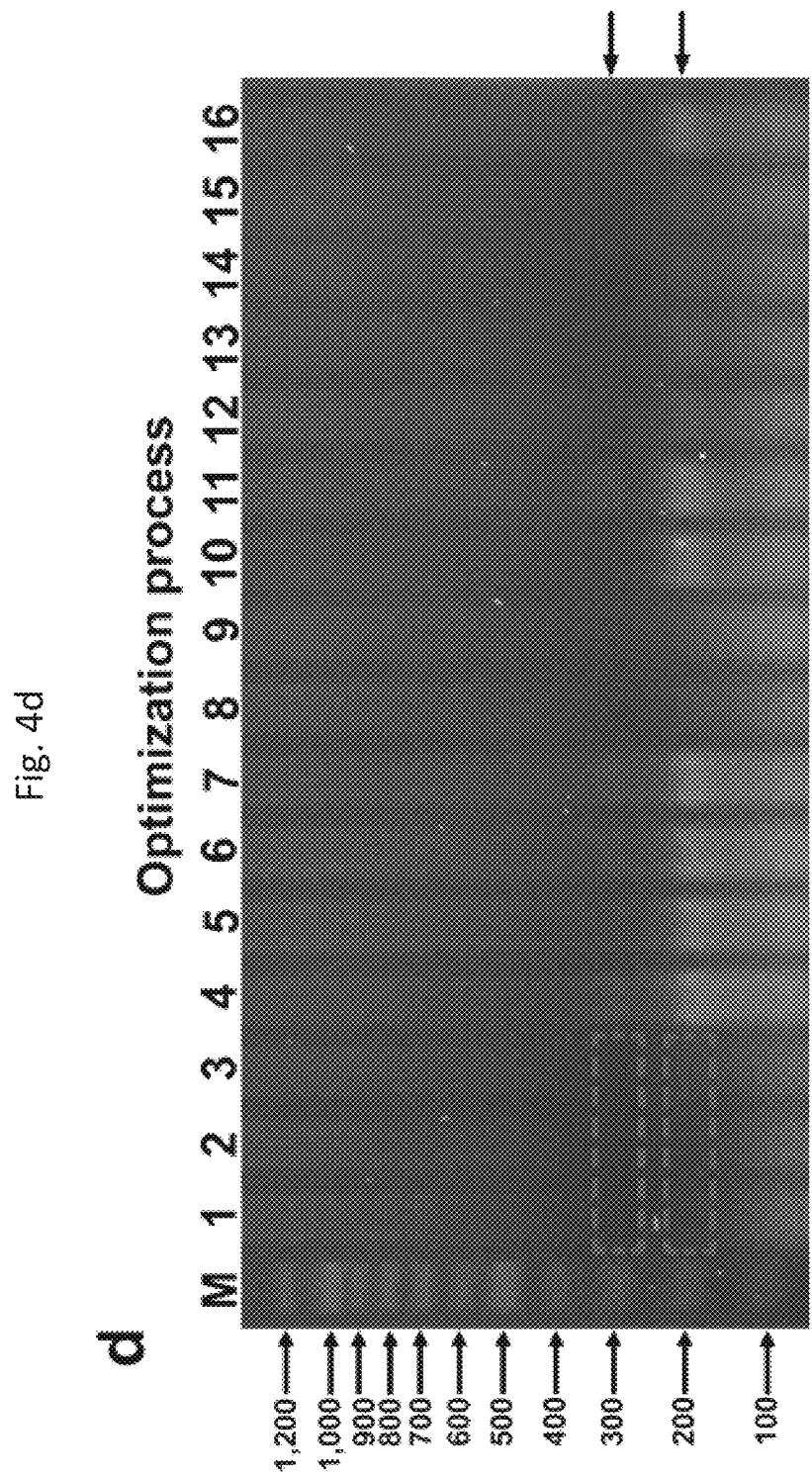
Figure 4E:
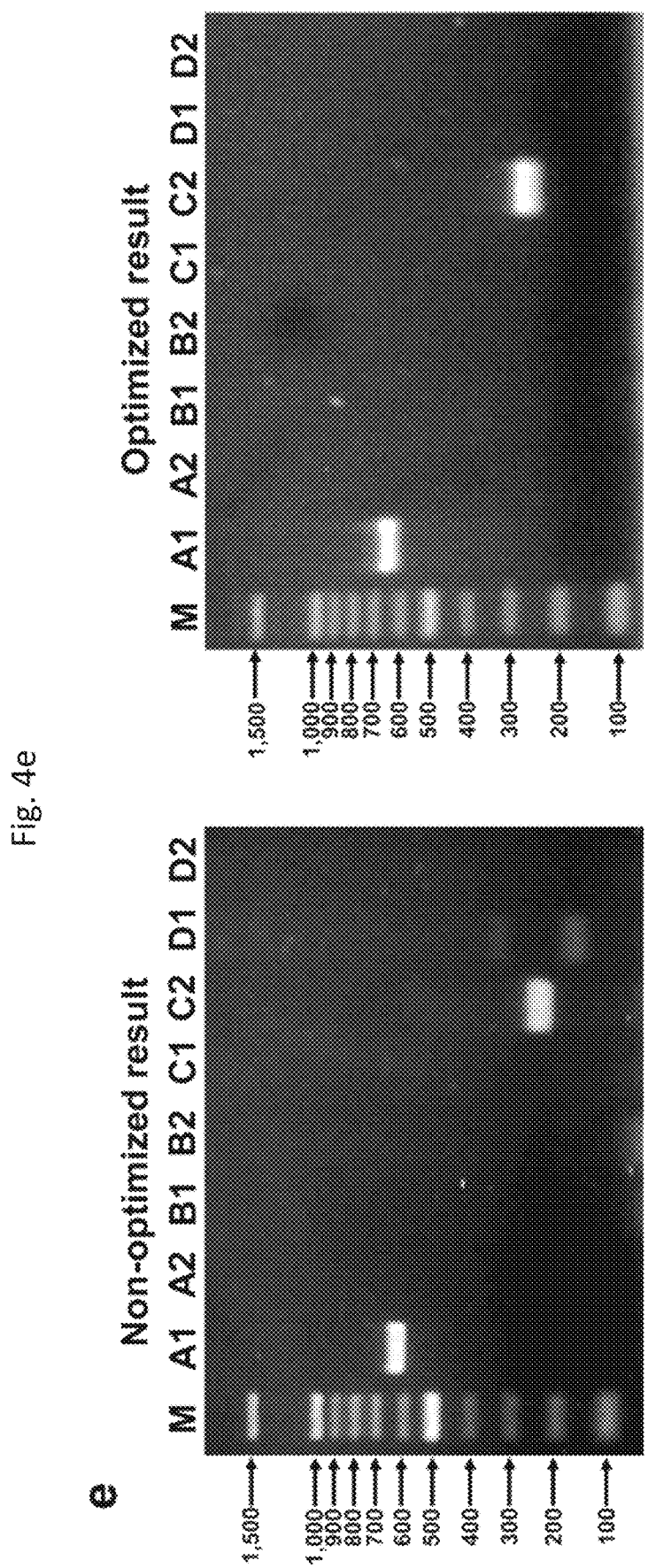

However, unlike the simplex PCR assays, the multiplex PCR assay triggered two problems, the weak intensity of an amplification product of GES type genes and some false positive bands by chromosomal cross-hybridization. Novel optimization processes were needed to solve these problems. The exact in silicoprimer design to detect all clinically-important bla genes cannot generate false negative bands. However, false positive bands cannot be prevented without our novel and unique optimization processes described below. Although the weak intensity of an amplification product was easily solved through increasing the length of GES type-specific primer pairs (FIG. 4a), much efforts were required to eliminate amplification of the false positive band by chromosomal cross-hybridization. To identify which primer is responsible for false positive bands shown in the multiplex PCR assays, many multiplex PCR assays using primer mixtures without one primer were performed (Online Method). As a result, we could find that false positive PCR products were generated by chromosomal cross-hybridization between the forward (or reverse) primer of one bla gene type and the reverse (or forward) primer of another type (FIGS. 4b to 4e). Suspicious primers were redesigned and the redesigned primers were effective for the optimized multiplex PCRs with complete specificity (FIGS. 4c and 4e). Theses novel optimization processes can remove all false positive bands identified in multiplex PCR assays using 100 control strains (Table 3: and FIGS. 3a-1 to 3h-3).

TABLE 3

| | Detection of β-lactamase (bla) gene[a] | | |
|---|---|---|---|
| Control strains | Positive results | Negative results | Total |
| Positive strains | 100 | 0 | 100 |
| Negative strains | 0 | 72 | 72 |
| Total | | | 172 |

[a]Sensitivity = 100%, specificity = 100%, positive predictive value = 100%, negative predicted value = 100%.

On the contrary to positive controls, in the case of 72 negative control strains without any targeted bla genes (FIGS. 3a-1 to 3h-3), any PCR product was not detected in all strains tested, except (a) ampC genes already existing in the genome of an *E. coli* strain K-12 and its derivatives[18]; and (b) additional bla genes newly detected by the $_{LARGE-SCALE}$blaFinder because previously-reported primers could detect only limited types of bla genes (FIGS. 3a-1 to 3h-3). Therefore, these results suggest that this $_{LARGE-SCALE}$blaFinder can detect all clinically-important bla genes with the complete specificity and sensitivity (Table 3).

Notably, multiplex PCR experiments in 12 strains could detect 24 additional unreported bla genes in the strains that were previously studied (Table 4).

TABLE 4

| Strain | bla gene(s) reported by previous investigators | Additional bla gene type(s) detected by $_{LARGE-SCALE}$blaFinder | Position at FIGS. 3a-1 to 3h-3 |
|---|---|---|---|
| *Escherichia coli* ECLA-4[23] | SHV-2a | TEM type, BER (EC2, KL, AmpC-10) type | a-18 |

TABLE 4-continued

| Strain | bla gene(s) reported by previous investigators | Additional bla gene type(s) detected by $_{LARGE-SCALE}$blaFinder | Position at FIGS. 3a-1 to 3h-3 |
|---|---|---|---|
| *Escherichia coli* ECZP-1[23] | SHV-12 | TEM type, BER (EC2, KL, AmpC-10) type | a-20 |
| *Klebsiella pneumoniae* CL5761[24] | KPC-3 | TEM type, SHV type | a-21 |
| *Klebsiella pneumoniae* CHAK36[25] | GES-5, SHV-12, OXA-17 | TEM type | a-23 |
| *Escherichia coli* A15R(+)[26] | CTX-M-3 | TEM type, BER (EC2, KL, AmpC-10) type | b-10 |
| *Escherichia coli* K0519020[27] | CTX-M-15 | TEM type, OXA-1 type, BER (EC2, KL, AmpC-10) type | b-12 |
| *Escherichia coli* K986110[28] | CMY-11 | TEM type, OXA-1 type, BER (EC2, KL, AmpC-10) type | f-13 |
| *Escherichia coli* J53-2R(+)[29] | FOX-3 | TEM type | f-18 |
| *Acinetobacter baumannii* K0420859[30] | OXA-23 | OXA-10 type, ADC (AmpC-5) type | g-17 |

For example, although the report in 2004 showed that an *Escherichia coli* strain K986110 had a CMY-1 type (CMY-11) bla gene, the $_{LARGE-SCALE}$blaFinder detected three additional bla gene types such as OXA-1 type, TEM type, and BER (EC2, KL, AmpC-10) type. The sequence of each additional bla gene was identified by direct sequencing of PCR products. Similarly, previous report showed that a *Klebsiella pneumoniae* strain CL5761 isolated at the Tisch Hospital, New York, was resistant to carbapenems and harbored a KPC type bla gene of class A. But, through the $_{LARGE-SCALE}$blaFinder, additional two bla genes (TEM and SHV types) were found in this KPC-3 producing strain (Table 4). These results demonstrated that previous methods detecting only limited types of bla genes can miss unexpected bla genes existing in pathogenic bacteria. In summary, because molecular methods that are able to detect only partial bla gene types cannot detect bla genes beyond the bounds of previous methods, they have the possibility to give researchers an insufficient result, like the case of an *Escherichia coli* strain K986110. In contrast, our method can detect all clinically-important bla genes including unexpected bla genes undetected by previous methods. Therefore, these results suggest that our method has the ability to give researchers the exact information about bla gene(s) existing in pathogenic bacteria Optimization Processes of Multiplex PCR Conditions To select optimal Taq DNA polymerase, a variety of Taq DNA polymerases were used as follows: Expand High Fidelity PCR system (Roche Diagnostics: DNA-free and high-purity enzyme without pre-mixture), 2×Prime STAR Premix (TaKaRa: DNA-free and high-purity enzyme), 2×EmeraldAmp GT PCR Master mix (TaKaRa), and 2×DiaStar™ Multiplex PCR Smart mix (SolGent: DNA-free). Multiplex PCRs using the heated colony supernatant as a template DNA were performed at various conditions recommended by each manufacture. As a result, only 2×DiaStar™ Multiplex PCR Smart mix was effective for multiplex PCRs, so it was selected as Taq DNA polymerase for multiplex PCRs. According to our previous report[34], commercial Taq DNA polymerase could be contaminated with the TEM type bla gene. Therefore, Taq DNA polymerase should be treated DNase I or DNA-free[34]. Otherwise, false positive PCR product could be detected due to the contamination of the TEM type bla gene. For optimization of the annealing temperature, the gradient PCR machine (PCR Thermal Cycler Dice™ TP600, TaKaRa) was used. Multiplex PCR assays were performed at a variety of annealing temperatures (60° C.~65° C.). Consequently, the optimal annealing temperature (64° C.) was selected. Because Dallenne et al.[12] used various concentrations of primers (0.2 mM~0.5 mM), a variety of primer concentrations (0.1 mM~0.5 mM) were tested. There was no PCR product at a concentration of 0.1 mM and false positive bands were detected at primer concentrations in the range between 0.3 mM and 0.5 mM. As only an expected DNA product was detected at the primer concentration of 0.2 mM, 0.2 mM was selected as the optimal concentration of primer for multiplex PCRs. In summary, the optimal multiplex PCR condition was selected as follows. A single colony from an overnight culture was picked using 10 µl pipette tip and was suspended in a total volume of 20 µl of 0.1% Triton X-100, immediately followed by heating of the cell suspension at 100° C. for 10 min. After removing cellular debris by a centrifugation step at 18,000×g for 30 sec, the supernatant (1 µl) was added to each multiplex PCR tube (34 µl per PCR mixture of each tube [A1, A2, B1, B2, C1, C2, D1, or D2]) containing 1×DiaStar™ Multiplex PCR Smart mix and 0.2 mM bla type-specific primers (A1: 16 primers; A2: 10; B1: 16; B2: 16; C1: 10; C2: 10; D1: 16; D2: 14, Table 5).

TABLE 5

| Component | Multiplex tube A1 | Multiplex tube A2 | Multiplex tube B1 | Multiplex tube B2 | Multiplex tube C1 | Multiplex tube C2 | Multiplex tube D1 | Multiplex tube D2 |
|---|---|---|---|---|---|---|---|---|
| Multiplex PCR master mixture[a] | 18 µL | 18 µL | 18 µL | 18 µL | 18 µL | 18 µL | 18 µL | 18 µL |
| Primer mixture[b] | 12 µL | 7.5 µL | 12 µL | 12 µL | 7.5 µL | 7.5 µL | 12 µL | 10.5 µL |
| RNase-free water | 4 µL | 8.5 µL | 4 µL | 4 µL | 8.5 µL | 8.5 µL | 4 µL | 5.5 µL |

TABLE 5-continued

| Component | Multiplex tube A1 | Multiplex tube A2 | Multiplex tube B1 | Multiplex tube B2 | Multiplex tube C1 | Multiplex tube C2 | Multiplex tube D1 | Multiplex tube D2 |
|---|---|---|---|---|---|---|---|---|
| Template DNA (supernatant of FIG. 1)[c] | 1 μL | 1 μL | 1 μL | 1 μL | 1 μL | 1 μL | 1 μL | 1 μL |
| Total volume per tube | | | | 35 μL | | | | |

[a]1 × DiaStar ™ Multiplex PCR Smart mix (0.3 mM dNTP, 2.5 mM MgCl$_2$, and 100 U/mL DiaStar ™ Fh-Taq: SolGent, Korea)
[b]0.2 μM bla type-specific primer mixture (16 primers in A1; 10 primers in A2; 16 primers in B1; 16 primers in B2; 10 primers in C1; 10 primers in C2; 16 primers in D1;

Eight multiplex PCR tubes were needed to test a single strain and the total volume of each multiplex PCR mixture was 35 μl (Table 5). Amplification was performed with the following thermal cycling conditions: initial denaturation at 95° C. for 5 min; 30 cycles of 95° C. for 30 sec, 64° C. for 40 sec, and 72° C. 50 sec; and a final elongation step at 72° C. for 7 min. Amplicons were analyzed by electrophoresis on a 2% agarose gel at 100 V for 1 h and ethidium bromide staining. A 100 bp DNA ladder (Biosesang) was used as a size maker.

Novel Optimization Processes of 54 Primer Pairs

Even though each primer pair was designed to be bound to only target bla genes and all primer pairs was validated by simplex and multiplex PCR assays (FIG. 1), several false positive bands among 100 control strains were detected in some multiplex PCR tubes, including A1, A2, C1, C2, and D1 multiplex tubes. DNA sequence analysis showed that false positive amplicons were PCR products of chromosomal genes from control strains, but not specific bla genes. Consequently, we could find that false positive PCR products were generated by chromosomal cross-hybridization between the forward (or reverse) primer of one bla gene type and the forward (or reverse) primer of another type (FIGS. 4c and 4e). To identify which primer is responsible for the false positive band(s), multiplex PCR assays using primer mixtures without one primer were performed. In case of the false positive band (FIG. 4c) detected in multiplex tube A2 containing 10 different primers, 10 multiplex PCR assays with nine primers were needed and each assay mixture did not have one different primer. In a multiplex PCR assay of tube A2 using a OXA-240-producing strain, the multiplex PCR assay without the forward primer of CTX-M-1 type (5'-AGTTCACGCTGATGGCGAC-3') and another multiplex PCR assay without the forward primer of CTX-M-25 type (5'-AAAAGCGTAAGGCGGGCGA-3') showed no false positive band (FIG. 4b). Therefore, these two primers were responsible for the false positive band. Two redesigned primers (CTX-M-1-F; 5'-CAGTTCACGCTGATGGCGAC-3' and CTX-M-25-F; 5'-TAATGACGACAGCCTGT-GTTTC-3') were effective for multiplex PCRs with complete specificity and fortunately, they didn't generate any false positive band in a multiplex tube A2 (FIG. 4c). Unlike the case of multiplex PCR tube A2, in a multiplex PCR assay of tube D1 using a TEM-30-producing strain as template, two false positive bands were detected. Through the novel optimization process same to that of multiplex PCR tube A2 (FIG. 4d), three primers, the primer pair of OXA-1 type (5'-CAATCATACACCAAAGACGTGGA-3' and 5'-GCT-TCCTGTAAGTGCGGACAC-3') and the forward primer of OXA-2 type (5'-AGTTGTGGCAGACGAACGC-3'), were responsible for two false positive bands. In this case, by only one redesigned primer (OXA-1-R; 5'-AGCTTCCTG-TAAGTGCGGACACA-3'), two false positive bands could be removed in multiplex PCR assays (FIG. 4e). In the case of GES type in multiplex PCR tube A1, the weak intensity of an amplification product was observed (FIG. 4a). To increase the amount of the GES type amplicon, the length of GES type primer pairs increased. Subsequently, more thick bands were obtained.

Positive or Negative Control Strains

For validation of 54 designed primer pairs and optimization of the multiplex PCR assays, well-characterized 100 bacterial strains with known (reported) bla genes were used as positive controls and 72 bacterial strains without any targeted bla gene were used as negative controls. Any PCR product was not detected in all negative strains tested, except (i) ampC genes already existing in the genome of an *E. coli* strain K-12 and its derivatives (*E. coli* TOP 10, *E. coli* MG1655, *E. coli* ATCC25922, *E. coli* DH5α, *E. coli* BL21 [DE3], *E. coli* HB4, *E. coli* JF701, *E. coli* J703, and so on) that have the ampCbla gene in the genome[18]; and (ii) additional bla genes newly detected by our $_{LARGE-SCALE}$blaFinder because previously-reported primers could detect only limited types of bla genes (FIGS. 3a-1 to 3h-3).

Example 4

Detection of bla Genes in Clinical Strains

To confirm the applicability of the $_{LARGE-SCALE}$blaFinder, multiplex PCR assays were performed on 403 clinical strains, as determined by phenotypic analysis and not characterized by molecular methods. As a result, all strains had at least single bla gene, suggesting the surprising accuracy of this method. Single bla gene was detected in 78 strains, and 325 strains had more than two bla genes. And direct sequencing of all PCR products confirmed that this $_{LARGE-SCALE}$blaFinder could determine the exact bla gene typing of clinical strains without any false positive or false negative result (Table 6).

TABLE 6

| Strains | Number of strains tested | Number of positive strains detected by this method | Number of positive strains confirmed through direct sequencing of PCR products | Detection percentage (%) |
|---|---|---|---|---|
| *Escherichia coli* | 199 | 199 | 199 | 100 |
| *Klebsiella pneumoniae* | 144 | 144 | 144 | 100 |
| *Acinetobacter baumannii* | 38 | 38 | 38 | 100 |
| *Serratia marcescens* | 22 | 22 | 22 | 100 |

Therefore, our method can be sufficiently applied as the clinical diagnostic technique for identification and gene typing of β-lactamases in bacterial pathogens.

Clinical Strains Used for Assay ($_{LARGE-SCALE}$blaFinder) Validation

The $_{LARGE-SCALE}$blaFinder was further assessed using 403 clinical strains, which were selected by phenotypic analysis such as MIC (minimum inhibitory concentration), but not characterized by any molecular method. MICs and their interpretation (resistance) were determined by the following method: Susceptibility was determined on Mueller-Hinton agar plates (Difco Laboratories) containing serially twofold-diluted β-lactams. Plates were inoculated with a Steers replicator (Craft Machine) and ca $10^4$ CFU per spot were incubated at 37° C. for 18 h. The results were interpreted by using the Clinical and Laboratory Standards Institute (CLSI) criteria. All strains exhibited resistance to one or more β-lactam(s).

Sequencing Analysis of Multiplex PCR Products

In order to confirm the exact bla gene type, all PCR products amplified in multiplex PCR assays were identified by direct sequencing of PCR products. Amplified PCR products were purified using a PCR purification kit (Qiagen) and bidirectional sequencing was performed using ABI Prism Big Dye Terminator Cycle Sequencing kit (Applied Biosystems) according to standard procedures. 54 designed primer pairs were used those for bidirectional sequencings.

Solution of the Big Problem in Studying β-Lactam Resistance

Until now, several molecular methods of the bla gene typing were developed to detect the existence of bla gene(s) in clinical strains (Table 7).

These methods could detect only the limited bla genes (less than 539 bla genes, Table 7), such as ESBL genes[11-15]. Because these methods cannot detect all clinically-important bla genes, they cannot perfectly explain results of the culture-based phenotypic tests[11-15,19-21]. This is a big problem in studying β-lactam resistance, which can increase β-lactam resistance due to inappropriate β-lactam use. However, our $_{LARGE-SCALE}$blaFinder, designed to solve this problem, could detect all clinically-important 1,228 bla genes with 100% specificity and 100% sensitivity, and through experimental tests in 403 clinical strains, the availability of this method in the clinical environment was also proved (Table 7). Although perfect specificity and sensitivity were shown in three previous methods, these methods had the low number of control and test (clinical) strains (Table 7). Furthermore, unlike previous methods[12,19,21], our method need one optimized Multiplex PCR per clinical strain and thus it can be a rapid and low-cost molecular method. Therefore, the present invention can be used as a clinical tool for confirming results of the classical culture-based phenotypic method.

The global health crisis by the upsurge of multiple antibiotic resistances strongly triggers the development of the fast and accurate molecular method for detecting antibiotic resistant genes. Although several methods detecting bla genes were reported, these methods could detect only small bla genes. The present inventors provide new $_{LARGE-SCALE}$blaFinder that is able to detect all clinically-important bla genes and also identify the exact gene type of detected bla genes, which was confirmed by DNA sequence analysis. This optimized multiplex PCR method is a fast, low-cost, and accurate technique for the screening of bla genes encountered in the clinical environment. This method would be suitable for clinical microbiological laboratories without sophisticated instruments, providing accurate detection of β-lactam resistant pathogens and offering rapid and reliable guidelines for appropriate antibiotic prescribing on the basis of case-by-case scientific data.

The big problem in investigating β-lactam resistance is the fact that using primer pairs only for several interesting bla gene types, most researchers detect bla genes in clinical strains. This tendency has an important limitation that these methods cannot detect the unexpected bla genes which exist within the target strain but do not belong to the primer-specific bla gene types. Because the detection of all existing bla genes is significantly important for the accurate prescribing of antibiotics, this problem can increase the possibility of inadequate treatments for bacterial infections. Susceptibility tests using classical culture-based phenotypic tests are the routine method that is able to determine the suscepti-

TABLE 7

| Source or reference | Method type | Number of detectable bla genes | Number of control strains tested | Number of clinically-isolated strains tested | Specificity in control strains | Specificity in clinically-isolated strains |
|---|---|---|---|---|---|---|
| Perez-Perez et al.[11] | Multiplex PCR | 30 | 29 | 22 | ND$^a$ | ND |
| Dallenne et al.[12] | Multiplex and simplex PCRs | 539 | 42 | 31 | ND | ND |
| Poirel et al.[14] | Multiplex PCR | 105 | 13 | 27 | 100% | 100% |
| Monteiro et al.[15] | Multiplex real-time PCR | 80 | 30 | 28 | 100% | 100% |
| Ellem et al.[13] | Multiplex real-time PCR | 123 | 41 | 617 | 100% | 97.6% |
| Grimm et al.[21] | Microarray with simplex PCR | 102 | 1 | 12 | ND | ND |
| Leinberger et al.[19] | Microarray with dualplex and multiplex PCRs | 156 | 14 | 60 | 100% | 100% |
| Barisic et al.[20] | Padlock probes | 33 | 33 | 70 | ND | 98.6% |
| This invention ($_{LARGE-SCALE}$blaFinder) | Multiplex PCR | 1,228 | 172 | 403 | 100% | 100% |

$^a$Not determined.

bilities to most β-lactam antibiotics. However, this procedure can provide inaccurate information about which bla gene types exist in the bacterial strain, especially in strains with ESBL and carbapenemase genes. A recent study demonstrated that ESBL and carbapenemase detection based on the susceptibility tests causes the failure of therapy to levels similar to cases of success[22]. Additionally, although ESBL and carbapenemase detection for epidemiological purpose is continuously advocated, some laboratories do not seek theses enzymes for treatment purposes[22]. Therefore, the inaccuracy and experimental difficulty of the phenotypic test can be complemented by the molecular gene typing method. Because our method is accurately able to detect all clinically-important bla genes through only one optimized multiplex PCR assay (with eight PCR tubes) per clinical strain, this technique can solve this big problem in detecting β-lactam resistance.

To remove false positive and false negative results in multiplex PCR assays, we carried out the novel and elaborate optimization processes of 54 primer pairs, such as the removal of chromosomal cross-hybridization between primers belonging to different types (FIGS. 4b and 4c). Based on these optimization processes, new bla genes that will be reported in the future can be included in this detection method. Therefore, the present invention becomes probably a molecular diagnostic tool to be easily upgradeable.

The present invention can be successfully applied to all clinical strains exhibiting resistance to any β-lactam antibiotic. In the study of 403 clinical strains, there was distinct concordance between the phenotypic resistance to β-lactams and the bla gene type(s) detected by method of the present invention, suggesting the highly sensitive and specific feature of our molecular method. This ability to identify antibiotic-resistant pathogens rapidly will be one of major strategies for the success of Antimicrobial Stewardship Programs (ASPs), the institutional programs to optimize antimicrobial therapy, reduce treatment-related cost, improve clinical outcomes and safety, and reduce or stabilize antibiotic resistance.

In conclusion, the present inventors develop the molecular diagnostic method that can detect all clinically-important bla genes in various pathogenic strains using only one unique multiplex PCR condition. The present invention enables rapid and accurate detection of all clinically-important bla genes, such as ESBL and carbapenemase genes. So, the present invention can be promptly used as effective molecular diagnostic technique for identification of bla genes in bacterial pathogens and will provide an important aid for appropriate antibiotic prescribing and minimizing the spread of resistant bacteria.

REFERENCES

1. Livermore, D. M. Fourteen years in resistance. *Int. J. Antimicrob. Agents* 39, 283-294 (2012).
2. Worthington, R. J. & Melander, C. Overcoming resistance to β-lactam antibiotics. *J. Org. Chem.* 78, 4207-4213 (2013).
3. Bush, K. Alarming β-lactamase-mediated resistance in multidrug-resistant Enterobacteriaceae. *Curr. Opin. Microbiol.* 13, 558-564 (2010).
4. Bush, K. Proliferation and significance of clinically relevant β-lactamases. *Ann. N.Y. Acad. Sci.* 1277, 84-90 (2013).
5. Abraham, E. P. & Chain, E. An enzyme from bacteria able to destroy penicillin. *Nature* 146, 837 (1940).
6. Livermore, D. M. Defining an extended-spectrum β-lactamase. *Clin. Microbiol. Infect.* 14 Suppl 1, 3-10 (2008).
7. Lee, J. H., Jeong, S. H., Cha, S.-S. & Lee, S. H. A lack of drugs for antibiotic-resistant Gram-negative bacteria. *Nat. Rev. Drug Discov.* 6, doi:10.1038/nrd2201-c1031 (2007).
8. Lee, J. H., Bae, I. K. & Lee, S. H. New definitions of extended-spectrum β-lactamase conferring worldwide emerging antibiotic resistance. *Med. Res. Rev.* 32, 216-232 (2012).
9. Okeke, I. N., et al. Diagnostics as essential tools for containing antibacterial resistance. *Drug Resist. Updat.* 14, 95-106 (2011).
10. Swayne, R., Ellington, M. J., Curran, M. D., Woodford, N. & Aliyu, S. H. Utility of a novel multiplex TaqMan PCR assay for metallo-β-lactamase genes plus other TaqMan assays in detecting genes encoding serine carbapenemases and clinically significant extended-spectrum β-lactamases. *Int. J. Antimicrob. Agents* 42, 352-356 (2013).
11. Perez-Perez, F. J. & Hanson, N. D. Detection of plasmid-mediated AmpC β-lactamase genes in clinical isolates by using multiplex PCR. *J. Clin. Microbiol.* 40, 2153-2162 (2002).
12. Dallenne, C., Da Costa, A., Decre, D., Favier, C. & Arlet, G. Development of a set of multiplex PCR assays for the detection of genes encoding important β-lactamases in Enterobacteriaceae. *J. Antimicrob. Chemother.* 65, 490-495 (2010).
13. Ellem, J., Partridge, S. R. & Iredell, J. R. Efficient direct extended-spectrum β-lactamase detection by multiplex real-time PCR: accurate assignment of phenotype by use of a limited set of genetic markers. *J. Clin. Microbiol.* 49, 3074-3077 (2011).
14. Poirel, L., Walsh, T. R., Cuvillier, V. & Nordmann, P. Multiplex PCR for detection of acquired carbapenemase genes. *Diagn. Microbiol. Infect. Dis.* 70, 119-123 (2011).
15. Monteiro, J., Widen, R. H., Pignatari, A. C., Kubasek, C. & Silbert, S. Rapid detection of carbapenemase genes by multiplex real-time PCR. *J. Antimicrob. Chemother.* 67, 906-909 (2012).
16. Voets, G. M., Fluit, A. C., Scharringa, J., Cohen Stuart, J. & Leverstein-van Hall, M. A. A set of multiplex PCRs for genotypic detection of extended-spectrum β-lactamases, carbapenemases, plasmid-mediated AmpC β-lactamases and OXA β-lactamases. *Int. J. Antimicrob. Agents* 37, 356-359 (2011).
17. Chroma, M., Hricova, K., Kolar, M., Sauer, P. & Koukalova, D. Using newly developed multiplex polymerase chain reaction and melting curve analysis for detection and discrimination of β-lactamases in *Escherichia coli* isolates from intensive care patients. *Diagn. Microbiol. Infect. Dis.* 71, 181-191 (2011).
18. Jaurin, B. & Grundstrom, T. ampC cephalosporinase of *Escherichia coli* K-12 has a different evolutionary origin from that of β-lactamases of the penicillinase type. *Proc. Natl. Acad. Sci. USA* 78, 4897-4901 (1981).
19. Leinberger, D. M., et al. Integrated detection of extended-spectrum-β-lactam resistance by DNA microarray-based genotyping of TEM, SHV, and CTX-M genes. *J. Clin. Microbiol.* 48, 460-471 (2010).
20. Barisic, I., et al. Multiplex detection of antibiotic resistance genes using padlock probes. *Diagn. Microbiol. Infect. Dis.* 77, 118-125 (2013).
21. Grimm, V, et al. Use of DNA microarrays for rapid genotyping of TEM β-lactamases that confer resistance. *J. Clin. Microbiol.* 42, 3766-3774 (2004).

22. Livermore, D. M., et al. Are susceptibility tests enough, or should laboratories still seek ESBLs and carbapenemases directly? *J. Antimicrob. Chemother.* 67, 1569-1577 (2012).

23. Nuesch-Inderbinen, M. T., Kayser, F. H. & Hachler, H. Survey and molecular genetics of SHV β-lactamases in Enterobacteriaceae in Switzerland: two novel enzymes, SHV-11 and SHV-12. *Antimicrob. Agents Chemother.* 41, 943-949 (1997).

24. Woodford, N., et al. Outbreak of *Klebsiella pneumoniae* producing a new carbapenem-hydrolyzing class A β-lactamase, KPC-3, in a New York Medical Center. *Antimicrob. Agents Chemother.* 48, 4793-4799 (2004).

25. Jeong, S. H., et al. First outbreak of *Klebsiella pneumoniae* clinical isolates producing GES-5 and SHV-12 extended-spectrum β-lactamases in Korea. *Antimicrob. Agents Chemother.* 49, 4809-4810 (2005).

26. Bonnet, R., et al. A novel CTX-M β-lactamase (CTX-M-8) in cefotaxime-resistant Enterobacteriaceae isolated in Brazil. *Antimicrob. Agents Chemother.* 44, 1936-1942 (2000).

27. Ryoo, N. H., et al. Dissemination of SHV-12 and CTX-M-type extended-spectrum β-lactamases among clinical isolates of *Escherichia coli* and *Klebsiella pneumoniae* and emergence of GES-3 in Korea. *J. Antimicrob. Chemother.* 56, 698-702 (2005).

28. Lee, S. H., et al. Characterization of bla$_{CMY-11}$, an AmpC-type plasmid-mediated β-lactamase gene in a Korean clinical isolate of *Escherichia coli. J. Antimicrob. Chemother.* 49, 269-273 (2002).

29. Marchese, A., Arlet, G., Schito, G. C., Lagrange, P. H. & Philippon, A. Characterization of FOX-3, an AmpC-type plasmid-mediated β-lactamase from an Italian isolate of *Klebsiella oxytoca. Antimicrob. Agents Chemother.* 42, 464-467 (1998).

30. Jeon, B. C., et al. Investigation of a nosocomial outbreak of imipenem-resistant *Acinetobacter baumannii* producing the OXA-23 β-lactamase in korea. *J. Clin. Microbiol.* 43, 2241-2245 (2005).

31. Untergasser, A., et al. Primer3—new capabilities and interfaces. *Nucleic. Acids Res.* 40, e115 (2012).

32. Kibbe, W. A. OligoCalc: an online oligonucleotide properties calculator. *Nucleic. Acids Res.* 35, W43-46 (2007).

33. Ye, J., et al. Primer-BLAST: a tool to design target-specific primers for polymerase chain reaction. *BMC Bioinformatics* 13, 134 (2012).

34. Song, J. S., et al. Removal of contaminating TEM-1a β-lactamase gene from commercial Taq DNA polymerase. *J. Microbiol.* 44, 126-128 (2006).

35. Ambler R P. The structure of β-lactamases. Philos Trans R Soc Lond B Biol Sci 1980; 289: 321-31.

---

What is claimed is:

1. A method for treating a patient with bacterial infection, the method comprising:
    determining a β-lactamase (bla) gene of a bacterial pathogen in the patient by performing a multiplex polymerase chain reaction (PCR) with primer pairs;
    determining a β-Lactam antibiotics to which the bacterial pathogen is not resistant, in accordance with the determination of the β-lactamase (bla) gene; and
    administering the β-Lactam antibiotics to the patient,
        wherein the primer pairs comprise:
            at least two primer pairs selected from the primer pair group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16;
            at least two primer pairs selected from the primer pair group consisting of a pair of Seq. No. 17 and 18, a pair of Seq. No. 19 and 20, a pair of Seq. No. 21 and 22, a pair of Seq. No. 23 and 24, and a pair of Seq. No. 25 and 26;
            at least two primer pairs selected from the primer pair group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, and a pair of Seq. No. 41 and 42;
            at least two primer pairs selected from the primer pair group consisting of a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58;
            at least two primer pairs selected from the primer pair group consisting of a pair of Seq. No. 59 and 60, a pair of Seq. No. 61 and 62, a pair of Seq. No. 63 and 64, a pair of Seq. No. 65 and 66, and a pair of Seq. No. 67 and 68;
            at least two primer pairs selected from the primer pair group consisting of a pair of Seq. No. 69 and 70, a pair of Seq. No. 71 and 72, a pair of Seq. No. 73 and 74, a pair of Seq. No. 75 and 76, a pair of Seq. No. 77 and 78;
            at least two primer pairs selected from the primer pair group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, and a pair of Seq. No. 93 and 94; and
            at least two primer pairs selected from the primer pair group consisting of a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108.

2. The method of claim 1, wherein the primer pairs comprise:
    at least three primer pairs selected from the group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16;
    at least three primer pairs selected from the group consisting of a pair of Seq. No. 17 and 18, a pair of Seq. No. 19 and 20, a pair of Seq. No. 21 and 22, a pair of Seq. No. 23 and 24, and a pair of Seq. No. 25 and 26;
    at least three primer pairs selected from the group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, and a pair of Seq. No. 41 and 42;
    at least three primer pairs selected from the group consisting of a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58;
    at least three primer pairs selected from the group consisting of a pair of Seq. No. 59 and 60, a pair of Seq. No. 61 and 62, a pair of Seq. No. 63 and 64, a pair of Seq. No. 65 and 66, and a pair of Seq. No. 67 and 68;
    at least three primer pairs selected from the group consisting of a pair of Seq. No. 69 and 70, a pair of Seq. No. 71 and 72, a pair of Seq. No. 73 and 74, a pair of Seq. No. 75 and 76, and a pair of Seq. No. 77 and 78;
    at least three primer pairs selected from the group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, and a pair of Seq. No. 93 and 94; and
    at least three primer pairs selected from the group consisting of a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108.

3. The method of claim 2, wherein the primer pairs comprise:
    at least four primer pairs selected from the group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16;
    at least four primer pairs selected from the group consisting of a pair of Seq. No. 17 and 18, a pair of Seq. No. 19 and 20, a pair of Seq. No. 21 and 22, a pair of Seq. No. 23 and 24, and a pair of Seq. No. 25 and 26;
    at least four primer pairs selected from the group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, and a pair of Seq. No. 41 and 42;
    at least four primer pairs selected from the group consisting of a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58;
    at least four primer pairs selected from the group consisting of a pair of Seq. No. 59 and 60, a pair of Seq. No. 61 and 62, a pair of Seq. No. 63 and 64, a pair of Seq. No. 65 and 66, and a pair of Seq. No. 67 and 68;
    at least four primer pairs selected from the group consisting of a pair of Seq. No. 69 and 70, a pair of Seq.

No. 71 and 72, a pair of Seq. No. 73 and 74, a pair of Seq. No. 75 and 76, and a pair of Seq. No. 77 and 78, at least four primer pairs selected from the group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, and a pair of Seq. No. 93 and 94; and at least four primer pairs selected from the group consisting of a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108.

4. The method of claim 3, wherein the primer pairs comprise:

at least five primer pairs selected from the group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16;

at least five primer pairs selected from the group consisting of a pair of Seq. No. 17 and 18, a pair of Seq. No. 19 and 20, a pair of Seq. No. 21 and 22, a pair of Seq. No. 23 and 24, and a pair of Seq. No. 25 and 26;

at least five primer pairs selected from the group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, and a pair of Seq. No. 41 and 42;

at least five primer pairs selected from the group consisting of a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58;

at least five primer pairs selected from the group consisting of a pair of Seq. No. 59 and 60, a pair of Seq. No. 61 and 62, a pair of Seq. No. 63 and 64, a pair of Seq. No. 65 and 66, and a pair of Seq. No. 67 and 68;

at least five primer pairs selected from the group consisting of a pair of Seq. No. 69 and 70, a pair of Seq. No. 71 and 72, a pair of Seq. No. 73 and 74, a pair of Seq. No. 75 and 76, and a pair of Seq. No. 77 and 78, at least five primer pairs selected from the group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, and a pair of Seq. No. 93 and 94; and at least five primer pairs selected from the group consisting of a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108.

5. The method of claim 1, wherein the multiplex PCR is performed by using at least eight multiplex polymerase chain reaction (PCR) tubes which comprise:

a first multiplex PCR tube containing the at least two primer pairs selected from the primer pair group consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16;

a second multiplex PCR tube containing the at least two primer pairs selected from the primer pair group consisting of a pair of Seq. No. 17 and 18, a pair of Seq. No. 19 and 20, a pair of Seq. No. 21 and 22, a pair of Seq. No. 23 and 24, and a pair of Seq. No. 25 and 26;

a third multiplex PCR tube containing the at least two primer pairs selected from the primer pair group consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, and a pair of Seq. No. 41 and 42;

a fourth multiplex PCR tube containing the at least two primer pairs selected from the primer pair group consisting of a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58;

a fifth multiplex PCR tube containing the at least two primer pairs selected from the primer pair group consisting of a pair of Seq. No. 59 and 60, a pair of Seq. No. 61 and 62, a pair of Seq. No. 63 and 64, a pair of Seq. No. 65 and 66, and a pair of Seq. No. 67 and 68;

a sixth multiplex PCR tube containing the at least two primer pairs selected from the primer pair group consisting of a pair of Seq. No. 69 and 70, a pair of Seq. No. 71 and 72, a pair of Seq. No. 73 and 74, a pair of Seq. No. 75 and 76, a pair of Seq. No. 77 and 78;

a seventh multiplex PCR tube containing the at least two primer pairs selected from the primer pair group consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, and a pair of Seq. No. 93 and 94; and an eighth multiplex PCR tube containing the at least two primer pairs selected from the primer pair group consisting of a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108.

6. A method for treating a patient with bacterial infection, the method comprising:

determining a β-lactamase (bla) gene of a bacterial pathogen in the patient by performing a multiplex polymerase chain reaction (PCR) with a detection kit;

determining a β-Lactam antibiotics to which the bacterial pathogen is not resistant, in accordance with the determination of the β-lactamase (bla) gene; and administering the β-Lactam antibiotics to the patient, wherein the detection kit comprises:

a recombinant hot start Taq DNA polymerase; and at least eight multiplex polymerase chain reaction (PCR) tubes which comprise:

a first multiplex PCR tube containing at least two primer pairs selected from the primer pairs consisting of a pair of Seq. No. 1 and 2, a pair of Seq. 3 and 4, a pair of Seq. No. 5 and 6, a pair of Seq. No. 7 and 8, a pair of Seq. No. 9 and 10, a pair of Seq. No. 11 and 12, a pair of Seq. No. 13 and 14, and a pair of Seq. No. 15 and 16;

a second multiplex PCR tube containing at least two primer pairs selected from the primer pairs consisting of a pair of Seq. No. 17 and 18, a pair of Seq. No. 19 and 20, a pair of Seq. No. 21 and 22, a pair of Seq. No. 23 and 24, and a pair of Seq. No. 25 and 26;

a third multiplex PCR tube containing at least two primer pairs selected from the primer pairs consisting of a pair of Seq. No. 27 and 28, a pair of Seq. No. 29 and 30, a pair of Seq. No. 31 and 32, a pair of Seq. No. 33 and 34, a pair of Seq. No. 35 and 36, a pair of Seq. No. 37 and 38, a pair of Seq. No. 39 and 40, and a pair of Seq. No. 41 and 42;

a fourth multiplex PCR tube containing at least two primer pairs selected from the primer pairs consisting of a pair of Seq. No. 43 and 44, a pair of Seq. No. 45 and 46, a pair of Seq. No. 47 and 48, a pair of Seq. No. 49 and 50, a pair of Seq. No. 51 and 52, a pair of Seq. No. 53 and 54, No. 55 and 56, and a pair of Seq. 57 and 58;

a fifth multiplex PCR tube containing at least two primer pairs selected from the primer pairs consisting of a pair of Seq. No. 59 and 60, a pair of Seq. No. 61 and 62, a pair of Seq. No. 63 and 64, a pair of Seq. No. 65 and 66, and a pair of Seq. No. 67 and 68;

a sixth multiplex PCR tube containing at least two primer pairs selected from the primer pairs consisting of a pair of Seq. No. 69 and 70, a pair of Seq. No. 71 and 72, a pair of Seq. No. 73 and 74, a pair of Seq. No. 75 and 76, a pair of Seq. No. 77 and 78;

a seventh multiplex PCR tube containing at least two primer pairs selected from the primer pairs consisting of a pair of Seq. No. 79 and 80, a pair of Seq. No. 81 and 82, a pair of Seq. No. 83 and 84, a pair of Seq. No. 85 and 86, a pair of Seq. No. 87 and 88, a pair of Seq. No. 89 and 90, a pair of Seq. No. 91 and 92, and a pair of Seq. No. 93 and 94; and an eighth multiplex PCR tube containing at least two primer pairs selected from the primer pairs consisting of a pair of Seq. No. 95 and 96, a pair of Seq. No. 97 and 98, a pair of Seq. No. 99 and 100, a pair of Seq. No. 101 and 102, a pair of Seq. No. 103 and 104, a pair of Seq. No. 105 and 106, and a pair of Seq. No. 107 and 108.

* * * * *